(12) United States Patent
Tiruppathi et al.

(10) Patent No.: US 7,429,563 B2
(45) Date of Patent: *Sep. 30, 2008

(54) PEPTIDE CARRIER FOR DRUG DELIVERY

(75) Inventors: Chinnaswamy Tiruppathi, Elmhurst, IL (US); Asrar B. Malik, Hinsdale, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 3 days.

This patent is subject to a terminal disclaimer.

(21) Appl. No.: 11/514,578

(22) Filed: Sep. 1, 2006

(65) Prior Publication Data

US 2007/0077239 A1    Apr. 5, 2007

Related U.S. Application Data

(63) Continuation-in-part of application No. PCT/US2005/007442, filed on Mar. 3, 2005.

(60) Provisional application No. 60/559,532, filed on Apr. 5, 2004, provisional application No. 60/550,373, filed on Mar. 5, 2004.

(51) Int. Cl.
*A01N 37/18* (2006.01)
*A61K 38/00* (2006.01)

(52) U.S. Cl. ............................. 514/2; 530/300; 530/350

(58) Field of Classification Search ................. 530/350, 530/300; 514/2
See application file for complete search history.

(56) References Cited

U.S. PATENT DOCUMENTS

| | | | |
|---|---|---|---|
| 4,018,884 | A | 4/1977 | Cleeland, Jr. et al. |
| 4,744,981 | A | 5/1988 | Pavanasasivam |
| 4,897,255 | A | 1/1990 | Fritzberg et al. |
| 4,988,496 | A | 1/1991 | Srinivasan et al. |
| 5,106,951 | A | 4/1992 | Morgan, Jr. et al. |
| 5,460,961 | A | 10/1995 | Deby et al. |
| 5,493,007 | A | 2/1996 | Burnier et al. |
| 5,708,009 | A | 1/1998 | Glasebrook |
| 5,708,010 | A | 1/1998 | Glasebrook |
| 5,981,194 | A | 11/1999 | Jefferies et al. |
| 5,985,272 | A | 11/1999 | Deby et al. |
| 6,172,043 | B1 | 1/2001 | Ingram et al. |

FOREIGN PATENT DOCUMENTS

| | | |
|---|---|---|
| EP | 0 367 566 | 5/1990 |
| WO | WO 91/18982 | 12/1991 |
| WO | WO98/07848 | * 2/1998 |
| WO | WO-9807848 | 2/1998 |
| WO | WO 01/59459 | 8/2001 |
| WO | WO 02/13843 | 2/2002 |

OTHER PUBLICATIONS

Hashinaka et al. 1988; Biochemistry 27: 5906-5914.*
Abu-Soud et al., Nitric oxide is a physiological substrate for mammalian peroxidases, J. Biol. Chem., 275:37524-37532, 2000.
Agner, Verdoperoxidase, Acta Physiol. Scand., 2(suppl 8):5-62, 1941.
Andersson et al., Large-scale synthesis of peptides, Biopolymers Pept. Sci., 55:227-250, 2000.
Andersson et al., The role of the propeptide for processing and sorting of human myeloperoxidase, J. Biol. Chem., 273:4747-4753, 1988.
Anwer et al., Backbone modifications in cyclic peptides. Conformational analysis of a cyclic pseudopentapeptide containing a thiomethylene ether amide bond replacement, Int. J. Pept. Protein Res., 36:392-399, 1990.
Baldus et al., Myeloperoxidase serum levels predict risk in patients with acute coronary syndromes, Circulation, 108:1440-1445, 2003.
Barany et al., Solid phase peptide synthesis (chapter 1), The Peptides: Anaysis, Synthesis, Biology, edited by Gross et al., Academic Press, 2:1-284, 1979.
Blair et al., Linkage of cytotoxic agents to immunoglobulins, J. Immunol. Methods, 59:129-143, 1983.
Blättler et al., New heterobifunctional protein crosslinking reagent that forms an acid-labile link, Biochem., 24:1517-1524, 1985.
Brennan et al., A tale of two controversies: defining both the role of peroxidases in nitrotyrosine formation in vivo using eosinophil peroxidase and myeloperoxidase-deficient mice, and the nature of peroxidase-generated reactive nitrogen species, J. Biol. Chem., 277:17415-17427, 2002.
Brennan et al., Prognostic value of myeloperoxidase in patients with chest pain, N. Eng. J. Med., 349:1595-1604, 2003.
Bundgaard, Vesicular transport in capillary endothelium: does it occur?, Faseb J., 42:2425-2430, 1983.
Burgess et al., DiSSiMiL: diverse small size mini-libraries applied to simple and rapid epitope mapping of a monoclonal antibody, J. Pept. Res., 57:68-76, 2001.
Carver et al., Caveolae: mining little caves for new cancer targets, Nat. Rev. Cancer, 3:571-581, 2003.
Cosman et al., Cloning, sequence and expression of human interleukin-2 receptor, Nature, 312:768-771, 1984.
Cosman et al., High level stable expression of human interleukin-2 receptors in mouse cells generates only low affinity interleukin-2 binding sites, Mol. Immunol., 23:935-941, 1986.
Daugherty et al., Myeloperoxidase, a catalyst for lipoprotein oxidation, is expressed in human atherosclerotic lesions, J. Clin. Invest., 94:437-444, 1994.
Dvorak et al., Structure of solid tumors and their vasculature: implications for therapy with monoclonal antibodies, Cancer Cells, 3:77-85, 1991.
Engelhard et al., The insect tracheal system: a conduit for the systemic spread of *Autographa californica* M nuclear polyhedrosis virus, PNAS USA, 91:3224-3227, 1994.
Fields, Peptides for the New Millennium, edited by Tam et al., Kluwer Academic Publisher, Dordrecht, 2000.

(Continued)

*Primary Examiner*—Karen Cochrane Carlson
(74) *Attorney, Agent, or Firm*—Marshall, Gerstein & Borun LLP

(57) ABSTRACT

The present invention is directed to compositions based on myeloperoxidase amino acid sequence which may be used as therapeutic agents or as delivery vehicles for the delivery of other therapeutic agents.

14 Claims, 15 Drawing Sheets

OTHER PUBLICATIONS

Fields, Solid-Phase Peptide Synthesis. Academic Press, San Diego, 1997.
GenBank Accession No. AAR99349, Myeloperoxidase precursor [*Mus musculus*], Mar. 1, 2005.
GenBank Accession No. AY500847, Myeloperoxidase precursor [*Mus musculus*], mRNA, complete cds, Mar. 1, 2005.
GenBank Accession No. $NM_{13}$ 000250, Myeloperoxidase [*Homo sapiens*], nuclear gene encoding mitochondrial protein, mRNA, Sep. 17, 2007.
GenBank Accession No. NM_010824, Myeloperoxidase [*Mus musculus*], mRNA, Sep. 3, 2007.
GenBank Accession No. NP_000241, Myeloperoxidase [*Homo sapiens*], Sep. 17, 2007.
GenBank Accession No. NP_034954, Myeloperoxidase [*Mus musculus*], Sep. 3, 2007.
GenBank Accession No. P05164, Myeloperoxidase precursor (MPO) [Contains: 89 kDa myeloperoxidase;84 kDa myeloperoxidase; myeloperoxidase light chain; myeloperoxidase heavy chain], Jul. 10, 2007.
Greenwald et al., Poly(ethylene glycol) conjugated drugs and prodrugs: a comprehensive review, Crit. Rev. Ther. Drug Carrier Syst., 17:101-161, 2000.
Harris et al., Pegylation: a novel process for modifying pharmacokinetics, Clin. Pharmacokinet., 40:539-551, 2001.
Hermanson, Bioconjugate Techniques, Academic Press, 1996.
Inman, Convalent linkage of functional groups, ligands, and proteins to polyacrylamide beads, Methods in Enzymology, Affinity Techniques, Enzyme Purification: Part B, edited by Jakoby et al., Academic Press, New York, 34:30-58, 1974.
Jain, The next frontier of molecular medicine: delivery of therapeutics, Nat. Med., 4:655-657, 1998.
Jansson, Oestrogen-induced enhancement of myeloperoxidase activity in human PMN leukocytes; a possible cause of oxidative stress in inflammatory cells, Free Rad. Res. Commun., 143:195-208, 1991.
John et al., Quantitative analysis of albumin uptake and transport in the rat microvessel endothelial monolayer, Am. J. Physiol Lung Cell. Mol. Physiol., 284:L187-L196, 2003.
Karas et al., Laser desorption ionization of proteins with molecular masses exceeding 10,000 daltons, Anal, Chem., 60:2299-2301, 1988.
King et al., Preparation of protein conjugates via intermolecular hydrazone linkage, Biochem., 25:5774-5779, 1986.
Kopecek et al., Water soluble polymers in tumor targeted delivery, J. Controlled Release., 74:147-158, 2001.
Lamb et al., Oxidative damage to proteins of bronchoalveolar lavage fluid in patients with acute respiratory distress syndrome; evidence for neutrophil-mediated hydroxylation, nitration, and chlorination, Crit. Care Med., 27:1738-1744, 1999.
Leeuwenburgh et al., Reactive nitrogen intermediates promote low density lipoprotein oxidation in human atherosclerotic intima, J. Biol. Chem., 272:1433-1436, 1997.
McIntosh et al., Caveolae require intact VAMP for targeted transport in vascular endothelium, Am. J. Physiol., 277:H2222-H2232, 1999.
McIntosh et al., Targeting endothelium and its dynamic caveolae for tissue-specific transcytosis in vivo: a pathway to overcome cell barriers to drug and gene delivery, PNAS USA 994:1996-2001, 2002.
Merrifield, Solid phase synthesis, Science, 232:341-347, 1986.
Miller et al., Targeted vectors for gene therapy, FASEB J., 9:190-199, 1995.
Minshall et al., Endothelial cell-surface gp60 activates vesicle formation and trafficking via G(i)-coupled Src kinase signaling pathway, J. Biol. Chem., 150:1057-1069, 2000.
Nachman et al., Pseudodipeptide analogs of the pyrokinin/PBAN (FXPRLa) insect neuropeptide family containing carbocyclic Pro-mimetic conformational components, Regul. Pept., 57:359-370, 1995.
Nathan et al., Copolymers of lysine and polyethylene glycol: a new family of functionalized drug carriers, Bioconj. Chem., 4:54-62, 1993.
Nathan et al., Hydrogels based on water-soluble poly(ether urethanes) derived from L-lysine and poly(ethylene glycol), Macromolecules, 25:4476-4484, 1992.
Oh et al., Dynamin at the neck of caveolae mediates their budding to form transport vesicles by GTP-driven fission from the plasma membrane of endothelium, J. Biol. Chem., 141:101-114, 1998.
Okayama et al., A cDNA cloning vector that permits expression of cDNA inserts in mammalian cells, Mol. Cell. Biol., 3:280-289, 1983.
Renkin, Capillary transport of macromolecules: pores and other endothelial pathways, J. Appl. Physiol., 58:315-325, 1985.
Retnoningrum et al., M12 protein from *Streptococcus pyogenes* is a receptor for immunoglobulin G3 and human albumin, Infect. Immunol., 62:2387-2394, 1994.
Rivera-Baeza et al., Backbone-to-backbone cyclized and linear pseudopeptide analogs of substance P as ligands to the substance P receptor from rat brain, Neuropeptides, 30:327-333, 1996.
Schnitzer et al., Endothelial caveolae have the molecular transport machinery for vesicle budding, docking, and fusion including Vamp, NSF, Snap, annexins, and GTPases, J. Biol. Chem., 270:14399-14404, 1995.
Schnitzer et al., Role of GTP hydrolysis in fission of caveolae directly from plasma membranes, Science, 274:239-242, 1996.
Schnitzer et al., Separation of caveolae from associated microdomains of GPI-anchored proteins, Science, 269:1435-1439, 1995.
Schnitzer, Update on the cellular and molecular basis of capillary permeability, Trends Cardiovasc. Med., 3:124-130, 1993.
Schnitzer, Vascular targeting as a strategy for cancer therapy, N. Engl. J. Med., 339:472-474, 1998.
Severs, Caveolae: static inpocketings of the plasma membrane, dynamic vesicles or plain artifact?, J. Cell Sci., 90:341-348, 1988.
Shishehbor et al., Association of nitrotyrosine levels with cardiovascular disease and modulation by statin therapy, JAMA, 289:1675-1680, 2003.
Smith et al., Molecular engineering of the *Autographa californica* nuclear polyhedrosis virus genome: deletion mutations within the polyhedrin gene, J. VIrol., 46:584-593, 1983.
Srinivasachar et al., New protein cross-linking reagents that are cleaved by mild acid, Biochem., 28:2501-2509, 1989.
Stewart et al., Solid Phase Peptide Synthesis, $2^{nd}$ edition, Pierce Chemical Co., 1984.
Tam et al., An $S_N 2$ deprotection of synthetic peptides with a low concentration of hydrofluoric acid in dimethyl sulfide: evidence and application in peptide synthesis, J. Am. Chem. Soc., 105:6442-6445, 1983.
Thrush et al., Immunotoxins: an update, Annu. Rev. Immunol., 14:49-71, 1996.
Tiruppathi et al., Albumin mediates the transcytosis of myeloperoxidase by means of caveolae in endothelial cells, PNAS USA, 101:7699-7704, 2004.
Tiruppathi et al., Gp60 activation mediates albumin transcytosis in endothelial cells by tyrosine kinase-dependent pathway, J. Biol. Chem., 272:25968-25975, 1997.
Tiruppathi et al., Isolation and characterization of a cell surface albumin-binding protein from vascular endothelial cells, PNAS USA, 93:250-254, 1996.
Tomlinson, Theory and practice of site-specific drug delivery, Adv. Drug Delivery Rev., 1:87-198, 1987.
Van Der Vliet et al., Myeloperoxidase and protein oxidation in cystic fibrosis, Am. J. Physiol. Lung Cell. Mol. Physiol., 279:L537-L546, 2000.
Vogel et al., Albumin uptake and transcytosis in endothelial cells in vivo induced by albumin-binding protein, Am. J. Physiol Lung Cell. Mol. Physiol., 281:L1512-L1522, 2001.
Wawizynczak et al., Methods for preparing immunotoxins: effect of the linkage on activity and stability (chapter 3), Immunoconjugates, edited by Vogel, Oxford University Press, 28-55, 1987.
Weinstein et al., The macroscopic and microscopic pharmacology of monoclonal antibodies, Int. J. Immunopharmacol., 14:457-463, 1992.
Wilchek et al., The avidin-biotin complex in bioanalytical applications, Anal. Biochem., 171:1-32, 1988.
Winterbourn et al.; Myeloperoxidase, Curr. Opin. Hematol., 7:53-58, 2000.

Wong, Chemistry of Protein Conjugation and Crosslinking. CRC Press, Ann Arbor, 1991.

Zalipsky et al., Poly(ethylene glycol)-grafted liposomes with oligopeptide or oligosaccharide ligands appended to the termini of the polymer chains, Bioconjug. Chem., 8:111-118, 1997.

Zhang et al., Association between myeloperoxidase levels and risk of coronary artery disease, JAMA, 286:2136-2142, 2001.

* cited by examiner

RLATELKSLNPRWDGERLYQEARKIVGAMV (WT)

(nMoles)  1.0   2.5   5.0   7.5   10

EARKIV

(nMoles)  1.0   2.5   5.0   7.5   10

GLATELGSLNPGWDGEGLYQEAGGIVGAMV (MT)

(nMoles)  1.0   2.5   5.0   7.5   10

RLATELKSLNPRWDGERLYQEARKIVGAMV (WT)

Soluble WT (nMoles)   0    10    20    50    100

Control            CD (5 mM, 20 min)

SEQUENCE LISTING

<160> NUMBER OF SEQ ID NOS: 37

<210> SEQ ID NO 1
<211> LENGTH: 2238
<212> TYPE: DNA
<213> ORGANISM: Homo sapiens

<400> SEQUENCE: 1

```
atgggggttc ccttcttctc ttctctcaga tgcatggtgg acttaggacc ttgctgggct      60
gggggtctca ctgcagagat gaagctgctt ctggccctag cagggctcct ggccattctg     120
gccacgcccc agccctctga aggtgctgct ccagctgtcc tggggaggt ggacacctcg      180 ttggtgctga gctccatgga ggaggccaag cagctggtgg acaaggccta caaggagcgg     240
cgggaaagca tcaagcagcg gcttcgcagc ggctcagcca gccccatgga actcctatcc     300
tacttcaagc agccggtggc agccaccagg acggcggtga gggccgctga ctacctgcac     360
gtggctctag acctgctgga gaggaagctg cggtccctgt ggcgaaggcc attcaatgtc     420
actgatgtgc tgacgcccgc ccagctgaat gtgttgtcca agtcaagcgg ctgcgcctac     480
caggacgtgg gggtgacttg cccggagcag gacaaatacc gcaccatcac cgggatgtgc     540
aacaacagac gcagccccac gctgggggcc tccaaccgtg cctttgtgcg ctggctgccg     600
gcggagtatg aggacggctt ctctcttccc tacggctgga cgcccggggt caagcgcaac     660
ggcttcccgg tggctctggc tcgcgcggtc tccaacgaga tcgtgcgctt ccccactgat     720
cagctgactc cggaccagga gcgctcactc atgttcatgc aatggggcca gctgttggac     780
cacgacctcg acttcacccc tgagccgcc gcccgggcct ccttcgtcac tggcgtcaac     840
tgcgagacca gctgcgttca gcagccgccc tgcttcccgc tcaagatccc gcccaatgac     900
ccccgcatca agaaccaagc cgactgcatc ccgttcttcc gctcctgccc ggcttgcccc     960
gggagcaaca tcaccatccg caaccagatc aacgcgctca cttccttcgt ggacgccagc    1020
atggtgtacg gcagcgagga gcccctggcc aggaacctgc gcaacatgtc caaccagctg    1080
gggctgctgg ccgtcaacca gcgcttccaa gacaacggcc gggccctgct gcccttttgac   1140 aacctgcacg atgaccctg tctcctcacc aaccgctcag cgcgcatccc ctgcttcctg    1200
gcaggggaca cccgttccag tgagatgccc gagctcacct ccatgcacac cctcttactt    1260
cgggagcaca accggctggc cacagagctc aagagcctga accctaggtg ggatggggag    1320
aggctctacc aggaagcccg gaagatcgtg ggggccatgg tccagatcat cacttaccgg    1380
gactacctgc cctggtgct ggggccaacg gccatgagga agtacctgcc cacgtaccgt    1440
tcctacaatg actcagtgga cccacgcatc gccaacgtct tcaccaatgc cttccgctac    1500
```

```
ggccacaccc tcatccaacc cttcatgttc cgcctggaca atcggtacca gcccatggaa    1560
cccaaccccc gtgtcccect cagcagggtc ttttttgcct cctggagggt cgtgctggaa    1620
ggtggcattg accccatcct ccggggcctc atggccaccc ctgccaagct gaatcgtcag    1680
aaccaaattg cagtggatga gatccgggag cgattgtttg agcaggtcat gaggattggg    1740
ctggacctgc tgctctgaa catgcagcgc agcagggacc acggcctccc aggatacaat     1800
gcctggaggc gcttctgtgg gctcccgcag cctgaaactg tgggccagct gggcacggtg    1860
ctgaggaacc tgaaattggc gaggaaactg atggagcagt atggcacgcc caacaacatc    1920
gacatctgga tgggcggcgt gtccgagcct ctgaagcgca aaggccgcgt gggcccactc    1980
ctcgcctgca tcatcggtac ccagttcagg aagctccggg atggtgatcg gttttggtgg    2040
gagaacgagg gtgtgttcag catgcagcag cgacaggccc tggcccagat ctcattgccc    2100
cggatcatct gcgacaacac aggcatcacc accgtgtcta agaacaacat cttcatgtcc    2160
aactcatatc cccgggactt tgtcaactgc agtacacttc ctgcattgaa cctggcttcc    2220
tggagggaag cctcctag                                                  2238
```

```
<210> SEQ ID NO 2
<211> LENGTH: 745
<212> TYPE: PRT
<213> ORGANISM: Homo sapiens

<400> SEQUENCE: 2

Met Gly Val Pro Phe Ser Ser Leu Arg Cys Met Val Asp Leu Gly
1               5                  10                  15

Pro Cys Trp Ala Gly Gly Leu Thr Ala Glu Met Lys Leu Leu Leu Ala
            20                  25                  30

Leu Ala Gly Leu Leu Ala Ile Leu Ala Thr Pro Gln Pro Ser Glu Gly
        35                  40                  45

Ala Ala Pro Ala Val Leu Gly Glu Val Asp Thr Ser Leu Val Leu Ser
    50                  55                  60

Ser Met Glu Glu Ala Lys Gln Leu Val Asp Lys Ala Tyr Lys Glu Arg
65                  70                  75                  80

Arg Glu Ser Ile Lys Gln Arg Leu Arg Ser Gly Ser Ala Ser Pro Met
                85                  90                  95

Glu Leu Leu Ser Tyr Phe Lys Gln Pro Val Ala Ala Thr Arg Thr Ala
            100                 105                 110

Val Arg Ala Ala Asp Tyr Leu His Val Ala Leu Asp Leu Leu Glu Arg
        115                 120                 125

Lys Leu Arg Ser Leu Trp Arg Arg Pro Phe Asn Val Thr Asp Val Leu
    130                 135                 140

Thr Pro Ala Gln Leu Asn Val Leu Ser Lys Ser Ser Gly Cys Ala Tyr
145                 150                 155                 160

Gln Asp Val Gly Val Thr Cys Pro Glu Gln Asp Lys Tyr Arg Thr Ile
                165                 170                 175

Thr Gly Met Cys Asn Asn Arg Arg Ser Pro Thr Leu Gly Ala Ser Asn
            180                 185                 190

Arg Ala Phe Val Arg Trp Leu Pro Ala Glu Tyr Glu Asp Gly Phe Ser
        195                 200                 205

Leu Pro Tyr Gly Trp Thr Pro Gly Val Lys Arg Asn Gly Phe Pro Val
    210                 215                 220

Ala Leu Ala Arg Ala Val Ser Asn Glu Ile Val Arg Phe Pro Thr Asp
225                 230                 235                 240
```

-continued

Gln Leu Thr Pro Asp Gln Glu Arg Ser Leu Met Phe Met Gln Trp Gly
                245                 250                 255

Gln Leu Leu Asp His Asp Leu Asp Phe Thr Pro Glu Pro Ala Ala Arg
            260                 265                 270

Ala Ser Phe Val Thr Gly Val Asn Cys Glu Thr Ser Cys Val Gln Gln
        275                 280                 285

Pro Pro Cys Phe Pro Leu Lys Ile Pro Pro Asn Asp Pro Arg Ile Lys
    290                 295                 300

Asn Gln Ala Asp Cys Ile Pro Phe Phe Arg Ser Cys Pro Ala Cys Pro
305                 310                 315                 320

Gly Ser Asn Ile Thr Ile Arg Asn Gln Ile Asn Ala Leu Thr Ser Phe
                325                 330                 335

Val Asp Ala Ser Met Val Tyr Gly Ser Glu Pro Leu Ala Arg Asn
            340                 345                 350

Leu Arg Asn Met Ser Asn Gln Leu Gly Leu Leu Ala Val Asn Gln Arg
        355                 360                 365

Phe Gln Asp Asn Gly Arg Ala Leu Leu Pro Phe Asp Asn Leu His Asp
    370                 375                 380

Asp Pro Cys Leu Leu Thr Asn Arg Ser Ala Arg Ile Pro Cys Phe Leu
385                 390                 395                 400

Ala Gly Asp Thr Arg Ser Ser Glu Met Pro Glu Leu Thr Ser Met His
                405                 410                 415

Thr Leu Leu Leu Arg Glu His Asn Arg Leu Ala Thr Glu Leu Lys Ser
            420                 425                 430

Leu Asn Pro Arg Trp Asp Gly Glu Arg Leu Tyr Gln Glu Ala Arg Lys
        435                 440                 445

Ile Val Gly Ala Met Val Gln Ile Ile Thr Tyr Arg Asp Tyr Leu Pro
    450                 455                 460

Leu Val Leu Gly Pro Thr Ala Met Arg Lys Tyr Leu Pro Thr Tyr Arg
465                 470                 475                 480

Ser Tyr Asn Asp Ser Val Asp Pro Arg Ile Ala Asn Val Phe Thr Asn
                485                 490                 495

Ala Phe Arg Tyr Gly His Thr Leu Ile Gln Pro Phe Met Phe Arg Leu
            500                 505                 510

Asp Asn Arg Tyr Gln Pro Met Glu Pro Asn Pro Arg Val Pro Leu Ser
        515                 520                 525

Arg Val Phe Phe Ala Ser Trp Arg Val Val Leu Glu Gly Gly Ile Asp
    530                 535                 540

Pro Ile Leu Arg Gly Leu Met Ala Thr Pro Ala Lys Leu Asn Arg Gln
545                 550                 555                 560

Asn Gln Ile Ala Val Asp Glu Ile Arg Glu Arg Leu Phe Glu Gln Val
                565                 570                 575

Met Arg Ile Gly Leu Asp Leu Pro Ala Leu Asn Met Gln Arg Ser Arg
            580                 585                 590

Asp His Gly Leu Pro Gly Tyr Asn Ala Trp Arg Arg Phe Cys Gly Leu
        595                 600                 605

Pro Gln Pro Glu Thr Val Gly Gln Leu Gly Thr Val Leu Arg Asn Leu
    610                 615                 620

Lys Leu Ala Arg Lys Leu Met Glu Gln Tyr Gly Thr Pro Asn Asn Ile
625                 630                 635                 640

Asp Ile Trp Met Gly Gly Val Ser Glu Pro Leu Lys Arg Lys Gly Arg
                645                 650                 655

Val Gly Pro Leu Leu Ala Cys Ile Ile Gly Thr Gln Phe Arg Lys Leu

-continued

```
                    660                 665                 670
Arg Asp Gly Asp Arg Phe Trp Trp Glu Asn Glu Gly Val Phe Ser Met
            675                 680                 685

Gln Gln Arg Gln Ala Leu Ala Gln Ile Ser Leu Pro Arg Ile Ile Cys
        690                 695                 700

Asp Asn Thr Gly Ile Thr Thr Val Ser Lys Asn Asn Ile Phe Met Ser
705                 710                 715                 720

Asn Ser Tyr Pro Arg Asp Phe Val Asn Cys Ser Thr Leu Pro Ala Leu
            725                 730                 735

Asn Leu Ala Ser Trp Arg Glu Ala Ser
        740                 745

<210> SEQ ID NO 3
<211> LENGTH: 12
<212> TYPE: PRT
<213> ORGANISM: Artificial sequence
<220> FEATURE:
<223> OTHER INFORMATION: Synthetic peptide

<400> SEQUENCE: 3

Glu Leu Lys Ser Leu Asn Pro Arg Trp Asp Gly Glu
1               5                   10

<210> SEQ ID NO 4
<211> LENGTH: 6
<212> TYPE: PRT
<213> ORGANISM: Artificial sequence
<220> FEATURE:
<223> OTHER INFORMATION: Synthetic peptide

<400> SEQUENCE: 4

Glu Ala Arg Lys Ile Val
1               5

<210> SEQ ID NO 5
<211> LENGTH: 15
<212> TYPE: PRT
<213> ORGANISM: Artificial sequence
<220> FEATURE:
<223> OTHER INFORMATION: Synthetic peptide

<400> SEQUENCE: 5

Glu Arg Leu Tyr Gln Glu Ala Arg Lys Ile Val Gly Ala Met Val
1               5                   10                  15

<210> SEQ ID NO 6
<211> LENGTH: 16
<212> TYPE: PRT
<213> ORGANISM: Artificial sequence
<220> FEATURE:
<223> OTHER INFORMATION: Synthetic peptide

<400> SEQUENCE: 6

Gly Glu Arg Leu Tyr Gln Glu Ala Arg Lys Ile Val Gly Ala Met Val
1               5                   10                  15

<210> SEQ ID NO 7
<211> LENGTH: 17
<212> TYPE: PRT
<213> ORGANISM: Artificial sequence
<220> FEATURE:
<223> OTHER INFORMATION: Synthetic peptide

<400> SEQUENCE: 7
```

-continued

Asp Gly Glu Arg Leu Tyr Gln Glu Ala Arg Lys Ile Val Gly Ala Met
1               5                   10                  15

Val

<210> SEQ ID NO 8
<211> LENGTH: 18
<212> TYPE: PRT
<213> ORGANISM: Artificial sequence
<220> FEATURE:
<223> OTHER INFORMATION: Synthetic peptide

<400> SEQUENCE: 8

Trp Asp Gly Glu Arg Leu Tyr Gln Glu Ala Arg Lys Ile Val Gly Ala
1               5                   10                  15

Met Val

<210> SEQ ID NO 9
<211> LENGTH: 19
<212> TYPE: PRT
<213> ORGANISM: Artificial sequence
<220> FEATURE:
<223> OTHER INFORMATION: Synthetic peptide

<400> SEQUENCE: 9

Arg Trp Asp Gly Glu Arg Leu Tyr Gln Glu Ala Arg Lys Ile Val Gly
1               5                   10                  15

Ala Met Val

<210> SEQ ID NO 10
<211> LENGTH: 20
<212> TYPE: PRT
<213> ORGANISM: Artificial sequence
<220> FEATURE:
<223> OTHER INFORMATION: Synthetic peptide

<400> SEQUENCE: 10

Pro Arg Trp Asp Gly Glu Arg Leu Tyr Gln Glu Ala Arg Lys Ile Val
1               5                   10                  15

Gly Ala Met Val
            20

<210> SEQ ID NO 11
<211> LENGTH: 21
<212> TYPE: PRT
<213> ORGANISM: Artificial sequence
<220> FEATURE:
<223> OTHER INFORMATION: Synthetic peptide

<400> SEQUENCE: 11

Asn Pro Arg Trp Asp Gly Glu Arg Leu Tyr Gln Glu Ala Arg Lys Ile
1               5                   10                  15

Val Gly Ala Met Val
            20

<210> SEQ ID NO 12
<211> LENGTH: 22
<212> TYPE: PRT
<213> ORGANISM: Artificial sequence
<220> FEATURE:
<223> OTHER INFORMATION: Synthetic peptide

<400> SEQUENCE: 12

Leu Asn Pro Arg Trp Asp Gly Glu Arg Leu Tyr Gln Glu Ala Arg Lys
1               5                   10                  15

```
Ile Val Gly Ala Met Val
            20

<210> SEQ ID NO 13
<211> LENGTH: 23
<212> TYPE: PRT
<213> ORGANISM: Artificial sequence
<220> FEATURE:
<223> OTHER INFORMATION: Synthetic peptide

<400> SEQUENCE: 13

Ser Leu Asn Pro Arg Trp Asp Gly Glu Arg Leu Tyr Gln Glu Ala Arg
1               5                   10                  15

Lys Ile Val Gly Ala Met Val
            20

<210> SEQ ID NO 14
<211> LENGTH: 24
<212> TYPE: PRT
<213> ORGANISM: Artificial sequence
<220> FEATURE:
<223> OTHER INFORMATION: Synthetic peptide

<400> SEQUENCE: 14

Lys Ser Leu Asn Pro Arg Trp Asp Gly Glu Arg Leu Tyr Gln Glu Ala
1               5                   10                  15

Arg Lys Ile Val Gly Ala Met Val
            20

<210> SEQ ID NO 15
<211> LENGTH: 25
<212> TYPE: PRT
<213> ORGANISM: Artificial sequence
<220> FEATURE:
<223> OTHER INFORMATION: Synthetic peptide

<400> SEQUENCE: 15

Leu Lys Ser Leu Asn Pro Arg Trp Asp Gly Glu Arg Leu Tyr Gln Glu
1               5                   10                  15

Ala Arg Lys Ile Val Gly Ala Met Val
            20                  25

<210> SEQ ID NO 16
<211> LENGTH: 26
<212> TYPE: PRT
<213> ORGANISM: Artificial sequence
<220> FEATURE:
<223> OTHER INFORMATION: Synthetic peptide

<400> SEQUENCE: 16

Glu Leu Lys Ser Leu Asn Pro Arg Trp Asp Gly Glu Arg Leu Tyr Gln
1               5                   10                  15

Glu Ala Arg Lys Ile Val Gly Ala Met Val
            20                  25

<210> SEQ ID NO 17
<211> LENGTH: 27
<212> TYPE: PRT
<213> ORGANISM: Artificial sequence
<220> FEATURE:
<223> OTHER INFORMATION: Synthetic peptide

<400> SEQUENCE: 17

Thr Glu Leu Lys Ser Leu Asn Pro Arg Trp Asp Gly Glu Arg Leu Tyr
```

```
                 1               5                  10                  15
Gln Glu Ala Arg Lys Ile Val Gly Ala Met Val
                20                  25

<210> SEQ ID NO 18
<211> LENGTH: 28
<212> TYPE: PRT
<213> ORGANISM: Artificial sequence
<220> FEATURE:
<223> OTHER INFORMATION: Synthetic peptide

<400> SEQUENCE: 18

Ala Thr Glu Leu Lys Ser Leu Asn Pro Arg Trp Asp Gly Glu Arg Leu
1               5                   10                  15

Tyr Gln Glu Ala Arg Lys Ile Val Gly Ala Met Val
                20                  25

<210> SEQ ID NO 19
<211> LENGTH: 29
<212> TYPE: PRT
<213> ORGANISM: Artificial sequence
<220> FEATURE:
<223> OTHER INFORMATION: Synthetic peptide

<400> SEQUENCE: 19

Leu Ala Thr Glu Leu Lys Ser Leu Asn Pro Arg Trp Asp Gly Glu Arg
1               5                   10                  15

Leu Tyr Gln Glu Ala Arg Lys Ile Val Gly Ala Met Val
                20                  25

<210> SEQ ID NO 20
<211> LENGTH: 30
<212> TYPE: PRT
<213> ORGANISM: Artificial sequence
<220> FEATURE:
<223> OTHER INFORMATION: Synthetic peptide

<400> SEQUENCE: 20

Arg Leu Ala Thr Glu Leu Lys Ser Leu Asn Pro Arg Trp Asp Gly Glu
1               5                   10                  15

Arg Leu Tyr Gln Glu Ala Arg Lys Ile Val Gly Ala Met Val
                20                  25                  30

<210> SEQ ID NO 21
<211> LENGTH: 31
<212> TYPE: PRT
<213> ORGANISM: Artificial sequence
<220> FEATURE:
<223> OTHER INFORMATION: Synthetic peptide

<400> SEQUENCE: 21

Asn Arg Leu Ala Thr Glu Leu Lys Ser Leu Asn Pro Arg Trp Asp Gly
1               5                   10                  15

Glu Arg Leu Tyr Gln Glu Ala Arg Lys Ile Val Gly Ala Met Val
                20                  25                  30

<210> SEQ ID NO 22
<211> LENGTH: 32
<212> TYPE: PRT
<213> ORGANISM: Artificial sequence
<220> FEATURE:
<223> OTHER INFORMATION: Synthetic peptide

<400> SEQUENCE: 22
```

-continued

His Asn Arg Leu Ala Thr Glu Leu Lys Ser Leu Asn Pro Arg Trp Asp
1               5                   10                  15

Gly Glu Arg Leu Tyr Gln Glu Ala Arg Lys Ile Val Gly Ala Met Val
            20                  25                  30

<210> SEQ ID NO 23
<211> LENGTH: 33
<212> TYPE: PRT
<213> ORGANISM: Artificial sequence
<220> FEATURE:
<223> OTHER INFORMATION: Synthetic peptide

<400> SEQUENCE: 23

Glu His Asn Arg Leu Ala Thr Glu Leu Lys Ser Leu Asn Pro Arg Trp
1               5                   10                  15

Asp Gly Glu Arg Leu Tyr Gln Glu Ala Arg Lys Ile Val Gly Ala Met
            20                  25                  30

Val

<210> SEQ ID NO 24
<211> LENGTH: 34
<212> TYPE: PRT
<213> ORGANISM: Artificial sequence
<220> FEATURE:
<223> OTHER INFORMATION: Synthetic peptide

<400> SEQUENCE: 24

Arg Glu His Asn Arg Leu Ala Thr Glu Leu Lys Ser Leu Asn Pro Arg
1               5                   10                  15

Trp Asp Gly Glu Arg Leu Tyr Gln Glu Ala Arg Lys Ile Val Gly Ala
            20                  25                  30

Met Val

<210> SEQ ID NO 25
<211> LENGTH: 35
<212> TYPE: PRT
<213> ORGANISM: Artificial sequence
<220> FEATURE:
<223> OTHER INFORMATION: Synthetic peptide

<400> SEQUENCE: 25

Leu Arg Glu His Asn Arg Leu Ala Thr Glu Leu Lys Ser Leu Asn Pro
1               5                   10                  15

Arg Trp Asp Gly Glu Arg Leu Tyr Gln Glu Ala Arg Lys Ile Val Gly
            20                  25                  30

Ala Met Val
        35

<210> SEQ ID NO 26
<211> LENGTH: 36
<212> TYPE: PRT
<213> ORGANISM: Artificial sequence
<220> FEATURE:
<223> OTHER INFORMATION: Synthetic peptide

<400> SEQUENCE: 26

Leu Leu Arg Glu His Asn Arg Leu Ala Thr Glu Leu Lys Ser Leu Asn
1               5                   10                  15

Pro Arg Trp Asp Gly Glu Arg Leu Tyr Gln Glu Ala Arg Lys Ile Val
            20                  25                  30

Gly Ala Met Val
        35

<210> SEQ ID NO 27
<211> LENGTH: 37
<212> TYPE: PRT
<213> ORGANISM: Artificial sequence
<220> FEATURE:
<223> OTHER INFORMATION: Synthetic peptide

<400> SEQUENCE: 27

Leu Leu Leu Arg Glu His Asn Arg Leu Ala Thr Glu Leu Lys Ser Leu
1               5                   10                  15
Asn Pro Arg Trp Asp Gly Glu Arg Leu Tyr Gln Glu Ala Arg Lys Ile
            20                  25                  30
Val Gly Ala Met Val
        35

<210> SEQ ID NO 28
<211> LENGTH: 38
<212> TYPE: PRT
<213> ORGANISM: Artificial sequence
<220> FEATURE:
<223> OTHER INFORMATION: Synthetic peptide

<400> SEQUENCE: 28

Thr Leu Leu Leu Arg Glu His Asn Arg Leu Ala Thr Glu Leu Lys Ser
1               5                   10                  15
Leu Asn Pro Arg Trp Asp Gly Glu Arg Leu Tyr Gln Glu Ala Arg Lys
            20                  25                  30
Ile Val Gly Ala Met Val
        35

<210> SEQ ID NO 29
<211> LENGTH: 39
<212> TYPE: PRT
<213> ORGANISM: Artificial sequence
<220> FEATURE:
<223> OTHER INFORMATION: Synthetic peptide

<400> SEQUENCE: 29

His Thr Leu Leu Leu Arg Glu His Asn Arg Leu Ala Thr Glu Leu Lys
1               5                   10                  15
Ser Leu Asn Pro Arg Trp Asp Gly Glu Arg Leu Tyr Gln Glu Ala Arg
            20                  25                  30
Lys Ile Val Gly Ala Met Val
        35

<210> SEQ ID NO 30
<211> LENGTH: 40
<212> TYPE: PRT
<213> ORGANISM: Artificial sequence
<220> FEATURE:
<223> OTHER INFORMATION: Synthetic peptide

<400> SEQUENCE: 30

Met His Thr Leu Leu Leu Arg Glu His Asn Arg Leu Ala Thr Glu Leu
1               5                   10                  15
Lys Ser Leu Asn Pro Arg Trp Asp Gly Glu Arg Leu Tyr Gln Glu Ala
            20                  25                  30
Arg Lys Ile Val Gly Ala Met Val
        35                  40

<210> SEQ ID NO 31

```
<211> LENGTH: 41
<212> TYPE: PRT
<213> ORGANISM: Artificial sequence
<220> FEATURE:
<223> OTHER INFORMATION: Synthetic peptide

<400> SEQUENCE: 31

Ser Met His Thr Leu Leu Arg Glu His Asn Arg Leu Ala Thr Glu
1               5                   10                  15

Leu Lys Ser Leu Asn Pro Arg Trp Asp Gly Glu Arg Leu Tyr Gln Glu
            20                  25                  30

Ala Arg Lys Ile Val Gly Ala Met Val
        35                  40

<210> SEQ ID NO 32
<211> LENGTH: 42
<212> TYPE: PRT
<213> ORGANISM: Artificial sequence
<220> FEATURE:
<223> OTHER INFORMATION: Synthetic peptide

<400> SEQUENCE: 32

Thr Ser Met His Thr Leu Leu Arg Glu His Asn Arg Leu Ala Thr
1               5                   10                  15

Glu Leu Lys Ser Leu Asn Pro Arg Trp Asp Gly Glu Arg Leu Tyr Gln
            20                  25                  30

Glu Ala Arg Lys Ile Val Gly Ala Met Val
        35                  40

<210> SEQ ID NO 33
<211> LENGTH: 43
<212> TYPE: PRT
<213> ORGANISM: Artificial sequence
<220> FEATURE:
<223> OTHER INFORMATION: Synthetic peptide

<400> SEQUENCE: 33

Leu Thr Ser Met His Thr Leu Leu Arg Glu His Asn Arg Leu Ala
1               5                   10                  15

Thr Glu Leu Lys Ser Leu Asn Pro Arg Trp Asp Gly Glu Arg Leu Tyr
            20                  25                  30

Gln Glu Ala Arg Lys Ile Val Gly Ala Met Val
        35                  40

<210> SEQ ID NO 34
<211> LENGTH: 44
<212> TYPE: PRT
<213> ORGANISM: Artificial sequence
<220> FEATURE:
<223> OTHER INFORMATION: Synthetic peptide

<400> SEQUENCE: 34

Glu Leu Thr Ser Met His Thr Leu Leu Arg Glu His Asn Arg Leu
1               5                   10                  15

Ala Thr Glu Leu Lys Ser Leu Asn Pro Arg Trp Asp Gly Glu Arg Leu
            20                  25                  30

Tyr Gln Glu Ala Arg Lys Ile Val Gly Ala Met Val
        35                  40

<210> SEQ ID NO 35
<211> LENGTH: 45
<212> TYPE: PRT
<213> ORGANISM: Artificial sequence
```

```
-continued

<220> FEATURE:
<223> OTHER INFORMATION: Synthetic peptide

<400> SEQUENCE: 35

Pro Glu Leu Thr Ser Met His Thr Leu Leu Arg Glu His Asn Arg
1               5                   10                  15

Leu Ala Thr Glu Leu Lys Ser Leu Asn Pro Arg Trp Asp Gly Glu Arg
            20                  25                  30

Leu Tyr Gln Glu Ala Arg Lys Ile Val Gly Ala Met Val
        35                  40                  45

<210> SEQ ID NO 36
<211> LENGTH: 46
<212> TYPE: PRT
<213> ORGANISM: Artificial sequence
<220> FEATURE:
<223> OTHER INFORMATION: Synthetic peptide

<400> SEQUENCE: 36

Met Pro Glu Leu Thr Ser Met His Thr Leu Leu Arg Glu His Asn
1               5                   10                  15

Arg Leu Ala Thr Glu Leu Lys Ser Leu Asn Pro Arg Trp Asp Gly Glu
            20                  25                  30

Arg Leu Tyr Gln Glu Ala Arg Lys Ile Val Gly Ala Met Val
        35                  40                  45

<210> SEQ ID NO 37
<211> LENGTH: 30
<212> TYPE: PRT
<213> ORGANISM: Artificial sequence
<220> FEATURE:
<223> OTHER INFORMATION: Synthetic peptide

<400> SEQUENCE: 37

Gly Leu Ala Thr Glu Leu Gly Ser Leu Asn Pro Gly Trp Asp Gly Glu
1               5                   10                  15

Gly Leu Tyr Gln Glu Ala Gly Gly Ile Val Gly Ala Met Val
            20                  25                  30
```

PEPTIDE CARRIER FOR DRUG DELIVERY

The present application is a continuation-in-part application of PCT/US05/007442 which was filed on Mar. 3, 2005 claiming benefit of priority of U.S. Provisional Patent Application No. 60/550,373 which was filed 5 Mar. 2004 and 60/559,532 which was filed 5 Apr. 2004. Each of the aforementioned applications is specifically incorporated herein by reference in its entirety This invention was made with government support under P01HL60678 and GM58531 awarded by the National Institutes of Health. The government has certain rights in the invention.

BACKGROUND

1. Field of the Invention

The present invention is generally directed to new methods and compositions for the delivery and uptake of therapeutic agents. The invention further provides new compositions for the treatment of disorders relating to increased activity or expression of myeloperoxidase.

2. Background of the Related Art

In the field of pharmaceutical and therapeutic intervention and treatment of disease states, a wide variety of macromolecular therapeutic agents have been developed, including proteins, peptides, nucleosides; nucleotides, antiviral agents, antineoplastic agents, antibiotics, etc., and prodrugs, precursors, derivatives and intermediates thereof. However, in order to be effective, such agents need to be delivered to the appropriate site of action. However, systemic delivery of such agents is often limited to the parenteral route of administration because such agents are typically extensively eliminated when administered orally. Even when administered parenterally, the uptake of many therapeutic agents at the target site of action is often limited by the inability of the therapeutic agent to get into the cellular site of action of the agent.

Thus, although many therapeutic agents have been tested in vitro, such agents frequently perform much less effectively in vivo where the agent must reach its target cells in a tissue in sufficient quantities to be potent while sparing bystander to their intended target sites of pharmacological action, namely, the cells inside the tissue (Jain, Nat. Med. 4, 655-657, 1998; Miller and Vile, FASEB J. 9, 190-199, 1995; Thrush et al., Annu. Rev. Immunol. 14, 49-71, 1995; Tomlinson, Adv. Drug Delivery Rev. 1, 87-198, 1987). For example, poor tissue penetration has hindered many monoclonal antibodies from reaching their cell-specific antigens to achieve effective tissue- or cell-directed pharmaco-delivery in vivo (Jain, Nat. Med. 4, 655-657, 1998, Thrush et al., Annu. Rev. Immunol. 14, 49-71, 1995; Tomlinson, Adv. Drug Delivery Rev. 1, 87-198, 1987; Dvorak et al., Cancer Cells 3, 77-85, 1991; Weinstein and van Osdol, Int. J. Immunopharmacol. 14, 457-463, 1992).

Another barrier to the uptake and delivery of blood-borne molecules a cellular site of action is the microvascular endothelium (Schnitzer, Trends Cardiovasc. Med. 3, 124-130, 1993; Renkin, J. Appl. Physiol. 134, 375-382, 1985). It is thought that there are specific transport mechanisms for the transendothelial transport of essential circulating blood macromolecules into the subendothelial space to meet the metabolic needs of the surrounding tissue cells (Schnitzer, Trends Cardiovasc. Med. 3, 124-130, 1993). Within the continuous endothelium there are distinct structures called caveolae. These flask-shaped invaginations in the plasma membrane of endothelial cells are open to the luminal blood vessel space and, therefore, accessible to molecules circulating in the blood vessel luminal space.

Caveolae may provide a trafficking pathway for macromolecules into and possibly across cells (Schnitzer N. Engl. J. Med. 339, 472-474, 1998, Schnitzer, Trends Cardiovasc. Med. 3, 124-130, 1993). Certain morphological studies have shown there are few plasmalemmal vesicles that exist free and unattached to other membranes inside the cell. These studies have led to the conclusion that caveolae are not dynamic, but rather static structures (Severs et al., J. Cell Sci. 90, 341-348, 1988; Bundgard, FASEB J. 42, 2425-2430, 1983). Nevertheless, caveolae are able to bud from the plasma membrane via a dynamin-mediated, GTP-dependent fission process (Oh et al., J. Biol. Chem., 141, 101-114, 1998, Schnitzer et al., Science 274, 239-242, 1996), and these structures contain key functional docking and fusion proteins (Schnitzer et al., Science 274, 239-242, 1996; McIntosh et al., Am. J. Physiol. 277, H2222-H2232, 1999; Schnitzer et al., Science 269, 1435-1439, 1995; Schnitzer et al., J. Biol. Chem. 270, 14399-14404, 1995). However, those skilled in the art have acknowledged that the ability of caveolae to mediate transcytosis remains unproven (McIntosh et al., Proc. Nat'l Acad. Sci., USA 99 (4):1996-2001, 2002). Therefore, the use of caveolae to overcome cell barriers to facilitate efficient pharmacodelivery in vivo along with detailed knowledge of the molecular composition and tissue-specific differences has been acknowledged as unknown (McIntosh et al., Proc. Nat'l Acad. Sci., USA 99 (4):1996-2001, 2002.

Albumin is a predominant plasma protein responsible for maintaining the transendothelial oncotic pressure gradient and regulating the transport of fatty acids, steroids, thyroxin and amino acids. Albumin is transported by the caveolae, and this transport is a key determinant of transcellular endothelial permeability (Tiruppathi et al., J. Biol. Chem., 272:25968-25975, 1997; Minshall et al., J. Biol. Chem., 150:1057-1069, 2000; Vogel et al., Am. J. Physiol Lung Cell Mol. Physiol. 281:L1512-L1522, 2001; John et al., Am. J. Physiol Lung Cell. Mol. Physiol. 284:L187-L196, 2003). The binding of albumin to Albumin-Binding Proteins (ABPs) localized in caveolae is essential for the transcellular permeability of albumin (Tiruppathi et al., J. Biol. Chem., 272:25968-25975, 1997; Minshall et al., J. Biol. Chem., 150:1057-1069, 2000; Vogel et al., Am. J. Physiol Lung Cell Mol. Physiol. 281: L1512-L1522, 2001; John et al., Am. J. Physiol Lung Cell. Mol. Physiol. 284:L187-L196, 2003). The ability of certain motifs or domains of peptides or proteins to interact with specific membrane components, followed by cellular uptake of the protein:receptor complex may point towards the potential application of such motifs in facilitating the delivery of drugs. However, the identity of these motifs remains to be determined for many proteins. In addition there remains a need to enhance the transport of an active agent through the endothelial lining of tissues. The identification of motifs of proteins that interact with cellular receptors and structures and allow the intracellular transport of those proteins and the subsequent binding of those motifs to active agents provides an elegant method of achieving enhanced transport active agents to which such motifs are conjugated.

SUMMARY OF THE INVENTION

The present invention is directed to peptide carriers that bind to albumin, such agents may be used to facilitate the delivery of a variety of agents through the caveolae. In specific embodiments, there is provided an albumin docking protein (ADP) comprising the sequence of ELKSLN- PRWDGE (SEQ ID NO:3) wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3. It is particularly contemplated that the sequence of SEQ ID NO:2 is excluded from the ADP compositions of the invention however, all variants or fragments of SEQ ID NO:2 that contain SEQ ID NO:3 are contemplated to be within the scope of the invention. The ADP may preferably be conjugated to an agent of interest. Such an agent may be any agent whose delivery via transcytosis is desired, and therefore the agent may be a therapeutic agent, a diagnostic agent, a marker of a disease, a labeled monoclonal antibody which binds a marker of a disease.

In specific embodiments, the therapeutic agent is selected from the group consisting of a protein, a chemotherapeutic agent, a protein nucleic acid, an siRNA molecule, an antisense molecule, and an expression construct comprising a nucleic acid that encodes a therapeutic protein of interest. The ADP and the agent of interest are directly linked to each other or alternatively may be linked through a linker. The linker may be peptide linker.

It is contemplated that the ADP in the compounds of the invention binds to albumin and mediates the uptake of the agent of interest via albumin-mediated transcytosis through caveolae. Preferably, the ADP in the compounds or peptides described herein comprises a positive charge. In specific embodiments, the ADP comprises residues RK of SEQ ID NO:2, as described in further detail in the specification. The ADP may further comprise sequence of EARKIV (SEQ ID NO:4), a sequence that is conserved in albumin binding proteins. In specific embodiments, the ADP comprises a sequence of any of the amino acid sequences of SEQ ID NO:5 to SEQ ID NO:36. In other specific embodiments, the ADP consists essentially of a sequence of any of the amino acids of SEQ ID NO:3, SEQ ID NO:5 through SEQ ID NO:36.

The present application details methods of delivering an agent into a cell comprising contacting the cell with an agent conjugated to an ADP comprising the sequence of SEQ ID NO:3 or a fragment or conservative variant thereof, that retains the albumin docking activity of a peptide of SEQ ID NO:3, wherein the transport of the agent conjugated to the ADP across the cell membrane of the cell is greater than the transport of the agent in the absence of conjugation to the ADP. In specific embodiments, the methods of delivery comprise contacting the cell with an agent conjugated to an ADP comprising the sequence of ELKSLNPRWDGE (SEQ ID NO:3) wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3

Also taught herein are methods of increasing transcytosis of an agent, comprising conjugating the agent to an ADP comprising the sequence of SEQ ID NO:3 or a fragment or conservative variant thereof, that retains the albumin docking activity of a peptide of SEQ ID NO:3, wherein transcytosis of the agent when conjugated to the ADP is greater than the transcytosis of the agent in the absence of the conjugation. In specific embodiments, the methods of increasing transcytosis of an agent involve conjugation of the agent with an ADP comprising the sequence of ELKSLNPRWDGE (SEQ ID NO:3) wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3

Further, the invention encompasses methods of treating a disorder in a mammal comprising administering to the mammal a therapeutic agent conjugated to an ADP comprising the sequence of SEQ ID NO:3 or a fragment or conservative variant thereof, that retains the albumin docking activity of a peptide of SEQ ID NO:3. The disorder may advantageously be treated by an agent conjugated to an ADP comprising the sequence of ELKSLNPRWDGE (SEQ ID NO:3) wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3. The disorder may be any disorder to which a drug may be supplied. The disorder may include but is not limited to a disorder selected from the group consisting of a cardiovascular disease, a cancer, an inflammatory disease, and an autoimmune disease. In certain embodiments, the disorder is a cancer and the agent is a chemotherapeutic agent.

Also described herein is a method of delivering a therapeutic agent to the subendothelial space in an organ in a mammal, comprising administering to the mammal with a therapeutic composition comprising the therapeutic agent conjugated to an ADP comprising the sequence of SEQ ID NO:3 or a fragment or conservative variant thereof, that retains the albumin docking activity of a peptide of SEQ ID NO:3, wherein the uptake of the therapeutic enzyme into the subendothelial space is mediated through caveolae on the surface of the cell. In specific embodiments, the therapeutic agent is conjugated to an ADP sequence of any of the sequences of SEQ ID N:3 or SEQ ID NO:5 through 36 or a fragment or conservative variant of any of the sequence of SEQ ID NO:3 or SEQ ID NO:5 through 36 that retains the albumin docking activity of a peptide of SEQ ID NO:3

Further aspects of the invention encompass methods of treating a disease comprising delivering a therapeutic agent to the sub-endothelial space, wherein the delivering comprises administering a therapeutic composition comprising an ADP comprising the sequence of SEQ ID NO:2 or a fragment or conservative variant thereof, that retains the albumin docking activity of a peptide of SEQ ID NO:2, conjugated to a therapeutic agent used in the treatment of the cardiovascular disease, in an amount effective to ameliorate the symptoms of the disease. Preferably, the disease is a cardiovascular disease. In specific embodiments, the subject being treated is a human, however, it should be understood that the compositions also may be useful in veterinary medicine.

Other embodiments contemplate the treatment of a disease of the CNS in which the transcytosis of the ADP facilitates the transport of the therapeutic agent across the blood brain barrier. Disorders of the CNS are well known to those of skill in the art. Exemplary such disorders include, but are not limited to, Alzheimer's Disease, Parkinson's Disease, multiple sclerosis, and amylotrophic lateral sclerosis, and a CNS neoplasia.

Other aspects of the present invention describe pharmaceutical compositions that comprise an ADP as described herein in combination with a pharmaceutically acceptable carrier, diluent or excipient. Such compositions may be used in the treatment of a disorder in need of the ADP, typically, such a disorder is one in which the inhibition of myeloperoxidase is desired. The disorder may be a cardiovascular disorder or other disorder mediated by an excessive amount or activity of MPO, e.g., an inflammatory disease. Alternative pharmaceutical compositions of the invention comprise a compound that comprises an ADP conjugated to an agent of interest in combination with a pharmaceutically acceptable carrier, diluent or excipient.

The invention also contemplates compositions that comprise compounds of the invention for use in the treatment of a disorder in need of the therapeutic agent of the compound.

Another aspect of the present invention encompasses methods of treating an inflammatory disorder in an animal comprising administering to the animal a composition comprising an ADP comprising the sequence of SEQ ID NO:3 or a fragment or conservative variant thereof, that retains the albumin docking property of a peptide of SEQ ID NO:3 in amount effective to treat the inflammatory disorder. The peptide may have the sequence of SEQ ID NO: 3, or any of the sequences of SEQ ID NO:5 through 36 or any conservative variant or fragment of such a peptide that retains the albumin docking property of a peptide of SEQ ID NO:3. The inflammatory disorder is preferably an inflammatory disorder caused by an excessive production of myeloperoxidase. The inflammatory disorder may be a chronic inflammatory disorder or it may be an acute inflammatory disorder.

Other aspects of the invention comprise inhibiting tyrosine nitration in a biological sample comprising contacting the biological sample with an ADP comprising the sequence of SEQ ID NO:3 or a fragment or conservative variant thereof, that retains the albumin docking property of a peptide of SEQ ID NO:3, wherein the ADP inhibits MPO activation of the tyrosine nitration. In such embodiments, the biological sample may be contacted with the ADP in vitro in cell culture. Alternatively, the biological sample is contacted with the ADP in vivo. Preferably, the biological sample is one which comprises endothelial cells. In specific embodiments, the method uses an ADP that consists of the sequence of SEQ ID NO:3, or any of the SEQ ID NO:5 through 36 or any conservative variant or fragment thereof that retains the albumin docking activity of SEQ ID NO:3.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 1A) Purification of proteins using HSA-affinity column. Proteins eluted from HSA-affinity column were subjected to SDS-PAGE and stained with CBB-R250. Lane 1, human lung homogenate proteins; Lane 2, proteins eluted from HSA-affinity column. FIG. 1B) Identification of proteins by MALDI-MS. Schematics of the identified MPO sequences are shown (GenBank accession number P05164). The mass of 17 tryptic peptides to mass of amino acids 295-303, 367-375, 395-406, 405-422, 441-448, 460-474, 472-482, 488-500, 498-512, 512-530, 536-549, 559-572, 578-591, 590-604, 691-702, 701-715, 714-726 were obtained from 60 kDa (MPO-HC). In the case of 80 kDa protein, the mass of amino acids sequences obtained were same as 60 kDa except that two additional mass of amino acids 173-193 and 218-228. LC, light chain; HC, heavy chain. FIG. 1C) MPO sequence homology with the HSA-binding domain bacterial proteins. FIG. 1D) Binding of MPO peptides with $^{125}$I-HSA. Peptides were immobilized on nitrocellulose membranes at the indicated concentrations. The binding of $^{125}$I-HSA to the peptides was determined as described in Example 1. FIG. 1E) Effects of soluble MPO-WT and MPO-MT peptides on the binding of $^{125}$I-HSA to immobilized MPO-WT peptide. MPO-WT peptide (10 nmoles) was spotted on the membranes (15×15 mm). Nonspecific binding was blocked and then incubated with 1 ml of $^{125}$I-HSA (0.3 PM) for 2 h at 22° C. in the presence of varying concentrations of either WT-peptide or MT-peptide. Other details were described in Example 1. The experiment was repeated 3× in triplicate. *, indicates the difference from control (in the absence of soluble peptide) ($p<0.05$). **, ($p<0.001$).

FIG. 2B: Effects of albumin on time course transendothelial transport of MPO. BLMVEC grown on microporous Transwell filters were used to determine transendothelial transport of MPO as described in Example 1. To study the methyl-B-cyclodextrin (CD) effect, luminal chamber was incubated with 5.0 mM CD for 20 min prior to measuring $^{125}$I-MPO permeability. The results are shown as mean±S.E. of four separate experiments made in triplicate. *, indicates difference from control (γ-globulin) group or CD-treated group ($p<0.001$). FIG. 2C: Albumin increases transendothelial $^{125}$I-MPO permeability. Experimental procedure was as described in FIG. 2B. The transendothelial $^{125}$I-MPO clearance rate was calculated as described (24, 27). *, indicates difference from control or CD-treated group ($p<0.001$). The results are shown as mean±S.E. of four separate experiments made in triplicate.

FIG. 3B: Albumin induces the co-localization of MPO with cholera toxin subunit B (CTB) in endothelial cells. BLMVEC were grown as described in FIG. 3A. Cells were incubated with Alexa 488-CTB; (20 ug/ml), MPO (25 nM), and BSA (1 mg/ml) in buffer C for 30 min at 37° C. After this, cells were washed, fixed, permeabilized, and stained with anti-MPO Ab and AlexaA594 labeled secondary antibody. Cells were visualized by confocal microscopy after mounting. Confocal images of CTB (green-left panel) and anti-MPO Ab staining (red-middle panel) in vesicles are shown. Overlay of MPO staining and Alexa-488 CTB uptake shows marked colocalization in the merged image (right-panel). FIG. 3C: Vesicular staining pattern and co-localization of albumin MPO complex with cholera toxin subunit B. High resolution z-stacks of images combined with orthogonal and projection view image displays were used to co-localize MPO internalized in the presence of albumin with the endocytosed CTB (see FIG. 3B). There was marked merging in vesicles in the YZ projection image (far left panel) and single frame (X-Y) or single line (Y-Z and X-Z) images (left panel) observed in the presence of albumin compared to the green CTB-positive/MPO negative vesicles observed in the absence albumin (right and far right panels). FIG. 3D: Cyclodextrin prevents albumin-induced endocytosis of MPO. BLMVEC were grown as described in FIG. 3A. Cells were incubated with 5 mM CD in buffer C for 20 min at 37° C. Cells were then incubated with 25 nM MPO plus BSA (1 mg/ml) in buffer C for 30 min at 37° C. After this incubation, cells were stained with anti-MPO Ab as described above. Confocal images were obtained at the mid-plane of the cell to visualize the internalized vesicles. CD treatment prevented the endocytosis of MPO in BLMVEC. FIG. 3E: Internalized MPO co-localizes with caveolin-1 in endothelial cells. BLMVEC were grown and incubated with serum-free medium as described in FIG. 3A. Cells were incubated with 25 nM MPO in the presence and absence of BSA (1 mg/ml) for 30 min at 37° C. The cells were then fixed and stained with rabbit anti-MPO Ab and anti-caveolin-1 mAb (1 µg/ml) overnight at 4° C. After washing, the cells were incubated with goat anti-rabbit Alexa 594 or anti-mouse Alexa 488 labeled secondary Ab for 1 h at 22° C. Confocal images were acquired using identical settings. Note the increase in MPO uptake in the presence of albumin and the colocalization of the internalized MPO with caveolin-1.

DESCRIPTION OF THE PREFERRED EMBODIMENTS

In vitro high throughput screening methods have identified numerous promising candidates for the therapeutic intervention of disease states. However, even if a drug candidate is identified as particularly suitable for a given therapy, the mass use of such an agent often is hindered by the lack of bioavailability of the drug to the target site from the bloodstream. More particularly, it is well-established that macromolecular therapeutic agents need to penetrate the epithelial and/or endothelial barriers to access the intended target sites of pharmacological action, namely, the cells inside the tissue (Jain, Nat. Med. 4, 655-657, 1998; Miller and Vile, FASEB J. 9, 190-199, 1995; Thrush et al., Annu. Rev. Immunol. 14, 49-71, 1995; Tomlinson, Adv. Drug Delivery Rev. 1, 87-198, 1987). However, such penetration is often, at best, inefficient of the therapeutic agent has not be modified to enhance its uptake.

One method of transporting an active agent across the endothelial barrier is to couple or conjugate the active agent to a second molecule (a "carrier"), which is a peptide or non-proteinaceous moiety selected for its ability to penetrate the barrier and transport the active agent across the endothelial layer into the cells of choice.

The present invention for the first time identifies particular sequences of myeloperoxidase (MPO) that serve as albumin docking proteins (ADPs). More particularly, MPO purified from human lung tissue was shown to specifically interact with human serum albumin (HSA). The positive charge on MPO-HC residues 425-454 was required for the MPO binding to HSA. Further, it is shown herein that MPO interaction with albumin induced the transcytosis of MPO via caveolae in endothelial cells. Thus, in certain embodiments, the methods and compositions described herein provide new methods and compositions for the delivery of an active agent to a cell.

A further aspect of the invention is directed to the inhibition of MPO-mediated responses using compositions comprising or related to the ADP sequence. Such compositions are likely to act as competitive inhibitors of the action of MPO.

Methods and compositions for exploiting the above findings are described in further detail herein below.

MPO-Uptake is Mediated through Albumen Binding

Figure 1A:
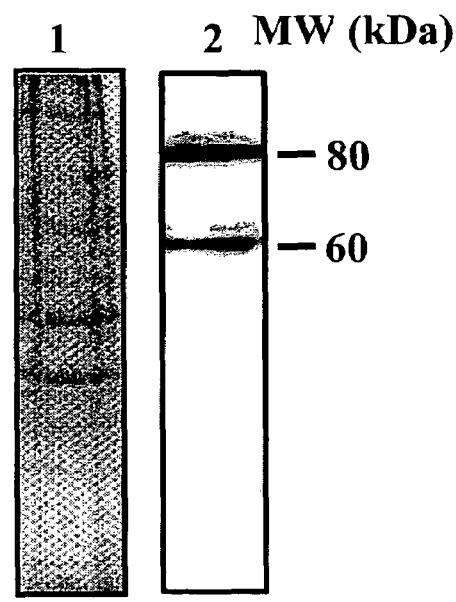
FIG. 1A-FIG. 1E: Identification of MPO as an albumin-binding protein.
Figure 1B:
Figure 1C:
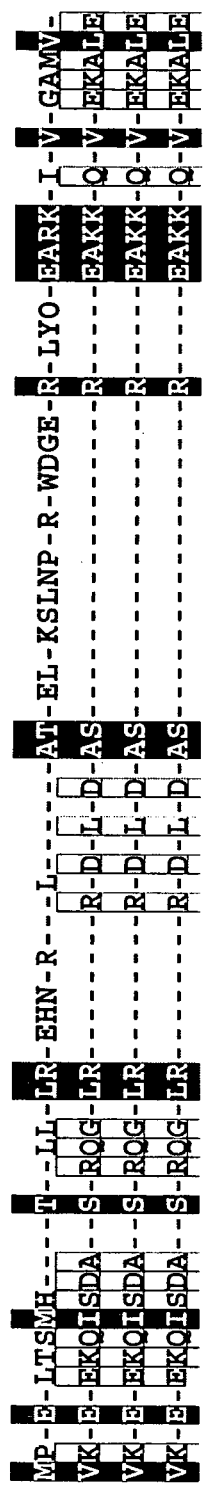

Serum albumin, a monomeric protein containing 17 disulfide bridges, consists of three homologous domains (I-III) (23), is an anionic protein at pH of 7.4 with net charges for domains I, II, and III of −9, −8, and +2, respectively, for human albumin. The data discussed in further detail in the examples below show that MPO has a specific albumin binding sequence. More particularly, it is shown herein that residues 409 to 454 (SEQ ID NO:36) of MPO-HC, a 60 kDa MW protein isolated from human lung tissue, has a high homology with the HSA-docking sequence identified in bacterial proteins (Retnoningrum and Cleary, Infect. Immun. 62:2387-2394, 1994). Further, the data show that HSA binds with high affinity to the MPO-HC peptide sequence 425-454 (MPO-WT-peptide; SEQ ID NO:20). HSA-MPO binding ability of these peptides was abolished by altering the charge on this sequence by substituting G for R and K. The albumin-binding domain in bacterial proteins showed binding only to HSA and failed to interact with BSA (Retnoningrum and Cleary, Infect. Immun. 62:2387-2394, 1994). However, the sequences of the present invention bind to both bovine serum albumin (BSA) and rat serum albumin (RSA) as effectively as HSA. In specific embodiments it is contemplated that the sequence ELK-SLNPRWDGE (SEQ ID NO:3; FIG. 1C) binds to multiple albumin forms. The EARKIV motif (SEQ ID NO:4) is conserved in MPO-HC and bacterial proteins containing the albumin- binding domain (Retnoningrum and Cleary, Infect. Immun. 62:2387-2394, 1994). $^{125}$I-HSA binding to the EAR-KIV peptide failed to bind HSA failed to bind to the EARKIV, suggesting that the flanking sequence is critical for the MPO interaction with albumin.

Albumin with plasma concentration ranging from 400 to 675 pM constitutes greater than 60% of plasma protein in human blood. Albumin at very low concentrations (ca. 0.05 g/100 ml) maintains the endothelial barrier integrity by interactions with cell surface and extracellular matrix components. Studies have shown that caveolae-mediated vesicular transport of albumin is the primary mode of transendothelial albumin permeability (Tiruppathi et al., J. Biol. Chem., 272: 25968-25975 (1997); Minshall et al., J. Cell Biol., 150:1057-1069 (2000); Vogel et al., Am. J. Physiol Lung Cell Mol Physiol., 281:L1512-L1522 (2001); John et al., Am. J. Physiol. Lung Cell Mol. Physiol., 284:L187-L196 (2003)). The ABPs localized in caveolae play an important role in the mechanism of transcellular transport of albumin in endothelial cells (Tiruppathi et al., J. Biol. Chem., 272:25968-25975 (1997); Minshall et al., J. Cell Biol., 150:1057-1069 (2000); Vogel et al., Am. J. Physiol Lung Cell Mol Physiol., 281: L1512-L1522 (2001); John et al., Am. J. Physiol. Lung Cell Mol. Physiol., 284:L187-L196 (2003)) and intact microvessels (Vogel et al., Am. J. Physiol. Lung Cell Mol. Physiol., 281:L1512-L1522 (2001)). Signaling via Src tyrosine kinase phosphorylation is critical in the mechanism of transcellular transport of albumin and fluid phase solutes carried with albumin in vesicles (Tiruppathi et al., J. Biol. Chem., 272: 25968-25975 (1997)).

The release of MPO from polymorphonuclear neutrophils (PMNs), catalyses the conversion of $H_2O_2$ to HOCl, a potent antibacterial agent (Winterbourn et al., Curr. Opin. Hematol. 7:53-58, 2000). MPO transport across the endothelial cell barrier and its accumulation in the sub-endothelium is crucial in oxidative events since MPO is an enzymatic source of NO-derived oxidants and nitrotyrosine formation (Abu-Soud et al., J. Biol. Chem., 275:37524-37532 (2000); Leeuwenburgh et al., J. Biol. Chem., 272:1433-1436 (1997); Shishehbor et al., JAMA, 289:1675-1680 (2003); Lamb et al., Cril. Care Med., 27:1738-1744 (1999); Van Der Vijet et al., Am. J. Physiol. Lung Cell Mol. Physiol., 279:1,537-1,546 (2000); Brennan et al., J. Biol. Chem., 277:17415-17427 (2002)). Recent studies showed that MPO levels in plasma provide a useful measure of the severity of acute coronary syndromes (Daugherty et al., J. Clin. Invest., 94:437-444 (1994); Brennan et al., N. Eng. J. Med., 349:1595-1604 (2003)). MPO levels in the plasma increased (ranging from pM to nM) in patients with different inflammatory pathologies (Brennan et al., N. Eng. J. Med., 349:1595-1604 (2003); Baldus et al., Circulation, 108:14401445 (2003); Zhang et al., JAMA, 286: 2136-2142 (2001)).

These deleterious effects of MPO are caused when MPO is transported across the endothelial barrier through interaction with albumin. The data described in the examples show that $^{125}$I-MPO binding to the endothelial cell surface increased in the presence of albumin and albumin induced the transendothelial transport of MPO. MPO transport resulting from its interaction with albumin was dependent on the albumin concentration and this transport was saturable. These findings are consistent with the transport of albumin occurring through a nonhydraulic transcellular pathway that requires albumin binding to endothelial cell surface ABPs such as gp60 (Tiruppathi et al., J. Biol. Chem., 272:25968-25975 (1997); Minshall et al., J. Cell Biol., 150:1057-1069 (2000); Vogel et al., Am. J. Physiol. Lung Cell. Mol. Physiol., 281:L1512-L1522 (2001); John et al., Am. J. Physiol. Lung Cell Mol. Physiol., 284:L187-L196 (2003)). Thus, the results described herein show that the albumin-MPO interaction induces MPO transport via a transcellular pathway dependent on albumin binding to endothelia cells. Since plasma albumin concentration is 2000- to 5000-fold molar greater MPO, the generation of MPO and its interaction with plasma albumin is likely to be the dominant method of MPO transport across the endothelial barrier.

Figure 4:
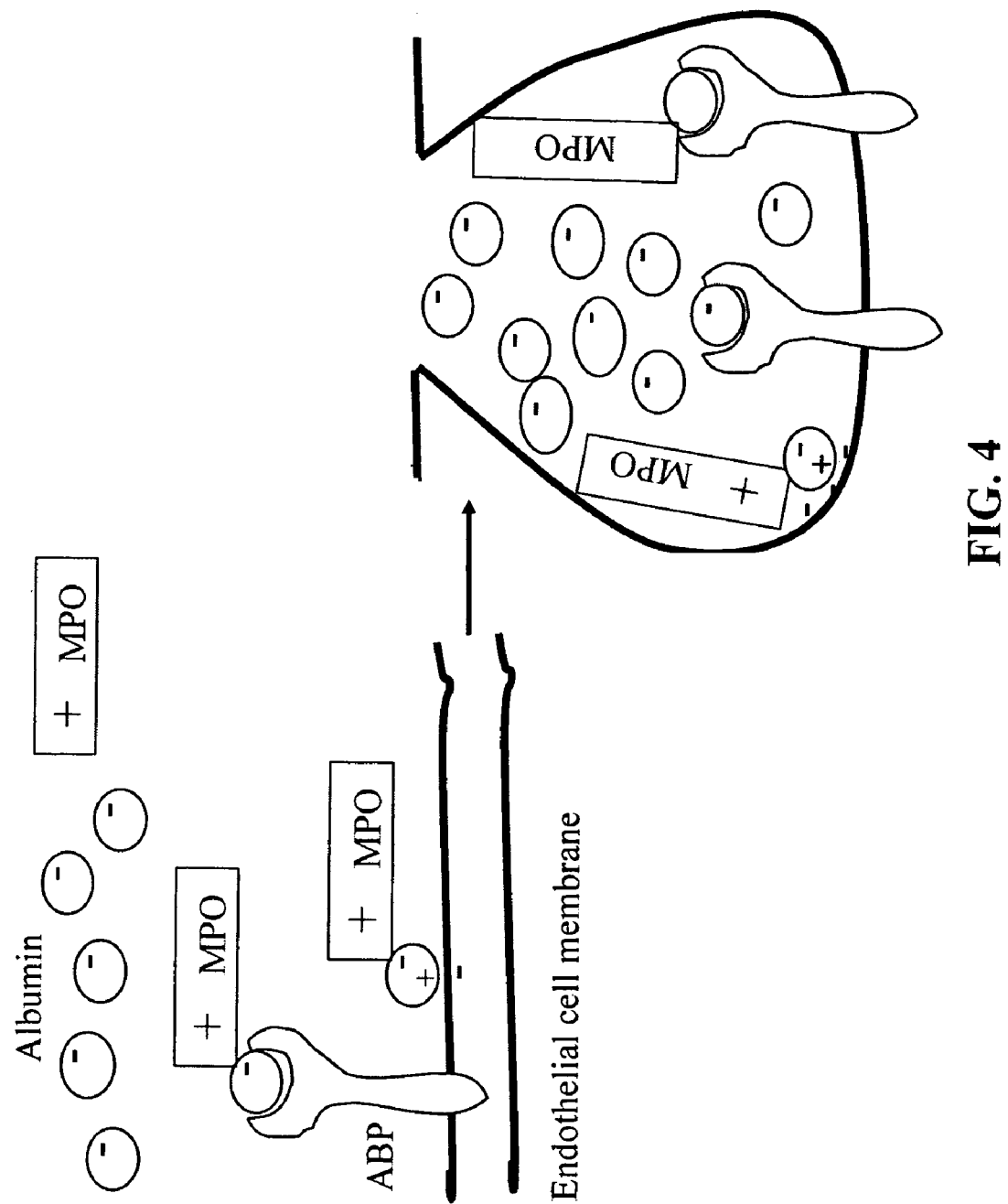
FIG. 4: Albumin-induced transcytosis of MPO in endothelial cells. Binding of positively charged domain of MPO to albumin in plasma promotes MPO-albumin interaction and binding to endothelial plasmalemma in caveolae via ABP (e.g., gp60). Albumin plays an essential role in the mechanism of MPO transcytosis.

Caveolae are the non-clathrin coated pits in endothelial cells responsible for transcytosis (Carver et al., Nature Reviews Cancer, 3:571-581 (2003)). When the organization of caveolae was disturbed by treating endothelial cells with methyl-β-cyclodextrin (CD), the albumin-induced increase in the transendothelial $^{125}$I-MPO permeability was prevented. Further, in the absence of albumin, MPO localized at the cell surface; however, in the presence of albumin, MPO was rapidly internalized and co-localized with the albumin-containing vesicles. In addition, in the presence of albumin, the internalized MPO co-localized with cholera toxin subunit B (CTB), indicating that caveolae mediated endocytosis of albumin induces the uptake and transport of MPO. MPO and caveolin-1, the structural protein of caveolae, (Carver and Schnitzer, Nature Reviews Cancer. 3:571-581, 2003) co-localized in endothelial cells after incubation with albumin; however, there was little MPO co-localized with caveolin-1 in the absence of albumin. These, studies show a novel model of MPO transport across the endothelial barrier (FIG. 4). Albumin interaction with the ABPs such as gp60 localized in caveolae induces vesicle trafficking across the endothelium (Tiruppathi et al., J. Biol. Chem. 272:25968-25975 (1997); Minshall et al., J. Cell Biol., 150:1057-1069 (2000); Vogel et al., Am. J. Physiol. Lung Cell. Mol. Physiol., 281:L1512-L1522 (2001); John et al., Am. J. Physiol. Lung Cell Mol. Physiol., 284:L187-L196 (2003)). Since MPO interacts with albumin by a specific binding domain, albumin enables the transcytosis of MPO via caveolae. The accumulation of MPO in the sub-endothelial space as regulated by specific MPO interaction with albumin may promote extracellular matrix remodeling by generating NO-derived reactive species and nitrotyrosine formation, and thereby interfere with endothelial integrity.

The above findings may be exploited in a variety of different aspects. Initially, MPO-based sequences may be conjugated or otherwise associated with active agents to effect the delivery of those agents to a target site via transcytosis. In other embodiments, fragments of MPO may be prepared that competitively inhibit the uptake of MPO in various disease states that are mediated by MPO. Specific such fragments may be formulated as therapeutic compositions for the treatment of diseases that are caused by increased MPO levels. These and other aspects of the invention are described in further detail herein below.

MPO and MPO Fragments

As discussed above, the present invention provides compositions for the therapeutic intervention of a variety of disorders. Such compositions are generally divided into two categories. Firstly the compositions are based on specific MPO proteins or specific MPO protein fragments that have the ability to inhibit the uptake of wild-type MPO. The second category of therapeutic compositions are those that comprise a first portion that comprises at least the albumin docking protein (ADP) domain of MPO conjugated, or otherwise bound, to a second portion that comprises a therapeutic or other active agent that is to be delivered to a particular target site. The target site at which the agent may be delivered is limited only by the requirement that the target site has caveolae or other structures which facilitate the transcytosis of albumin because the delivery of the therapeutic or active agent will be mediated through the binding, or "docking" of the MPO-ADP sequence onto circulating albumin to transport of MPO-ADP across the endothelial layer. The MPO-ADP sequence along with the active agent conjugated thereto will be transported through transcytosis along with the albumin to which the conjugate is bound. The following section provides a description of the MPO sequences that may be used in therapeutic compositions either alone, or as conjugates with other active agents.

MPO is an enzyme first found in 1941 by Agner in animal leukocytes (Agner, Acta Physiol. Scand., 2, Suppl., 8, 1941). It is contained in large quantity together with lysozyme, in myelogenous white blood cells, especially in neutral multinuclear leukocytes and in monocytes, the content amounting up to 5% based on the weight of neutrophils. MPO is a heme protein synthesized during myeloid differentiation that constitutes the major component of neutrophil azurophilic granules. Produced as a single chain precursor, MPO is subsequently cleaved into a light and heavy chain. The mature myeloperoxidase is a tetramer composed of two light chains and 2 heavy chains. This enzyme produces hypohalous acids central to the microbicidal activity of neutrophils.

An exemplary sequence human MPO protein sequence is provided at GenBank Acc. No. NP_000241 (reproduced herein as SEQ ID NO:2, and encoded by a polynucleotide having a nucleic acid sequence of SEQ ID NO: 1, a sequence that is depicted in GenBank Acc. No. NM_000250). While in preferred embodiments, the MPO sequence used herein is derived from human MPO, it is contemplated that the sequence also may be derived from another mammalian source such as e.g., mouse (see e.g., mouse MPO precursor protein sequence at GenBank Acc. No. AAR99349 for the protein sequence and GenBank Acc. No. AY500847 coding region: 49 . . . 2205, for the related nucleic acid sequence; mature mouse MPO is found at GenBank Acc. No. NP_034954 and the related nucleic acid sequence is at GenBank Acc No. NM_010824). Other sequences for MPO proteins are known to those of skill in the art. For example, additional disclosure of human MPO sequence may be found at U.S. Pat. No. 5,460,961 (incorporated herein by reference in its entirety); see also U.S. Pat. No. 5,985,272 for methods of producing human MPO by culturing prokaryotic and eukaryotic cells transformed by a vector for the expression of human MPO.

In the present invention it has been found that a sequence that comprises residues 425-454 of MPO is sufficient for the binding of MPO to HSA. This fragment of MPO comprises the sequence: RLATELKSLNPRWDGERLYQEARKIVGAMV (SEQ ID NO:20), however, further analyses revealed that a sequence of ELKSLNPRWDGE (SEQ ID NO:3) is able to bind to albumin from any of a variety of sources, e.g., human, porcine, murine, etc. Thus, it is contemplated that for particular embodiments, the conjugates of the present invention comprise all of part of the sequence ELKSLNPRWDGE (SEQ ID NO:3). In specific examples, it was shown that the sequence EARKIV is conserved in MPO as well as a variety of bacterial albumin binding proteins. It is contemplated that residues longer than EARKIV comprising part or all of the flanking sequence will be useful as fragments for the present invention. It is particularly contemplated that the fragments useful herein will include: ERLYQEARKIVGAMV (SEQ ID NO:5); GERLYQEARKIVGAMV (SEQ ID NO:6); DGERLYQEARKIVGAMV (SEQ ID NO:7); WDGERLYQEARKIVGAMV (SEQ ID NO:8); RWDGERLYQEARKIVGAMV (SEQ ID NO:9); PRWDGERLYQEARKIVGAMV (SEQ ID NO:10); NPRWDGERLYQEARKIVGAMV (SEQ ID NO:11); LNPRWDGERLYQEARKIVGAMV (SEQ ID NO:12); SLNPRWDGERLYQEARKIVGAMV (SEQ ID NO:13); KSLNPRWDGERLYQEARKIVGAMV (SEQ ID NO:14); LKSLNPRWDGERLYQEARKIVGAMV (SEQ ID NO:15); ELKSLNPRWDGERLYQEARKIVGAMV (SEQ ID NO:16); TELKSLNPRWDGERLYQEARKIVGAMV (SEQ ID NO:17); ATELKSLNPRWDGERLYQEARKIVGAMV (SEQ ID NO:18); LATELKSLNPRWDGERLYQEARKIVGAMV (SEQ ID NO:19); RLATELKSLNPRWDGERLYQEARKIVGAMV (SEQ ID NO:20) NRLATELKSLNPRWDGERLYQEARKIVGAMV (SEQ ID NO:21); HNRLATELKSLNPRWDGERLYQEARKIVGAMV (SEQ ID NO:22); EHNRLATELKSLNPRWDGERLYQEARKIVGAMV (SEQ ID NO:23); REHNRLATELKSLNPRWDGERLYQEARKIVGAMV (SEQ ID NO:24); LREHNRLATELKSLNPRWDGERLYQEARKIVGAMV (SEQ ID NO:25); LLREHNRLATELKSLNPRWDGERLYQEARKIVGAMV (SEQ ID NO:26); LLLREHNRLATELKSLNPRWDGERLYQEARKIVGAMV (SEQ ID NO:27); TLLLREHNRLATELKSLNPRWDGERLYQEARKIVGAMV (SEQ ID NO:28); HTLLLREHNRLATELKSLNPRWDGERLYQEARKIVGAMV (SEQ ID NO:29); MHTLLLREHNRLATELKSLNPRWDGERLYQEARKIVGAMV (SEQ ID NO:30); SMHTLLLREHNRLATELKSLNPRWDGERLYQEARKIVGAMV (SEQ ID NO:31); TSMHTLLLREHNRLATELKSLNPRWDGERLYQEARKIVGAMV (SEQ ID NO:32); LTSMHTLLLREHNRLATELKSLNPRWDGERLYQEARKIVGAMV (SEQ ID NO:33); ELTSMHTLLLREHNRLATELKSLNPRWDGERLYQEARKIVGAMV (SEQ ID NO:34); PELTSMHTLLLREHNRLATELKSLNPRWDGERLYQEARKIVGAMV (SEQ ID NO:35) and MPELTSMHTLLLREHNRLATELKSLNPRWDGERLYQEARKIVGAMV (SEQ ID NO:36). In addition, variants of the sequence of SEQ ID NO:3, and SEQ ID NO:5 through SEQ ID NO:36 that retain an overall positive charge are also contemplated to be particularly useful as albumin binding peptides that will serve to dock to the albumin protein. Such peptides can be readily synthesized using techniques well known to those of skill in the art. Other fragments of the sequence of SEQ ID NO:2 that comprise all or part of any of a sequence of SEQ ID NO:36, and an overall positive charge also will be useful in the present invention. For example, fragments of a sequence of SEQ ID NO:2 that comprise at least a segment that consist of the residues of sequence of SEQ ID NO:3 and contain an overall positive charge will also be particularly useful.

The peptides used in the present invention either alone, or as part of a conjugate may be peptides of 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, or more amino acid residues in length. The entire MPO protein is 745 amino acids in length. The fragments that will be useful may be of any length from 6 amino acids in length to about 700 amino acids in length. While each specific integer from 50 to 745 has not been explicitly recited above for reasons of clarity, it should be understood that any fragment of the 745 MPO protein that retains a capacity to bind to albumin and thereby become transported through the cellular transcytotic pathway that transports albumin is contemplated to be within the scope of the present invention.

In those embodiments in which the MPO peptide will be delivered as a therapeutic agent itself (rather than as a "carrier" in a conjugate carrying an active agent for transcytosis), it is contemplated that the MPO derived proteins/peptides may be modified to enhance their uptake, circulation, and/or other modifications to render the peptides more therapeutically effective. In certain embodiments, the conjugates also may be thus modified. Thus, it may be desirable to prevent the degradation of the peptides in order to prolong the effects thereof, and as, such prolong the effects of the MPO as a competitive inhibitor of wild-type MPO in the circulation of an individual suffering from a disorder caused by or manifesting in an elevated MPO concentration. This may be achieved through the use of non-hydrolyzable peptide bonds, which are known in the art, along with procedures for synthesis of peptides containing such bonds. Non-hydrolyzable bonds include —[$CH_2NH$]— reduced amide peptide bonds, —[$COCH_2$]— ketomethylene peptide bonds, —[$CH(CN)$ $NH$]— (cyanomethylene)amino peptide bonds, —[$CH_2$ $CH(OH)$]— hydroxyethylene peptide bonds, —[$CH_2O$]— peptide bonds, and —[$CH_2S$]— thiomethylene peptide bonds (see e.g., U.S. Pat. No. 6,172,043).

MPO-derived proteins useful in the invention can be linear, or maybe circular or cyclized by natural or synthetic means. For example, disulfide bonds between cysteine residues may cyclize a peptide sequence. Bifunctional reagents can be used to provide a linkage between two or more amino acids of a peptide. Other methods for cyclization of peptides, such as those described by Anwer et al. (Int. J Pep. Protein Res. 36:392-399, 1990) and Rivera—Baeza et al. (Neuropeptides 30:327-333, 1996) are also known in the art.

Furthermore, nonpeptide analogs of the MPO-derived proteins that provide a stabilized structure or lessened biodegradation, are also contemplated. Peptide mimetic analogs can be prepared based on a MPO peptide by replacing one or more amino acid residues of the protein of interest by nonpeptide moieties. Preferably, the nonpeptide moieties permit the peptide to retain its natural confirmation, or stabilize a preferred, e.g., bioactive confirmation and an overall positive charge. One example of methods for preparation of nonpeptide mimetic analogs from peptides is described in Nachman et al., Regul. Pept. 57:359-370 (1995). The term "peptide" as used herein embraces nonpeptide analogs, mimetics and modified peptides.

The MPO derived proteins used in the therapeutic methods of the present invention may be modified in order to improve their therapeutic efficacy. Such modification of therapeutic compounds may be used to decrease toxicity, increase circulatory time, or modify biodistribution. A strategy for improving drug viability is the utilization of water-soluble polymers. Various water-soluble polymers have been shown to modify biodistribution, improve the mode of cellular uptake, change the permeability through physiological barriers, and modify the rate of clearance from the body. (Greenwald et al., Crit Rev Therap Drug Carrier Syst. 2000;17:101-161; Kopecek et al., J Controlled Release., 74:147-158, 2001). To achieve either a targeting or sustained-release effect, water-soluble polymers have been synthesized that contain drug moieties as terminal groups, as part of the backbone, or as pendent groups on the polymer chain.

Polyethylene glycol (PEG), has been widely used as a drug carrier, given its high degree of biocompatibility and ease of modification. Harris et al., Clin Pharmacokinet. 2001;40(7): 539-51 Attachment to various drugs, proteins, and liposomes has been shown to improve residence time and decrease toxicity. (Greenwald et al., Crit Rev Therap Drug Carrier Syst. 2000;17:101-161; Zalipsky et al., Bioconjug Chem. 1997;8: 111-118). PEG can be coupled to active agents through the hydroxyl groups at the ends of the chain and via other chemical methods; however, PEG itself is limited to at most two active agents per molecule. In a different approach, copolymers of PEG and amino acids were explored as novel biomaterials which would retain the biocompatibility properties of PEG, but which would have the added advantage of numerous attachment points per molecule (providing greater drug loading), and which could be synthetically designed to suit a variety of applications (Nathan et al., Macromolecules. 1992; 25:4476-4484; Nathan et al., Bioconj Chem. 1993;4:54-62).

Those of skill in the art are aware of PEGylation techniques for the effective modification of drugs. For example, drug delivery polymers that consist of alternating polymers of PEG and tri-functional monomers such as lysine have been used by VectraMed (Plainsboro, N.J.). The PEG chains (typically 2000 daltons or less) are linked to the a- and e-amino groups of lysine through stable urethane linkages. Such copolymers retain the desirable properties of PEG, while providing reactive pendent groups (the carboxylic acid groups of lysine) at strictly controlled and predetermined intervals along the polymer chain. The reactive pendent groups can be used for derivatization, cross-linking, or conjugation with other molecules. These polymers are useful in producing stable, long-circulating pro-drugs by varying the molecular weight of the polymer, the molecular weight of the PEG segments, and the cleavable linkage between the drug and the polymer. The molecular weight of the PEG segments affects the spacing of the drug/linking group complex and the amount of drug per molecular weight of conjugate (smaller PEG segments provides greater drug loading). In general, increasing the overall molecular weight of the block co-polymer conjugate will increase the circulatory half-life of the conjugate. Nevertheless, the conjugate must either be readily degradable or have a molecular weight below the threshold-limiting glomular filtration (e.g., less than 45 kDa). Thus, PEgylated MPO derived peptides of the invention should preferably be in the range of between 20 and 35 kDa in molecular weight.

In addition, to the polymer backbone being important in maintaining circulatory half-life, and biodistribution, linkers may be used to maintain the therapeutic agent in a pro-drug form until released from the backbone polymer by a specific trigger, typically enzyme activity in the targeted tissue. For example, this type of tissue activated drug delivery is particularly useful where delivery to a specific site of biodistribution is required and the therapeutic agent is released at or near the site of pathology. Linking group libraries for use in activated drug delivery are known to those of skill in the art and may be based on enzyme kinetics, prevalence of active enzyme, and cleavage specificity of the selected disease-specific enzymes (see e.g., technologies of established by VectraMed, Plainsboro, N.J.). Such linkers may be used in modifying the MPO derived proteins described herein for therapeutic delivery.

Methods of Making and Isolating MPO Derived Peptides

The present invention provides MPO-based proteins and peptides either as medicaments themselves, or for use in conjugating to other therapeutic or active agents whose delivery to a particular site is desired and will be facilitated by transcytosis when the MPO portion of the therapeutic conjugate becomes bound to circulating albumin and the albumin is transported into the subendothelial space via transcytosis. Such MPO proteins or peptides may be produced by conventional automated peptide synthesis methods or by recombinant expression. General principles for designing and making proteins are well known to those of skill in the art.

A. Automated Solid-Phase Peptide Synthesis

The peptides or indeed even the full length MPO can be synthesized in solution or on a solid support in accordance with conventional techniques. The peptides can be prepared from a variety of synthetic or enzymatic schemes, which are well known in the art. Where short peptides are desired, such peptides are prepared using automated peptide synthesis in solution or on a solid support in accordance with conventional techniques. Various automatic synthesizers are commercially available and are used in accordance with known protocols. See, for example, Stewart and Young, Solid Phase Peptide Synthesis, 2d. ed., Pierce Chemical Co., (1984); Tam et al., J. Am. Chem. Soc., 105:6442, (1983); Merrifield, Science, 232: 341-347, (1986); and Barany and Merrifield, The Peptides, Gross and Meienhofer, eds, Academic Press, New York, 1-284, (1979); Fields, (1997) Solid-Phase Peptide Synthesis. Academic Press, San Diego.); Andersson et al., Large-scale synthesis of peptides. Biopolymers (Pept. Sci. ), 55, 227-250 (2000); Burgess et al., DiSSiMiL: Diverse Small Size Mini-Libraries applied to simple and rapid epitope mapping of a monoclonal antibody. J. Pept. Res., 57, 68-76, (2001); Peptides for the New Millennium, Fields, J. P. Tam & G. Barany (Eds.), Kluwer Academic Publisher, Dordrecht. Numerous other documents teaching solid phase synthesis of peptides are known to those of skill in the art and may be used to synthesis epitope arrays from any allergen.

For example, the peptides are synthesized by solid-phase technology employing an exemplary peptide synthesizer such as a Model 433A from Applied Biosystems Inc. This instrument combines the FMOC chemistry with the HBTU activation to perform solid-phase peptide synthesis. Synthesis starts with the C-terminal amino acid. Amino acids are then added one at a time till the N-terminus is reached. Three steps are repeated each time an amino acid is added. Initially, there is deprotection of the N-terminal amino acid of the peptide bound to the resin. The second step involves activation and addition of the next amino acid and the third step involves deprotection of the new N-terminal amino acid. In between each step there are washing steps. This type of synthesizer is capable of monitoring the deprotection and coupling steps.

At the end of the synthesis the protected peptide and the resin are collected, the peptide is then cleaved from the resin and the side-chain protection groups are removed from the peptide. Both the cleavage and deprotection reactions are typically carried out in the presence of 90% TFA, 5% thioanisole and 2.5% ethanedithiol. After the peptide is separated from the resin, e.g., by filtration through glass wool, the peptide is precipitated in the presence of MTBE (methyl t-butyl ether). Diethyl ether is used in the case of very hydrophobic peptides. The peptide is then washed a plurality of times with MTBE in order to remove the protection groups and to neutralize any leftover acidity. The purity of the peptide is further monitored by mass spectrometry and in some case by amino acid analysis and sequencing.

The peptides also may be modified, and such modifications may be carried out on the synthesizer with very minor interventions. An amide could be added at the C-terminus of the peptide. An acetyl group could be added to the N-terminus. Biotin, stearate and other modifications could also be added to the N-terminus.

The purity of any given peptide, generated through automated peptide synthesis or through recombinant methods, is typically determined using reverse phase HPLC analysis. Chemical authenticity of each peptide is established by any method well known to those of skill in the art. In certain embodiments, the authenticity is established by mass spectrometry. Additionally, the peptides also are quantified using amino acid analysis in which microwave hydrolyses are conducted. In one aspect, such analyses use a microwave oven such as the CEM Corporation's MDS 2000 microwave oven. The peptide (approximately 2 µg protein) is contacted with e.g., 6 N HCl (Pierce Constant Boiling e.g., about 4 ml) with approximately 0.5% (volume to volume) phenol (Mallinckrodt). Prior to the hydrolysis, the samples are alternately evacuated and flushed with $N_2$. The protein hydrolysis is conducted using a two-stage process. During the first stage, the peptides are subjected to a reaction temperature of about 100° C. and held that temperature for 1 minute. Immediately after this step, the temperature is increased to 150° C. and held at that temperature for about 25 minutes. After cooling, the samples are dried and amino acid from the hydrolysed peptides samples are derivatized using 6-aminoquinolyl-N-hydroxysuccinimidyl carbamate to yield stable ureas that fluoresce at 395 nm (Waters AccQ Tag Chemistry Package). In certain aspects, the samples are analyzed by reverse phase HPLC and quantification is achieved using an enhanced integrator. Specific exemplary conditions for protein purification and quantification using mass spectrometry and HPLC are provided in Example 1. Such conditions may readily be adapted for large scale production and/or for purification of other peptides.

B. Recombinant Protein Production.

As an alternative to automated peptide synthesis, recombinant DNA technology may be employed wherein a nucleotide sequence which encodes a peptide of the invention is inserted into an expression vector, transformed or transfected into an appropriate host cell and cultivated under conditions suitable for expression as described herein below. Recombinant methods are especially preferred for producing longer polypeptides that comprise peptide sequences of the invention.

A variety of expression vector/host systems may be utilized to contain and express the peptide or protein coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), W138, BHK, HepG2, 3T3, RIN, MDCK, A549, PC12, K562 and 293 cells. Exemplary protocols for the recombinant expression of the peptide substrates or fusion polypeptides in bacteria, yeast and other invertebrates are known to those of skill in the art and a briefly described herein below.

Expression vectors for use in prokaryotic hosts generally comprise one or more phenotypic selectable marker genes. Such genes generally encode, e.g., a protein that confers antibiotic resistance or that supplies an auxotrophic requirement. A wide variety of such vectors are readily available from commercial sources. Examples include pSPORT vectors, pGEM vectors (Promega), pPROEX vectors (LTI, Bethesda, Md.), Bluescript vectors (Stratagene), pET vectors (Novagen) and pQE vectors (Qiagen). The DNA sequence encoding the given peptide substrate or fusion polypeptide is amplified by PCR and cloned into such a vector, for example, pGEX-3X (Pharmacia, Piscataway, N.J.) designed to produce a fusion protein comprising glutathione-S-transferase (GST), encoded by the vector, and a protein encoded by a DNA fragment inserted into the vector's cloning site. The primers for the PCR may be generated to include for example, an appropriate cleavage site. Treatment of the recombinant fusion protein with thrombin or factor Xa (Pharmacia, Piscataway, N.J.) is expected to cleave the fusion protein, releasing the substrate or substrate containing polypeptide from the GST portion. The pGEX-3X/MPO peptide construct is transformed into *E. coli* XL-1 Blue cells (Stratagene, La Jolla Calif.), and individual transformants were isolated and grown. Plasmid DNA from individual transformants is purified and partially sequenced using an automated sequencer to confirm the presence of the desired peptide or polypeptide encoding nucleic acid insert in the proper orientation. If the GST/MPO derived protein fusion protein is produced in bacteria as a soluble protein, it may be purified using the GST Purification Module (Pharmacia Biotech).

Alternatively, the DNA sequence encoding the predicted substrate containing fusion polypeptide may be cloned into a plasmid containing a desired promoter and, optionally, a leader sequence (see, e.g., Betteret al., Science, 240:1041-43, 1988). The sequence of this construct may be confirmed by automated sequencing. The plasmid is then transformed into *E. coli* using standard procedures employing $CaCl_2$ incubation and heat shock treatment of the bacteria (Sambrook et al., supra). The transformed bacteria are grown in LB medium supplemented with carbenicillin, and production of the expressed protein is induced by growth in a suitable medium. If present, the leader sequence will effect secretion of the mature MPO peptide or fusion protein and be cleaved during secretion.

The secreted recombinant protein is purified from the bacterial culture media by the method described herein throughout. Similar systems for the recombinant protein in yeast host cells are readily commercially available, e.g., the Pichia Expression System (Invitrogen, San Diego, Calif.), following the manufacturer's instructions. Another alternative recombinant production may be achieved using an insect system. Insect systems for protein expression are well known to those of skill in the art. In one such system, Autographa californica nuclear polyhedrosis virus (AcNPV) is used as a vector to express foreign genes in *Spodoptera frugiperda* cells or in *Trichoplusia larvae*. The MPO coding sequence is cloned into a nonessential region of the virus, such as the polyhedrin gene, and placed under control of the polyhedrin promoter. Successful insertion of MPO will render the polyhedrin gene inactive and produce recombinant virus lacking coat protein coat. The recombinant viruses are then used to infect *S. frugiperda* cells or *Trichoplusia larvae* in which the MPO is expressed (Smith et al., J Virol 46: 584, 1983; Engelhard E K et al., Proc Nat Acad Sci 91: 3224-7, 1994).

Mammalian host systems for the expression of recombinant proteins also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, and the like have specific cellular machinery and characteristic mechanisms for such post-translational activities and may be chosen to ensure the correct modification and processing of the introduced, foreign protein.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection and its presence allows growth and recovery of cells which successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, which confers resistance to methotrexate; gpt, which confers resistance to mycophenolic acid; neo, which confers resistance to the aminoglycoside G418; als which confers resistance to chlorsulfuron; and hygro, which confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, b-glucuronidase and its substrate, GUS, and luciferase and its substrate, luciferin.

C. Expression Constructs for Recombinant Protein Production

In the recombinant production of the MPO-derived proteins of the invention, it will be desirable to employ vectors comprising polynucleotide molecules for encoding the MPO derived proteins. Methods of preparing such vectors, as well as producing host cells transformed with such vectors, are well known to those skilled in the art. The polynucleotide molecules used in such an endeavor may be joined to a vector, which generally includes a selectable marker and an origin of replication, for propagation in a host. These elements of the expression constructs are well known to those of skill in the art. Generally, the expression vectors include DNA encoding the given protein being operably linked to suitable transcriptional or translational regulatory sequences, such as those derived from a mammalian, microbial, viral, or insect gene. Examples of regulatory sequences include transcriptional promoters, operators, or enhancers, mRNA ribosomal binding sites, and appropriate sequences which control transcription and translation.

The terms "expression vector," "expression construct " or "expression cassette " are used interchangeably throughout this specification and are meant to include any type of genetic construct containing a nucleic acid coding for a gene product in which part or all of the nucleic acid encoding sequence is capable of being transcribed.

The choice of a suitable expression vector for expression of the peptides or polypeptides of the invention will of course depend upon the specific host cell to be used, and is within the skill of the ordinary artisan. Methods for the construction of mammalian expression vectors are disclosed, for example, in Okayama and Berg (Mol. Cell. Biol. 3:280 (1983)); Cosman et al. (Mol. Immunol. 23:935 (1986)); Cosman et al. (Nature 312:768 (1984)); EP-A-0367566; and WO 91/18982.

The expression construct may further comprise a selectable marker that allows for the detection of the expression of a peptide or polypeptide. Usually the inclusion of a drug selection marker aids in cloning and in the selection of transformants, for example, neomycin, puromycin, hygromycin, DHFR, zeocin and histidinol. Alternatively, enzymes such as herpes simplex virus thymidine kinase (tk) (eukaryotic), b-galactosidase, luciferase, or chloramphenicol acetyltransferase (CAT) (prokaryotic) may be employed. Immunologic markers also can be employed. For example, epitope tags such as the FLAG system (IBI, New Haven, Conn.), HA and the 6xHis system (Qiagen, Chatsworth, Calif.) may be employed. Additionally, glutathione S-transferase (GST) system (Pharmacia, Piscataway, N.J.), or the maltose binding protein system (NEB, Beverley, Mass.) also may be used. The selectable marker employed is not believed to be important, so long as it is capable of being expressed simultaneously with the nucleic acid encoding a gene product. Further examples of selectable markers are well known to one of skill in the art.

Expression requires that appropriate signals be provided in the vectors, such as enhancers/promoters from both viral and mammalian sources that may be used to drive expression of the nucleic acids of interest in host cells. Usually, the nucleic acid being expressed is under transcriptional control of a promoter. A "promoter" refers to a DNA sequence recognized by the synthetic machinery of the cell, or introduced synthetic machinery, required to initiate the specific transcription of a gene. Nucleotide sequences are operably linked when the regulatory sequence functionally relates to the DNA encoding the peptide substrate or the fusion polypeptide. Thus, a promoter nucleotide sequence is operably linked to a given DNA sequence if the promoter nucleotide sequence directs the transcription of the sequence. Similarly, the phrase "under transcriptional control" means that the promoter is in the correct location and orientation in relation to the nucleic acid to control RNA polymerase initiation and expression of the gene. Any promoter that will drive the expression of the nucleic acid may be used. The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter. Common promoters include, e.g., the human cytomegalovirus (CMV) immediate early gene promoter, the SV40 early promoter, the Rous sarcoma virus long terminal repeat, β-actin, rat insulin promoter, the phosphoglycerol kinase promoter and glyceraldehyde-3-phosphate dehydrogenase promoter, all of which are promoters well known and readily available to those of skill in the art, can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose. By employing a promoter with well known properties, the level and pattern of expression of the protein of interest following transfection or transformation can be optimized. Inducible promoters also may be used.

Another regulatory element that is used in protein expression is an enhancer. These are genetic elements that increase transcription from a promoter located at a distant position on the same molecule of DNA. Where an expression construct employs a cDNA insert, one will typically desire to include a polyadenylation signal sequence to effect proper polyadenylation of the gene transcript. Any polyadenylation signal sequence recognized by cells of the selected transgenic animal species is suitable for the practice of the invention, such as human or bovine growth hormone and SV40 polyadenylation signals.

Also contemplated as an element of the expression cassette is a terminator. These elements can serve to enhance message levels and to minimize read through from the cassette into other sequences. The termination region which is employed primarily will be one selected for convenience, since termination regions for the applications such as those contemplated by the present invention appear to be relatively interchangeable. The termination region may be native with the transcriptional initiation, may be native to the DNA sequence of interest, or may be derived for another source.

D. Site-Specific Mutagenesis

Site-specific mutagenesis is another technique useful in the preparation of individual MPO-derived proteins used in the methods of the invention. This technique employs specific mutagenesis of the underlying DNA (that encodes the amino acid sequence that is targeted for modification). The technique further provides a ready ability to prepare and test sequence variants, incorporating one or more of the foregoing considerations, by introducing one or more nucleotide sequence changes into the DNA. Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique typically employs a bacteriophage vector that exists in both a single stranded and double stranded form. Typical vectors useful in site-directed mutagenesis include vectors such as the M13 phage. These phage vectors are commercially available and their use is generally well known to those skilled in the art. Double stranded plasmids also are routinely employed in site directed mutagenesis, which eliminates the step of transferring the gene of interest from a phage to a plasmid.

In general, site-directed mutagenesis is performed by first obtaining a single-stranded vector, or melting of two strands of a double stranded vector which includes within its sequence a DNA sequence encoding the desired protein. An oligonucleotide primer bearing the desired mutated sequence is synthetically prepared. This primer is then annealed with the single-stranded DNA preparation, taking into account the degree of mismatch when selecting hybridization (annealing) conditions, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected that include recombinant vectors bearing the mutated sequence arrangement.

Of course, the above described approach for site-directed mutagenesis is not the only method of generating potentially useful mutant peptide species and as such is not meant to be limiting. The present invention also contemplates other methods of achieving mutagenesis such as for example, treating the recombinant vectors carrying the gene of interest mutagenic agents, such as hydroxylamine, to obtain sequence variants.

E. Protein Purification

It will be desirable to purify the peptides of the present invention. Protein purification techniques are well known to those of skill in the art. These techniques involve, at one level, the crude fractionation of the cellular milieu to polypeptide and non-polypeptide fractions. Having separated the peptides or polypeptides of the invention from other proteins, the polypeptides or peptides of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Particularly efficient methods of purifying peptides include fast protein liquid chromatography (FPLC) and high performance liquid chromatography (HPLC).

Certain aspects of the present invention concern the purification, and in particular embodiments, the substantial purification, of an encoded polypeptide, protein or peptide. The term "purified polypeptide, protein or peptide" as used herein, is intended to refer to a composition, isolated from other components, wherein the polypeptide, protein or peptide is purified to any degree relative to its natural-obtainable state. A purified polypeptide, protein or peptide therefore also refers to a polypeptide, protein or peptide, free, from the environment in which it may naturally occur.

Generally, "purified" will refer to a polypeptide, protein or peptide composition that has been subjected to fractionation to remove various other components, and which composition substantially retains its expressed biological activity. Where the term "substantially purified" is used, this designation will refer to a composition in which the polypeptide, protein or peptide forms the major component of the composition, such as constituting about 50%, about 60%, about 70%, about 80%, about 90%, about 95% or more of the proteins in the composition.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified polypeptide, protein or peptide.

Methods of Conjugating MPO Fragments thereof to Active Agents

Having prepared and purified the MPO fragments, analogues or derivatives thereof, such proteins will either be used in the treatment of MPO-related disorders as discussed further below, or alternatively, such fragments will be conjugated to active agents to facilitate the therapeutic delivery of such active agents. These conjugates will be used in methods of facilitating systemic drug delivery of active agents that are conjugated to the MPO protein, and subsequent uptake of the conjugated MPO-therapeutic agent composition through transcytosis across the epithelial layer.

In general, MPO-active agent conjugates can be prepared using techniques known in the art. There are numerous approaches for the conjugation or chemical crosslinking of compounds to proteins and one skilled in the art can determine which method is appropriate for the active agent to be conjugated. The method employed must be capable of joining the active agent to the MPO fragment without interfering with the ability of the MPO fragment to bind to albumin, preferably without altering the desired activity of the compound once delivered. Preferred methods of conjugating the ligand to various compounds are set out in the example section, below. For linking metals to MPO, preferred reactions include, but are not limited to, binding to tyrosine residues through chloramine T methods, or use of Iodo beads (Pierce, Rockford, Ill.) for iodination reactions.

Where the active agent to be conjugated to the MPO fragment is a protein, such an MPO-active agent conjugate may readily be produced using e.g., the protein synthesis and/or the recombinant protein techniques discussed herein above. Herein throughout, the application makes reference to "conjugated active agents." These compositions are such that the therapeutic or diagnostic agents may need to be modified prior to conjugation with the MPO portion of the conjugate. Typically, such agents are modified by attaching a reactive group. The reactive group may be attached to the therapeutic agent either via a linking group, or optionally without using a linking group. In the present application, conjugated therapeutic and diagnostic agents are modified therapeutic and diagnostic agents that have been conjugated to a MPO fragment discussed above via a covalent bond formed between the reactive group of the modified therapeutic agent and a functionality on the MPO, with or without a linking group. As used throughout this application, the term "conjugated therapeutic agent" can be made more specific to refer to particular conjugated therapeutic agents, for example "conjugated antihistamine."

In such embodiments, it is contemplated that the active agent, e.g., the therapeutic or other agent that will be conjugated to the MPO will be derivatized or will already contain a reactive group. A "reactive group" as used herein are chemical groups capable of forming a covalent bond. Such reactive groups are coupled or bonded to a therapeutic or diagnostic agent and will generally be stable in an aqueous environment and will usually be carboxy, phosphoryl, or convenient acyl group, either as an ester or a mixed anhydride, an imidate or maleimide. Such groups are capable of forming a covalent bond with functionalities such as an amino group, a hydroxy or a thiol group. For the most part, the esters will involve phenolic compounds, or be thiol esters, alkyl esters, phosphate esters, or the like. Preferably, the reactive group will be a maleimide group. The reactive groups will react with functional groups on the MPO to form covalent bonds therewith. These functional groups include hydroxyl groups for bonding to ester reactive entities; thiol groups for bonding to maleimides, imidates and thioester groups; amino groups for bonding to carboxy, phosphoryl or acyl groups and carboxyl groups for bonding to amino groups. In preparing the conjugates, it may be desirable to protect the reactive or functional groups in order to protect such groups from reacting with each other. Various protective groups are disclosed in U.S. Pat. No. 5,493,007 which is hereby incorporated by reference. Such protective groups include acetyl, fluorenylmethyloxycarbonyl (FMOC), t-butyloxy carbonyl (BOC), benzyloxycarbonyl (CBZ), and the like. For small organic molecules all protecting groups like tetrahydropyranyl (THP), all silyl derivatives, acetals, thioacetals and the like.

The conjugates of the present invention may be such that the MPO portion of the conjugate is linked directly to the active therapeutic or diagnostic agent. Alternatively, the conjugate is one in which there is a linking group between the MPO and the active agent. Linking groups are chemical moieties that link or connect reactive groups to therapeutic agents. Linking groups may comprise one or more alkyl moieties, alkoxy moiety, alkenyl moiety, alkynyl moiety or amino moiety substituted by alkyl moieties, cycloalkyl moiety, polycyclic moiety, aryl moiety, polyaryl moieties, substituted aryl moieties, heterocyclic moieties, and substituted heterocyclic moieties. Linking groups may also comprise poly ethoxy amino acids, such as AEA ((2-amino) ethoxy acetic acid) or a AEEA ([2-(2-amino) ethoxy)]ethoxy acetic acid.

If the active agent is a protein or a peptide, there are many crosslinkers available in order to conjugate the active agent with the MPO fragment. (See for example, Chemistry of Protein Conjugation and Crosslinking. 1991, Shans Wong, CRC Press, Ann Arbor). The crosslinker is generally chosen based on the reactive groups available or inserted on the therapeutic compound. In addition, if there are no reactive groups a photoactivatible crosslinker can be used. In certain instances, it may be desirable to include a spacer between the MPO and the active agent. In one example, MPO and protein therapeutic compounds can be conjugated by the introduction of a sulfhydryl group on the MPO and the introduction of a cross-linker containing a reactive thiol group on to the protein compound through carboxyl groups (see, Wawizynczak and Thorpe, in Immunoconjugates: Antibody Conjugates in Radioimaging and Therapy of Cancer, C. W. Vogel (Ed.) Oxford University Press, 1987, pp. 28-55.; and Blair and Ghose, J. Immunol. Methods 59:129 ,1983).

Methods for conjugating the MPO with the representative labels may be readily accomplished by one of ordinary skill in the art (see, Trichothecene Antibody Conjugate, U.S. Pat. No. 4,744,981; Antibody Conjugate, U.S. Pat. No. 5,106,951; Fluorogenic Materials and Labeling Techniques, U.S. Pat. No. 4,018,884; Metal Radionuclide Labeled Proteins for Diagnosis and Therapy, U.S. Pat. No. 4,897,255; and Metal Radionuclide Chelating Compounds for Improved Chelation Kinetics, U.S. Pat. No. 4,988,496; see also Inman, Methods In Enzymology, Vol. 34, Affinity Techniques, Enzyme Purification: Part B, Jakoby and Wichek (eds.), Academic Press, New York, p. 30, 1974; see also Wilchek and Bayer, "The Avidin-Biotin Complex in Bioanalytical Applications," Anal. Biochem. 171:1-32, 1988; all incorporated herein by reference in their entirety for all purposes).

MPO-chemotherapeutic agents can comprise one or more compound moieties linked to the MPO fragment. For example, conjugation reactions may conjugate from 1 to 10 or more molecules of adriamycin to a single MPO molecule. Several atoms of gold or iodine can-be conjugated to a single MPO fragment. These formulations can be employed as mixtures, or they may be purified into specific MPO-active compound stoichiometric formulations. Those skilled in the art are able to determine which format and which stoichiometric ratio is preferred. Further, mixtures of active compounds may be linked to the MPO, e.g., MPO linked to a first therapeutic agent such as cisplatin and a second therapeutic agent such as taxol. These MPO-active agent conjugates may consist of a range of stoichiometric ratios of MPO to an active agent (e.g., MPO:active agent ratios of 1:1 to 1:4; 1:5 to 1:10; or 1:10 to 1:20). Optionally, a plurality of different active agents (e.g. 2, 3, or 4 such agents) may be each conjugated to the MPO.

The linker is preferably an organic moiety constructed to contain an alkyl, aryl and/or amino acid backbone and which will contain an amide, ether, ester, hydrazone, disulphide linkage or any combination thereof. Linkages containing amino acid, ether and amide bound components will be stable under conditions of physiological pH, normally 7.4 in serum and 4-5 on uptake into cells (endosomes). Preferred linkages are linkages containing esters or hydrazones that are stable at serum pH but hydrolyse to release the drug when exposed to intracellular pH. Disulphide linkages are preferred because they are sensitive to reductive cleavage; amino acid linkers can be designed to be sensitive to cleavage by specific enzymes in the desired target organ. Exemplary linkers are set out in Blattler et al. Biochem. 24:1517-1524, 1985; King et al. Biochem. 25:5774-5779, 1986; Srinivasachar and Nevill, Biochem. 28:2501-2509, 1989.

Drug-linker intermediates are similar to the conjugates described above but with either an active ester to react with free amine groups on the MPO or a maleimide to react with the free thiols that have been created on MPO through other groups.

Methods of crosslinking proteins and peptides are well known to those of skill in the art. Several hundred crosslinkers are available for conjugating a compound of interest with a polypeptide such as a MPO (see, e.g., Chemistry of Protein Conjugation and Crosslinking, Shans Wong, CRC Press, Ann Arbor (1991) and U.S. Pat. No. 5,981,194 and PCT Patent Publication Nos. WO 02/13843 and WO 01/59459 which are incorporated herein by reference in their entirety). Many reagents and cross-linkers can be used to prepare conjugates of an active agent and a MPO molecule, for instance, Hermanson et al. Bioconjugate Techniques, Academic Press, (1996). The crosslinker is generally chosen based on the reactive functional groups available or inserted on the therapeutic agent. In addition, if there are no reactive groups, a photoactivatible crosslinker can be used. In certain instances, it may be desirable to include a spacer between MPO and the agent. In one embodiment, MPO and the protein therapeutic agents may be conjugated by the introduction of a sulfhydryl group on MPO ligand and by the introduction of a crosslinker containing a reactive thiol group on to the protein compound through carboxyl groups (Wawizynczak and Thorpe in Immunoconjugates: Antibody Conjugates in Radioimaging and Therapy of Cancer, Vogel (Ed.) Oxford University Press, pp. 28-55 (1987); and Blair and Ghose (1983) J. Immunol. Methods 59:129). In some embodiments, the linker is vulnerable to hydrolysis at the acidic pH of the lysosome so as to free the agent from the and/or linker.

When a linker is used, the linker is preferably an organic moiety constructed to contain an alkyl, aryl and/or amino acid backbone, and containing an amide, ether, ester, hydrazone, disulphide linkage or any combination thereof. Linkages containing amino acid, ether and amide bound components are stable under conditions of physiological pH, normally 7.4 in serum. Preferred linkages are those containing esters or hydrazones that are stable at serum pH, but that hydrolyze to release the drug when exposed to intracellular pH. Disulphide linkages are preferred because they are sensitive to reductive cleavage. In addition, amino acid linkers may be designed to be sensitive to cleavage by specific enzymes in the desired target organ. Exemplary linkers are described in Blattler et al. (1985) Biochem. 24:1517-1524; King et al. (1986) Biochem. 25:5774-5779; Srinivasachar and Nevill (1989) Biochem. 28:2501-2509.

In some embodiments, the linker is a polyethylene glycol or polypropylene glycol. In other embodiments, the linker is from 4 to 20 atoms long. In other embodiments, the linker is from 1 to 30 atoms long with carbon chain atoms that may be substituted by heteroatoms independently selected from the group consisting of O, N, or S. In some embodiments, from 1 to 4 or up to one-third of the C atoms are substituted with a heteroatom independently selected from O, N, S. In other embodiments, the linker contains a moiety subject to hydrolysis upon delivery to the target organ environment. In some embodiments, the linker group is preferably hydrophilic to enhance the solubility of the conjugate in body fluids.

Active Agents

The conjugates of the present invention will comprise an MPO portion which will mediate the transcytosis of the conjugate and an "active agent" portion. Thus, generically the conjugate may have the formula A-B or B-A, where "A" is the active agent and "B" is the MPO portion. The active agent may be linked to the C-terminus of the MPO portion (as depicted by the formula B-A) or alternatively, it may be linked to the N-terminus of the MPO portion, as depicted by the formula A-B). Where there is a linker (L) between the MPO portion and the active agent portion, the conjugate may be depicted as B-L-A or A-L-B, such that in B-L-A, the linker is linker to the C-terminus of the MPO portion, and in A-L-B, the linker is linked to the N-terminus of the MPO portion. It should be understood that in formulae B-L-A or A-L-B, when the active agent is a protein, the active agent may be linked to the linker through the N-terminus of the active agent or the C-terminus of the active agent.

As used herein the term "active agent" refers to any agent that is being delivered using the MPO as a delivery vehicle. As such, the term "active agent" includes, without limitation, any drug or antigen or any drug- or antigen-loaded or drug- or antigen-encapsulated nanoparticle, microparticle, liposome, or micellar formulation capable of eliciting a biological response in a human or animal. Examples of drug- or antigen-loaded or drug- or antigen-encapsulated formulations include those in which the active agent is encapsulated or loaded into nano- or microparticles, such as biodegradable nano- or microparticles, and which have the MPO peptide adsorbed, coated or covalently bonded, such as directly linked or linked via a linking moiety, onto the surface of the nano- or microparticle. Additionally, the MPO peptide can form the nano- or microparticle itself or the peptide can be covalently attached to the polymer or polymers used in the production of the biodegradable nano- or microparticles or drug-loaded or drug-encapsulated nano- or microparticles or the peptide can be directly conjugated to the active agent. Such conjugations to active agents include fusion proteins in which a DNA sequence coding for the peptide is fused in-frame to the gene or cDNA coding for a therapeutic peptide or protein such that the modified gene codes for a recombinant fusion protein.

Preferably, the active agent is a therapeutic agent. Therapeutic agents are agents that have a therapeutic effect and will include peptides and non-peptide organic molecules. Therapeutic agents include but are not limited to wound healing agents, antibiotics, anti-infectives, anti-oxidants, chemotherapeutic agents, anti-cancer agents, anti-inflammatory agents, and antiproliferative drugs. Therapeutic agents also include abortifacients, ace-inhibitor, α-adrenergic agonists, β-adrenergic agonists, α-adrenergic blockers, β-adrenergic blockers, adrenocortical steroids, adrenocortical suppressants, adrenocorticotrophic hormones, alcohol deterrents, aldose reductase inhibitors, aldosterone antagonists, 5-alpha reductase inhibitors, anabolics, analgesics, analgesics, analgesics, androgens, anesthetics, anesthetics, angiotensin converting enzyme inhibitors, anorexics, antacids, anthelmintics, antiacne agents, antiallergic agents, antialopecia agents, antiamebic agents, antiandrogen agents, antianginal agents, antiarrhythmic agents, antiarteriosclerotic agents, antiarthritic/antirheumatic agents, antiasthmatic agents, antibacterial agents, aminoglycosides, amphenicols, ansamycins, β-lactams, lincosamides, macrolides, polypeptides, tetracyclines, antibacterial agents, 2,4-diaminopyrimidines, nitrofurans, quinolones and analogs, sulfonamides, sulfones, antibiotics, anticholelithogenic agents, anticholesteremic agents, anticholinergic agents, anticoagulant agents, anticonvulsant agents, antidepressant agents, hydrazides/hydrazines, pyrrolidones, tetracyclics, antidiabetic agents, biguanides, hormones, sulfonylurea derivatives, antidiarrheal agents, antidiuretic agents, antidotes, antidote, antidote, antidote, antidote, antidyskinetic, antieczematic, antiemetic agents, antiepileptic agents, antiestrogen agents, antifibrotic agents, antiflatulent agents, antifungal agents, polyenes, allylamines, imidazoles, triazoles and antiglaucoma agents.

Other therapeutic agents include anti-viral agents, anti-fusogenic agents, blood brain barrier peptides (BBB peptides), RGD peptides, glucagon-like peptides, antigonadotropin, antigout, antihemorrhagic and antihistaminic agents; alkylmaine derivatives, aminoalkyl ethers, ethylenediamine derivatives, piperazines and tricyclics, antihypercholesterolemic, antihyperlipidemic, antihyperlipidemic and antihyperlipoproteinemic agents, aryloxyalkanoic acid derivatives, bile acid sequesterants, HMGCoA reductase inhibitors, nicotine acid derivatives, thyroid hormones/analogs, antihyperphosphatemic, antihypertensive agents, arlethanolamine derivatives, arloxypropanolamine derivatives, benzothiadiazine derivatives, n-carboxyalkyl derivatives, dihydropyridine derivatives, guanidine derivatives, hydrazines/phthalazines, imidazole derivatives, quaternary ammonium compounds, quinazolinyl piperazine derivatives, reserpine derivatives, sulfonamide derivatives, antihyperthyroid agents, antihypotensive agents, antihypothyroid agents, anti-infective agents, anti-inflammatory agents, anti-inflammatory agents, aminoarylcarboxylic acid derivatives, arylacetic acid derivatives, arylbutyric acid derivatives and arylcarboxylic acids.

Therapeutic agents also include arylpropionic acid derivatives, pyrazoles, pyrazolones, salicylic acid derivatives, thiazinecarboxamides, antileprotic, antileukemic, antilipemic, antilipidemic, antimalarial, antimanic, antimethemoglobinemic, antimigraine, antimycotic, antinauseant, antineoplastic and alkylating agents, antimetabolites, enzymes, androgens, antiadrenals, antiandrogens, antiestrogens, progestogens, adjunct, folic acid replenisher, uroprotective and antiosteoporotic agents.

Therapeutic agents also include antipagetic, antiparkinsonian, antiperistaltic, antipheochromocytoma, antipneumocystis, antiprostatic hypertrophy, antiprotozoal, antiprozoal, antipruritic, antipsoriatic and antipsychotic agents, butyrophenes, phenothiazines, thioxanthenes, antipyretic, antirheumatic, antirickettsial, antiseborreheic and antiseptic/disinfectant agents, alcohols, aldehydes, dyes, guanidines, halogens/halogen compounds, mercurial compounds, nitrofurans, peroxides/pernanganates, phenols, quinolines, silver compounds, others, antispasmodic, antisyphilitic, antithrombotic, antitubercular, antitumor, antitussive, antiulcerative, antiurolithic, antivenin, antivertigo and antiviral agents, purines/pyrimidinomes, anxiolytic, arylpiperazines, benzodiazepine derivatives, carbamates, astringent, benzodiazepine antagonist, beta-blocker, bronchodilator, ephedrine derivatives, calcium channel blockers, arylalkylamines, dihydropyridine derivatives, piperazine derivatives, calcium regulators, calcium supplements, cancer chemotherapy agents, capillary protectants, carbonic anhydrase inhibitors, cardiac depressants, cardiotonic, cathartic, cation-exchange resin, cck antagonists, central stimulants, cerebral vasodilators, chelating agents, cholecystokinn antagonists, choleitholytic agents, choleretic agents, cholinergic agents, cholinesterase inhibitors, cholinesterase reactivators, cns stimulants, cognition activators, contraceptives, agents to control intraocular pressure, converting-enzyme inhibitors, coronary vasodilators, cytoprotectants, debriging agenta, decongestanta, depigmentora, dermatitis herpretiformis suppresanta, diagnostic aids, digestive aids, diuretics, benthothiadiazine derivatives, organomercurials, pteridines, purines, steroids, sulfanamide derivatives, uracils, dopamine and receptor agonists.

Therapeutic agents also include dopamine receptor antagonists, ectoparasiticides, electrolyte replenishers, emetics, enzymes, digestive agents, mucolytic agents, penicillin inactivating agents, proteolytic agents, enzyme inducers, estrogen antagonists, expectorant gastric and pancreatic secreation stimulants, gastric proton pump inhibitor, gastric secretion inhibitors, glucocorticoids, α-glucosidase inhibitors, gonad-stimulating principles, gonadotrophic hormones, gout suppressant, growth hormone inhibitor, growth hormone releasing factor, growth stimulant, hematinic, hemolytic, demostatic, heparin antagonist, hepatoprotectant, histamine $h_1$-receptor antagonists, histamine $h_2$-receptor antagonists, HMGCoA reductase inhibitor, hypnotic, hypocholesteremic and hypolipidemic agents.

Therapeutic agents also include hypotensive, immunomodulators, immunosuppressants, inotrophic agents, keratolytic agents, lactation stimulating hormone, laxative/cathargic, lipotrophic agents, local anesthetics, lupus erythematosus suppressants, major tranquilizers, mineralocorticoids, minor tranquilizers, miotic agents, monoamine oxidase ihibitors, mucolytic agents, muscle relaxants, mydriatic agents, narcotic agents; analgesics, narcotic antagonists, nasal decongestants, neuroleptic agents, neuromuscular blocking agents, neuroprotective agents, nmda antagonists, nootropic agents, nthe agents, opioid analgesics, oral contraceptives and ovarian hormones.

Therapeutic agents also include oxytocic agents, blood brain barrier protiens, GP-41 peptides, insulinotropic peptides parasympathomimetic agents, pediculicides, pepsin inhibitors, peripheral vasodilators, peristaltic stimulants, pigmentation agents, plasma volume expanders, potassium channel activators./openers, pressor agents, progestogen, prolactin inhibitors, prostaglandin/prostaglandin analogs, protease inhibitors, proton pump inhibitors, 5α-reductase inhibitors, replenishers/supplements, respiratory stimulants, reverse transcriptase inhibitors, scabicides, sclerosing agents, sedative/hypnotic agents, acyclic ureides, alcohols, amides, barbituric acid derivatives, benzodiazepine derivatives, bromides, carbamates, chloral derivatives, quinazolone derivatives and piperidinediones.

Therapeutic agents also include serotonin receptor agonists, serotonin receptor antagonists, serotonin uptake inhibitors, skeletal muscle relaxants, somatostatin analogs, spasmolytic agents, stool softeners, succinylcholine synergists, sympathomimetics, thrombolytics, thyroid hormone, thyroid inhibitors, thyrotrophic hormone, tocolytic, topical protectants, uricosurics, vasodilators, vasopressors, vasoprotectants, vitamin/vitamin sources, antichitic, antiscorbutic and antixerophthalmic agents, enzyme co-factors, hematopoietic, prombogenic agents and xanthene oxidase inhibitors.

In view of the above discussion, it should be understood that a preferred active agent is a drug. As used herein, the term "drug" includes, without limitation, any pharmaceutically active agent. Representative drugs include, but are not limited to, peptides or proteins, hormones, analgesics, anti-migraine agents, anti-coagulant agents, anti-emetic agents, cardiovascular agents, anti-hypertensive agents, narcotic antagonists, chelating agents, anti-anginal agents, chemotherapy agents, sedatives, anti-neoplastics, prostaglandins and, antidiuretic agents. Typical drugs include peptides, proteins or hormones such as insulin, calcitonin, calcitonin gene regulating protein, atrial natriuretic protein, colony stimulating factor, betaseron, erythropoietin (EPO), interferons such as α, β, or γ interferon, somatropin, somatotropin, somatostatin, insulin-like growth factor (somatomedins), luteinizing hormone releasing hormone (LHRH), tissue plasminogen activator (TPA), growth hormone releasing hormone (GHRH), oxytocin, estradiol, growth hormones, leuprolide acetate, factor VIII, interleukins such as interleukin-2, and analogues thereof; analgesics such as fentanyl, sufentanil, butorphanol, buprenorphine, levorphanol, morphine, hydromorphone, hydrocodone, oxymorphone, methadone, lidocaine, bupivacaine, diclofenac, naproxen, paverin, and analogues thereof; anti-migraine agents such as sumatriptan, ergot alkaloids, and analogues thereof; anti-coagulant agents such as heparin, hirudin, and analogues thereof; anti-emetic agents such as scopolamine, ondansetron, domperidone, metoclopramide, and analogues thereof; cardiovascular agents, anti-hypertensive agents and vasodilators such as diltiazem, clonidine, nifedipine, verapamil, isosorbide-5-mononitrate, organic nitrates, agents used in treatment of heart disorders, and analogues thereof; sedatives such as benzodiazepines, phenothiozines, and analogues thereof; narcotic antagonists such as naltrexone, naloxone, and analogues thereof; chelating agents such as deferoxamine, and analogues thereof; anti-diuretic agents such as desmopressin, vasopressin, and analogues thereof; anti-anginal agents such as nitroglycerine, and analogues thereof; anti-neoplastics such as 5-fluorouracil, bleomycin, and analogues thereof; prostaglandins and analogues thereof; and chemotherapy agents such as vincristine, and analogues thereof Representative drugs also include antisense oligonucleotides, genes, gene correcting hybrid oligonucleotides, ribozymes, aptameric oligonucleotides, triple-helix froming oligonucleotides, inhibitors of signal transduction pathways, tyrosine kinase inhibitors and DNA modifying agents. As used herein, the term "drug" also includes, without limitation, systems for gene delivery and gene therapeutics, including viral systems for gene delivery such as adenovirus, adeono-associated virus, retroviruses, herpes simplex virus, sindbus virus, liposomes, cationic lipids, dendrimers, imaging agents and enzymes.

In specific embodiments, the active agent may be diagnostic imaging agent. Diagnostic imaging agents are agents useful in imaging the mammalian vascular system and include such agents as position emission tomography (PET) agents, computerized tomography (CT) agents, magnetic resonance imaging (MRI) agents, nuclear magnetic imaging agents (NMI), fluroscopy agents and ultrasound contrast agents. Diagnostic agents of interest include radioisotopes of such elements as iodine (I), including $^{123}$I, $^{125}$I, $^{131}$I, etc., barium (Ba), gadolinium (Gd), technetium (Tc), including $^{99}$Tc, phosphorus (P), including $^{31}$P, ron (Fe), manganese (Mn), thallium (Tl), chromium (Cr), including $^{51}$Cr, carbon (C), including $^{14}$C, or the like, fluorescently labeled compounds, etc.

Other agents that could be delivered using the methods of the invention include wound-healing agents such as e.g., integrins, cell adhesion molecules such as ICAM, ECAM, ELAM and the like, antibiotics, growth factors such as EGF, PDGF, IGF, bFGF, aFGF and KGF, fibrin, thrombin, RGD peptides and the like. Antiproliferative agents could also form part of the conjugates described herein, such compounds include antimetabolites, topoisomerase inhibitors, folic acid antagonists like methotrexate, purine antagonists like mercaptopurine, azathioprine, and pyrimidine antagonists like fluorouracil, cytarabine and the like. The conjugates may comprise antioxidants that prevent oxidative damage to tissue e.g., tocopherol derivatives (vitamin E), and free radical scavengers such as SOD, glutathione and the like.

Antifungal agents such as amphoterecin B, myconazole, tetraconazole, econazole, isoconazole, thioconazole, biphonazole, clotrimazole, ketoconazole, butaconazole, itraconazole, oxiconazole, phenticonazole, nystatin, naphthyphene, zinoconazole, cyclopyroxolamine and fluconazole may be delivered as conjugates as described herein.

The active agent may be an antibacterial agent from one of the major classes of antibiotics are (1) the beta-lactams, including the penicillins, cephalosporins and monobactams; (2) the aminoglycosides, e.g. gentamicin, tobramycin, netilmycin, and amikacin; (3) the tetracyclines; (4) the sulfonamides and trimethoprim; (5) the fluoroquinolones, e.g. ciprofloxacin, norfloxacin, and ofloxacin; (6) vancomycin; (7) the macrolides, which include for example, erythromycin, azithromycin, and clarithromycin; and (8) other antibiotics, e.g., the polymyxins, chloramphenicol and the lincosamides. Antibiotics accomplish their anti-bacterial effect through several mechanisms of action which can be generally grouped as follows: (1) agents acting on the bacterial cell wall such as bacitracin, the cephalosporins, cycloserine, fosfomycin, the penicillins, ristocetin, and vancomycin; (2) agents affecting the cell membrane or exerting a detergent effect, such as colistin, novobiocin and polymyxins; (3) agents affecting cellular mechanisms of replication, information transfer, and protein synthesis by their effects on ribosomes, e.g., the aminoglycosides, the tetracyclines, chloramphenicol, clindamycin, cycloheximide, fuicidin, lincomycin, puromycin, rifampicin, other streptomycins, and the macrolide antibiotics such as erythromycin and oleandomycin; (4) agents affecting nucleic acid metabolism, e.g., the fluoroquinolones, actinomycin, ethambutol, 5-fluorocytosine, griseofulvin, rifamycins; and (5) drugs affecting intermediary metabolism, such as the sulfonamides, trimethoprim, and the tuberculostatic agents isoniazid and para-aminosalicylic acid. Some agents may have more than one primary mechanism of action, especially at high concentrations. In addition, secondary changes in the structure or metabolism of the bacterial cell often occur after the primary effect of the antimicrobial drug.

The active agent may be an anticancer agent. Anti-cancer agents (chemotherapeutic agents) are natural or synthetic molecules which are effective against one or more forms of cancer. This definition includes molecules which by their mechanism of action are cytotoxic (anti-cancer chemotherapeutic agents), those which stimulate the immune system (immune stimulators) and modulators of angiogenesis. The outcome in either case is the slowing of the growth of cancer cells. Numerous drugs fall into the category of chemotherapeutic agents useful in the treatment of neoplastic disease that are amenable to the embodiment of this application. Such agents derivitized with this technology can include anti-metabolites such as metotrexate (folic acid derivatives), fluoroaucil, cytarabine, mercaptopurine, thioguanine, petostatin (pyrimidine and purine analogs or inhibitors), a variety of natural products such as vincristine and vinblastine (vinca alkaloid), etoposide and teniposide, various antibiotics such as miotomycin, plicamycin, bleomycin, doxorubicin, dactomycin; a variety of biological response modifiers including interferon-alpha; a variety of miscellaneous agents and hormonal modulators including cisplatin, hydroxyurea, mitoxantorne, procarbozine, aminogultethimide, prednisone, progestins, estrogens, antiestorgens such as tamoxifen, androgenic steroids, antiadrogenic agents such as flutamide, gonadotropin releasing hormones analogs such as leuprolide, the matrix metalloprotease inhibitors (MMPIs) as well as anti-cancer agents including Taxol (paclitaxel) and related molecules collectively termed taxoids, taxines or taxanes.

Included within the definition of "taxoids" are various modifications and attachments to the basic ring structure (taxoid nucleus) as may be shown to be efficacious for reducing cancer cell growth and which can be constructed by organic chemical techniques known to those skilled in the art.

Chemotherapeutics include podophyllotoxins and their derivatives and analogues. Another important class of chemotherapeutics useful in this invention are camptothecins.

Another preferred class of chemotherapeutics useful in this invention are the anthracyclines (adriamycin and daunorubicin).

Another important class of chemotherapeutics are compounds which are drawn from the following list: Taxotere, Amonafide, Illudin S, 6-hydroxymethylacylfulvene Bryostatin 1, 26-succinylbryostatin 1, Palmitoyl Rhizoxin, DUP 941, Mitomycin B, Mitomycin C, Penclomedine, angiogenesis inhibitor compounds, Cisplatin hydrophobic complexes such as 2-hydrazino-4,5-dihydro-1H-imidazole with platinum chloride and 5-hydrazino-3,4-dihydro-2H-pyrrole with platinum chloride, vitamin A, vitamin E and its derivatives, particularly tocopherol succinate.

Other compounds useful in the invention include: 1,3-bis (2-chloroethyl)-1-nitrosurea ("carmustine" or "BCNU"), 5-fluorouracil, doxorubicin ("adriamycin"), epirubicin, aclarubicin, Bisantrene(bis(2-imidazolen-2-ylhydrazone)-9,10-anthracenedicarboxaldehyde, mitoxantrone, methotrexate, edatrexate, muramyl tripeptide, muramyl dipeptide, lipopolysaccharides, vidarabine and its 2-fluoro derivative, resveratrol, retinoic acid and retinol, carotenoids, and tamoxifen.

Other chemotherapeutic agents useful in the application of this invention include: Decarbazine, Lonidamine, Piroxantrone, Anthrapyrazoles, Etoposide, Camptothecin, 9-aminocamptothecin, 9-nitrocamptothecin, camptothecin-11 ("Irinotecan'), Topotecan, Bleomycin, the Vinca alkaloids and their analogs [Vincristine, Vinorelbine, Vindesine, Vintripol, Vinxaltine, Ancitabine], 6-aminochrysene, and Navelbine.

Other compounds useful in the application of the invention are mimetics of taxol, eleutherobins, sarcodictyins, discodermolides and epothiolones.

Other anticancer agents include anti-cancer agents such as fluoropyrimidines, pyrimidine nucleosides, purines, platinum analogs, anthracyclines/anthracenediones, podophyllotoxins, camptothecins, hormones and hormonal analogs, enzymes, proteins and antibodies, vinca alkaloids, taxanes, antihormonal agents, antifolates, antimicrotubule agents, alkylating agents (classical and non-classical), antimetabolites, antibiotics, topoisomerase inhibitors, antivirals, and miscellaneous cytotoxic agents, for example hydroxyurea, mitotane, fusion toxins, PZA, bryostatin, retinoids, butyric acid and derivatives, pentosan, fumagillin, and others. The objective of all antineoplastic drugs is to eliminate (cure) or to retard the growth and spread (remission) of cancer cells. The majority of the above listed antineoplastic agents pursue this objective by possessing primary cytotoxic activity, effecting a direct kill on the cancer cells. Other antineoplastic drugs stimulate the body's natural immunity to effect cancer cell death.

Antihypertensive agents could be the active agent port of the conjugates described herein. Antihypertensive agents are various agents that can be used to treat hypertension, including but not limited to enalapril, acebutolol, and doxazosin. Enarlapril is a pro-drug that is activated to the angiotensin-converting enzyme (ACE) inhibitor, enalaprilat. This pro-drug inhibits the conversion of angiotensin I to angiotensin II and exerts an antihypertensive effect by suppressing the renin-angiotensin-aldosterone system. Acebutolol is in a class of drugs called beta-blockers, which affect the heart and circulatory system. Acebutolol is used to lower blood pressure, lower heart rate, and reduce angina (chest pain). Doxazosin is a member of the alpha blocker family of drugs used to lower blood pressure in people with hypertension. Doxazosin is also used to treat symptoms of benign prostatic hyperplasia (BPH). Doxazosin works by relaxing blood vessels so that blood passes through them more easily, which helps to lower blood pressure.

The active agent may be a steroid. A typical such steroid is methylprednisolone, a synthetic steroid that suppresses acute and chronic inflammation. In addition, it stimulates gluconeogenesis, increases catabolism of proteins and mobilization of free fatty acids. In addition, it potentiates vascular smooth muscle relaxation by beta adrenergic agonists, and may alter airway hyperactivity. It is also a potent inhibitor of the inflammatory response. Other similar steroids are known to those of skill in the art.

Disorders to be Treated

It is contemplated that the compositions of the present invention will be used in the treatment of a variety of disorders. As explained herein throughout there are at least two types of medicaments that may arise from the present invention. Firstly, the present invention provides compositions that comprise MPO fragments described herein above as therapeutic agents alone or in combination with other therapeutic compositions for the treatment of cardiovascular diseases, autoimmune diseases, inflammatory diseases and the like, that involve an over or increased expression or activity of MPO which leads to the generation of destructive NO-derived oxidants and nitrotyrosine formation. Secondly, the invention contemplates therapeutic compositions which are conjugates of MPO fragments and a second portion that is the active agent as described herein above. Various disorders will be treated by these two classes of therapeutic compositions of the present invention.

A. Treatment using Unconjugated MPO Fragments

MPO fragments or combinations will be useful for the treatment of any disorder that is caused by an increase or excess of MPO. The release of MPO from PMN, catalyses the conversion of $H_2O_2$ to HOCl, a potent antibacterial agent (1). MPO transport across the endothelial cell barrier and its accumulation in the sub-endothelium is crucial in oxidative events since MPO is an enzymatic source of NO-derived oxidants and nitrotyrosine formation (2-7). Recent studies showed that MPO levels in plasma provide a useful measure of the severity of acute coronary syndromes (12, 13). MPO levels in the plasma increased (ranging from pM to nM) in patients with different inflammatory pathologies (13-15). U.S. Pat. No. 5,708,010 and U.S. Pat. No. 5,708,009 discuss certain diseases that are characterized by an excess of MPO. Any such diseases may be readily treated by the compositions described herein. Such diseases encompasses those disorders associated with an inappropriate amount or reaction to myeloperoxidase present. Examples of such conditions, include but are not limited to systemic lupus erythrematosas, Hashimoto's thyroiditis, myasthenia gravis, rheumatoid arthritis, multiple sclerosis, Guillan Barre syndrome, and glomerulonephritis.

As used herein, the term "inhibits MPO activity" includes its generally accepted meaning which includes prohibiting, preventing, restraining, and slowing, stopping or reversing progression, severity or a resultant symptom of an MPO activity or expression. As such, the present method includes both medical therapeutic and/or prophylactic administration, as appropriate. In order to investigate the MPO activity inhibiting properties of the fragments described in Jansson (Free Rad Res Comms, 14(3), 195-208, (1991), incorporated herein by reference.). In an in vitro cell-based assay, human PMN leukocytes are stimulated with estriol to increase myeloperoxidase activity in the presence of added hydrogen peroxide. The conversion of luminol by hypochlorous acid is measured by chemiluminescence. The reaction mix consists of cells ($10^6$), inhibitory compound (i.e., MPO fragment or derivative thereof to be tested (e.g., at a concentration of 1 µM), hydrogen peroxide (0.1 mM), and luminol (0.2 mM) incubated at 37° C.

The MPO inhibition also may be monitored using an in vitro cell free assay. In such an assay, purified human myeloperoxidase is incubated with an appropriate concentration of the inhibitory fragment, in the presence of luminol at 37° C. The substrate, hydrogen peroxide, is added and the chemiluminescence measured. The reaction mix is human MPO (250 ng), inhibitory fragment (e.g., 10 µM, titrated), hydrogen peroxide (1 mm), and luminol (0.2 mm).

The inhibitory fragments also may be tested in an in vivo setting. For example, a clinical trial may be set up in which five to fifty subjects are selected for the clinical study. The women suffer from SLE or rheumatoid arthritis. Because of the idiosyncratic and subjective nature of these disorders, the study has a placebo control group, i.e., the subjects are divided into two groups, one of which receives a MPO fragment as the active agent and the other receives a placebo. Subjects in the test group receive between 50-200 mg of the MPO fragment based drug per day by the oral route. The subjects are maintained on this therapy for 3-12 months. Accurate records are kept as to the number and severity of the symptoms in both groups and at the end of the study these results are compared. The results are compared both between members of each group and also the results for each patient are compared to the symptoms reported by each patient before the study began.

Of course, it should be understood that the unconjugated MPO fragments may form part of a therapeutic regimen in which the MPO-based treatment is used in combination with a plurality of other therapies for the given disorder. As such, combination therapy is specifically contemplated.

B. Treatment using MPO-Based Conjugates

The conjugates described herein will be useful therapeutic agents for the treatment of any disease state to which a therapeutic agent may be delivered via transcytosis. Such diseases are only limited by the accessibility of the target cells of the disease state to the therapeutic compositions described herein. As such, any disorder in which the cells to be treated have caveolae that will permit the uptake of albumin via transcytosis and therefore, also permit the uptake of MPO-bound moieties by transcytosis, will be treatable by the methods of the present invention. In a general sense, the MPO fragments that form part of the conjugates of the present invention serve as a delivery vehicle for the active agents of the conjugates and enhance the uptake of the active agent into the cells of to be treated. As such, conjugating the MPO fragments of the invention to active agents will facilitate an increased uptake of the active agents into the cellular site of action as compared to the uptake of the given active agent in the absence of the conjugation.

Exemplary types of active agents that may be used in the conjugates are outlined above. Such agents may be used to treat a variety of disorders. For example, the conjugates may be used in the treatment of a CNS condition or disorder where it is particularly desirable that the active agent traverses the blood-brain barrier. CNS conditions that can be treated include, but are not limited to, Alzheimer's Disease, Parkinson's Disease, multiple sclerosis, and amylotrophic lateral sclerosis. In one group of particularly preferred embodiments to be treated, the CNS condition or disorder to be treated is a brain tumor or other neoplasia (e.g., a CNS tumor such as a glioblastoma). Such tumors or neoplasia may be primary tumors or may be metastases. In addition, lysosomal storage diseases also may be treated using compositions of the invention which traverse the blood-brain barrier.

Other neoplastic disorders also may be treated. In such embodiments, the MPO-based conjugates of the invention will target directly to cancer cells via caveolae present on the epithelial surface. As discussed herein, these structures mediate the uptake of albumin and MPO fragments of the invention contain an albumin binding sequence. Therefore, the conjugates of the invention become bound to the albumin, and are taken up into the subepithelial space through the transcystosis of albumin to which the MPO fragments are bound or "docked". Thus, the MPO fragments can be used to preferentially target drugs to metastatic tumor cells. Therefore, the MPO peptide fragments or their derivatives or analogs are useful as agents for the treatment of different types of cancers such as breast carcinoma, melanoma, and fibrosarcoma.

The conjugates also may be used to treat a pulmonary condition, i.e., a disease which affects lung function. Such conditions may result from a defect in a gene or genes associated with lung function (e.g., cystic fibrosis), asthma, allergies, an immune or autoimmune disorder, a microbial infection (e.g. bacterial, viral, fungal or parasitic infection), or a mechanical injury to the lungs (examples of pulmonary conditions that may be treated include but are not limited to cystic fibrosis, asthmatic bronchitis, tuberculosis, bronchitis, bronchiectasis, laryngotracheobronchitis, bronchiolitis, emphysema, bronchial pneumonia, allergic bronchopneumonia, viral pneumonia, pertussis, diphtheria, spasmodic croup, pulmonary phthisis, encephalitis with retained secretions, pulmonary edema, cytomegaloviral pneumonia or miliary tuberculosis, drug-induced lung disease (e.g., after administration of penicillin, nitrofurantoin), neoplastic lung disease having lymphangitic spread pattern or bronchoalveolar cell carcinoma, infectious or noninfectious granulomatous disease, hypersensitivity pneumonitis, histoplasmosis, tuberculosis, cryptogenic fibrosing alveolitis, hereditary pulmonary disorders, such as alveolar microlithiasis and bronchiectasis, eosinophilic granuloma, lympphangioleimyomatosis, and plumonary alveolar proteinosis disorders. Symptoms of a pulmonary condition are symptoms associated with any of the pulmonary conditions described above. The classic symptoms associated with such pulmonary conditions may include coughing, exertional dyspnea, wheezing, chest pain and purulent sputum production. Other components of the syndrome which may accompany a pulmonary condition include hypoxia, $CO_2$ narcosis, hyperventilation, decreased expiration volume, and decreased lung capacity. Any of these symptoms may be monitored before and after the treatment at varying periods in order to determine the effectiveness of the treatment regiment.

Inflammatory disease also may be treated by the conjugates of the present invention. Inflammatory diseases are characterized by activation of leukocytes leads to an impairment of normal physiologic function. Examples of such conditions include acute and chronic inflammation such as osteoarthritis, sepsis, ARDS, immune and autoimmune disorders, rheumatoid arthritis, IBD (inflammatory bowel disease), lupus, MS, graft rejection, cirrhosis, sarcoidosis, granulomatous lesions, periodontitis/gingivitis, graft-vs.-host disease, contact dermatitis, and the like. Included among autoimmune disorders which may be treated using the present method are chronic active hepatitis, Graves'disease, insulin-dependent diabetes mellitus (type I), and Hasshimoto's thyroiditis. Included among inflammatory disorders which may be treated using the present method are inflammatory brain disease, inflammatory demyelinating disease, inflammatory vasculitis, inflammatory myopathies, osteomyelitis, Crohn's disease and interstitial cystitis. Additional examples of inflammatory diseases include myocardial diseases, infectious diseases, pulmonary diseases and graft rejection From the above discussion, it should be understood that the disease that may be treated by the conjugates of the present invention are limited only by the availability of caveolae on the epithelial surface at or near the site of disorder or the target of action of the drug being administered because the MPO-fragments of the present invention are used to enhance the uptake and delivery of the active agent at such a site through such structures. Therefore, it should be understood that the above-listed conditions are merely an exemplary, rather than exhaustive list of the type of conditions that may be treated using the conjugates of the present invention.

Pharmaceutical Compositions

Pharmaceutical compositions for administration according to the present invention can comprise either fragments of MPO alone as described above for the treatment of disorders in which there is an abnormally high expression or activity of MPO. Other pharmaceutical compositions may comprise MPO fragments conjugated to an active agent of interest wherein the MPO serves as an albumin docking peptide to bind the conjugate to circulating albumin in vivo and result in the uptake of the active agent when albumin is taken up by caveolae. The pharmaceutical compositions also may include additional therapeutic agents for the treatment of the given disease being treated. Regardless of whether the active component of the pharmaceutical composition is an MPO fragment alone, an MPO fragment conjugated to an active agent of interest, or the combination of either or both of these former entities with yet another therapeutic composition, each of these preparations is in some aspects provided in a pharmaceutically acceptable form optionally combined with a pharmaceutically acceptable carrier. These compositions are administered by any methods that achieve their intended purposes. Individualized amounts and regimens for the administration of the compositions for the treatment of the given disorder are determined readily by those with ordinary skill in the art using assays that are used for the diagnosis of the disorder and determining the level of effect a given therapeutic intervention produces.

It is understood that the suitable dose of a composition according to the present invention will depend upon the age, health and weight of the recipient, kind of concurrent treatment, if any, frequency of treatment, and the nature of the effect desired. However, the dosage is tailored to the individual subject, as is understood and determinable by one of skill in the art, without undue experimentation. This typically involves adjustment of a standard dose, e.g., reduction of-the dose if the patient has a low body weight.

The total dose of therapeutic agent may be administered in multiple doses or in a single dose. In certain embodiments, the compositions are administered alone, in other embodiments the compositions are administered in conjunction with other therapeutics directed to the disease or directed to other symptoms thereof.

In some aspects, the compositions of the invention are formulated into suitable pharmaceutical compositions, i.e., in a form appropriate for in vivo applications in the therapeutic intervention of a given disease. Generally, this will entail preparing compositions that are essentially free of pyrogens, as well as other impurities that could be harmful to humans or animals. In some aspects, the compositions are prepared for administration directly to the lung. These formulations are for oral administration via an inhalant, however, other routes of administration are contemplated (e.g. injection and the like). An inhaler device is any device useful in the administration of the inhalable medicament. Examples of inhaler devices include nebulizers, metered dose inhalers, dry powder inhalers, intermittent positive pressure breathing apparatuses, humidifiers, bubble environments, oxygen chambers, oxygen masks and artificial respirators. As the MPO fragments are relatively short peptides, such fragments may be well suited to formulation as an inhalable medicament. Therefore, it is particularly contemplated that the MPO fragments or the MPO fragments conjugated to active agents will be formulated as inhalable compositions. Further, the compositions of the invention include kits in which the inhalable medicament is formulated in a container suitable for administration via inhalation.

One will generally desire to employ appropriate salts and buffers to render the compositions stable and allow for uptake of the compositions at the target site. Generally, the pharmaceutical compositions of the invention are provided in lyophilized form to be reconstituted prior to administration. Alternatively, the pharmaceutical compositions may be formulated into tablet form. Buffers and solutions for the reconstitution of the pharmaceutical compositions may be provided along with the pharmaceutical formulation to produce aqueous compositions of the present invention for administration. Such aqueous compositions will comprise an effective amount of each of the therapeutic agents being used, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the therapeutic compositions, its use in therapeutic compositions is contemplated. Supplementary active ingredients also are incorporated into the compositions.

Methods of formulating proteins and peptides for therapeutic administration also are known to those of skill in the art. Administration of these compositions according to the present invention will be via any common route so long as the target tissue is available via that route. Most commonly, these compositions are formulated for oral administration, such as by an inhalant. However, other conventional routes of administration, e.g., by subcutaneous, intravenous, intradermal, intramusclar, intramammary, intraperitoneal, intrathecal, intraocular, retrobulbar, intrapulmonary (e.g., term release), aerosol, sublingual, nasal, anal, vaginal, or transdermal delivery, or by surgical implantation at a particular site also is used particularly when oral administration is problematic. The treatment may consist of a single dose or a plurality of doses over a period of time.

In certain embodiments, the active compounds are prepared for administration as solutions of free base or pharmacologically acceptable salts in water suitably mixed with a surfactant, such as hydroxypropylcellulose. Dispersions also are prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. In some aspects, the carrier is a solvent or dispersion medium containing, for example, water, ethanol, polyol (for example, glycerol, propylene glycol, and liquid polyethylene glycol, and the like), suitable mixtures thereof, and vegetable oils. The proper fluidity is maintained, for example, by the use of a coating, such as lecithin, by the maintenance of the required particle size in the case of dispersion and by the use of surfactants. The prevention of the action of microorganisms is brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions is brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients also are incorporated into the compositions.

In some aspects, the compositions of the present invention are formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also are derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. In certain embodiment, parenteral administration of the therapeutic compounds is carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. Such formulations may influence the physical state, stability, rate of in vivo release and rate of in vivo clearance of the administered agents. Depending on the route of administration, a suitable dose is calculated according to body weight, body surface areas or organ size. The availability of animal models is particularly useful in facilitating a determination of appropriate dosages of a given therapeutic. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Typically, appropriate dosages are ascertained through the use of established assays for determining blood levels in conjunction with relevant dose response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

It will be appreciated that the pharmaceutical compositions and treatment methods of the invention are useful in fields of human medicine and veterinary medicine. Thus the subject to be treated is a mammal, such as a human or other mammalian animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

The present invention also contemplated kits for use in the treatment of various disorders. Such kits include at least a first composition comprising the MPO proteins/peptides described above in a pharmaceutically acceptable carrier. Another component is a second therapeutic agent for the treatment of the disorder along with suitable container and vehicles for administrations of the therapeutic compositions. The kits may additionally comprise solutions or buffers for effecting the delivery of the first and second compositions. The kits may further comprise catheters, syringes or other delivering devices for the delivery of one or more of the compositions used in the methods of the invention. The kits may further comprise instructions containing administration protocols for the therapeutic regimens.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus are considered to constitute certain aspects for its practice. However, those of skill in the art should, in light of the present disclosure, appreciate that many changes can be made in the specific embodiments which are disclosed and still obtain a like or similar result without departing from the spirit and scope of the invention.

Example 1

Materials and Methods

The following example describes materials and assays used to identify the specific sequences of MPO that form the albumin docking peptide. More particularly, these materials and methods were used to isolate 80 and 60 kDa albumin binding proteins from human lung tissue utilizing HSA-affinity column and identified these proteins as MPO by MALDI-MS (Karas et al., Anal. Chem., 60:2299-2301 (1988)). The MPO-HC sequence (409-454; SEQ ID NO:3) was homologous with the HSA-docking sequence identified in certain bacterial proteins that interact with HSA (Retnoningrum et al., Infect. Immun., 62:2387-2394 (1994)). These studies showed that the albumin interaction with MPO was essential in inducing the transcytosis of MPO via caveolae.

Materials: MPO purified from human PMNs and polyclonal MPO antibody (Ab) were purchased from Calbiochem (San Diego, Calif.). HSA and bovine serum albumin (BSA) were from Sigma (St. Louis, Mo.). HSA affinity sepharose was prepared by coupling HSA with CNBr-activated Sepharose 4B from Pharmacia (Piscataway, N.J.). Endothelial cell growth medium was from Invitrogen (Carlsbad, Calif.) and fetal bovine serum (FBS) was from Hyclone (Logan, Utah). Endothelial cell growth supplement (ECGS) was from BD Biosciences (Bedford, Mass.). Bovine lung microvessel endothelial cells (BLMVEC) and rat lung microvessel endothelial cells (RLMVEC) were from Vec Technologies (Rensselaer, N.Y.). Peptides were synthesized as C-terminal amide (bioWORLD, Dublin, Ohio). The purity and amino acid sequence of these peptides was determined by HPLC and mass spectrometry, respectively; peptides used in this study were 98% pure. BSA-Alexa 594, cholera toxin subunit B (CTB)-Alexa 488, and secondary antibodies were from Molecular Probes (Eugene, Oreg.).

Protein purification and MALDI-MS: Human lung tissue (180 g) was washed, minced, and homogenized with 20 volumes of buffer A (20 mM Hepes/Tris/0.15 M NaCl/0.1 mM phenylmethylsufonylfluoride [PMSF]/30 pM benzamidine [BM], pH 7.4). The homogenate was centrifuged at 1000×g for 10 min and the supernatant was centrifuged at 100,000×g for 60 min. The pellet obtained was solubilized using 2.5% sodium cholate and 4 M urea (Tiruppathi et al., Proc. Natl. Acad Sci. USA, 93:250-254 (1996)). The solubilized extract was concentrated by ethanol precipitation and re-extracted with Triton X-100 (Tiruppathi et al., Proc. Natl. Acad Sci. USA, 93:250-254 (1996)). The Triton X-100 concentration in the extract was adjusted to 0.2% and applied on HSAsepharose column (1×10 cm) pre-equilibrated with buffer-B (10 MM Tris-HCl, 0.5 MM EDTA, pH 7.4 containing 0.1 mM PMSF, 30 [M BM, and 0.2% Triton X-100). The column was washed and bound proteins were eluted with 20 ml of 0.1 M citrate buffer pH 4.0 containing 0.2% Triton X-100. The proteins eluted were separated on SDS-PAGE, stained with Coomassie Brilliant Blue R-250 (CBBR-250) (FIG. 1A). The protein bands excised were digested with trypsin and peptides were analyzed using MALDI-MS at Yale University Biotechnology Resource Laboratory (New Haven, Conn.). The peptide masses were compared with known sequence using Profound search analysis on OWL database. In addition, EMBL/non-redundant database search was used to identify the amino acid sequences. Using these methods, the 80 and 60 kDa proteins were confirmed as MPO and MPO-HC, respectively (GenBank accession number P05164.).

$^{125}$I-labeling and binding of proteins: HSA and MPO were labeled with $^{125}$I using IODO-GEN reagent from Pierce (Rockford, Ill.). $^{125}$I HSA binding to the MPO peptides was determined by dot-blot analysis. Peptides were immobilized on nitrocellulose membranes and non-specific binding was blocked with bovine γ-globulin (2 mg/ml in PBS) for 1 h at 22° C. Membranes were washed 2× with PBS and incubated with $^{125}$I-labeled HSA (0.3 pM) for 2 h at 22° C. Membranes were then washed 4× with PBS containing 0.05% Tween-20 (PBST) and autoradiography was performed. In some experiments, the membranes were directly counted to determine the membrane-associated radioactivity.

Endothelial cell cultures: BLMVEC were grown in OPTI-MEM I supplemented with 15% FBS and ECGS (15 μg/ml). RLMVEC were grown in DMEM supplemented with 5% FBS.

$^{125}$I MPO binding: BLMVEC grown to confluence in 6-well culture plates were washed 2× and incubated with 5 mM Hepes/HBSS pH 7.4 (buffer C) overnight at 37° C. Cells were then washed 2× and the binding assay was initiated by adding 1 ml of 1251-MPO (10 nM) in buffer C containing bovine γ-globulin or BSA. Incubation was continued at 4° C. for 1 h. Binding was terminated by washing 3× with ice-cold buffer C and the radioactivity associated with BLMVEC monolayer was determined (Tiruppathi et al., Proc. Natl. Acad Sci. USA, 93:250-254 (1996)).

Transendotlielial $^{125}$I-MPO permeability: Transendothelial permeability of $^{125}$I-MPO in BLMVEC monolayers was determined using Transwell filter units (24, 27). BLMVEC monolayers were washed and incubated for 2 h with buffer C prior to experiments. Both luminal and abluminal chambers contained 5 mg/ml either bovine γ-globulin or BSA in buffer C at volumes of 0.5 and 1.5 ml, respectively. Tracer $^{125}$I-MPO (1×10 cpm) was added in upper compartment and 0.05-ml samples were collected from lower compartment at 15 min intervals for 90 min for determination of transendothelial $^{125}$I-MPO permeability (Tiruppathi et al., J. Biol. Chem., 272:25968-25975 (1997); John et al., Am. J. Physiol. Lung Cell Mol. Physiol., 284:L187-L196 (2003)).

$^{125}$I MPO permeability in intact lung vessels: Pulmonary vascular $^{125}$I-MPO permeability×surface area (PS) product, a measure of vascular permeability, was determined in the rat lung as described (Vogel et al., Am. J. Physiol. Lung Cell Mol. Physiol., 281:L1512-L1522 (2001)). Briefly, Krebs-perfused lung preparations received 1$^{125}$I-MPO (100,000 cpm/ml) for 10 min followed by a 6 min washout with Krebs solution and, 3 min washout with 0.1 M acetate buffer pH 4.5 at 12° C. to remove any vascular surface bound $^{125}$I-MPO.

Immunostaining: Cellular localization of MPO, albumin, CTB (a caveolae marker), and caveolin-1 was determined by confocal microscopy (Minshall et al., J. Cell Biol., 150:1057-1069 (2000); John et al., Am. J. Physiol. Lung Cell Mol. Physiol., 284:L187-L196 (2003)). BLMVEC grown to confluence on glass cover slips were incubated in serum-free medium (buffer C) for 12 h at 37° C. MPO uptake in BLMVEC was determined in the presence or absence of albumin or CTB. After incubation, the cells were washed 3× with buffer C, fixed with 4% paraformaldehyde in HBSS, and blocked for 30 min in HBSS containing 5% goat serum, and 0.1% Triton X-100. Primary Ab labeling was performed overnight at 4° C. in HBSS containing 5% goat serum. Coverslips were washed 3×, incubated with the appropriate secondary Ab (diluted 1:500) for 1 h. Cells were washed, mounted, and images were acquired with the Zeiss LSM 510 confocal microscope.

Statistical Analysis: Comparisons were made using the two-tailed Student's t test. Values were considered significant at p<0.05.

Example 2

MPO Interacts with HSA

The present example provides data that shows that MPO interacts with HSA. Using HSA-affinity column, two proteins, an 80 and a 60 kDa protein, were isolated from human lung tissue. Using MALDI-MS these proteins were confirmed to be MPO (80 kDa) and MPO-HC (60 kDa) (FIG. 1A and FIG. 1B). The MPO sequence was compared with the known HSA-binding protein sequences. The MPO-HC (residues 409 to 454; SEQ ID NO:3) showed high homology with the HSA-binding domain of the M12 protein from Streptococcus Pyogenes (Retnoningrum et al., Infect. Immun., 62:2387-2394 (1994)) and other bacterial HSA-binding proteins (Retnoningrum et al., Infect. Immun., 62:2387-2394 (1994)) (FIG. 1C). Positively charged amino acids, R and K were enriched in the HSA-binding domain of bacterial proteins (FIG. 1C). Similar positively-charged residues were also present in MPO-HC between residues 421 and 460 (FIG. 1C).

Figure 1D:
Figure 1D:

As MPO is cationic (Winterbourn et al., Curr. Opin. Hematol., 7:53-58 (2000); Anderson et al., J. Biol. Chem., 273: 47474753(1998)), it is possible that it binds negatively charged proteins. In order to assess this possibility, the inventors addressed the possibility that it interacts via charge with negatively charged albumin (pI=4.7). Peptides were synthesized peptides from MPO-HC sequence 425-454 (SEQ ID NO:20), which exhibits the albumin-docking homology with bacterial protein HSA-binding domain sequence. $^{125}$I-HSA binding to the MPO peptides was determined (see Example 1). MPO-HC sequence 425-454 (RLATELKSLNPRWDG-ERLYQEARKIVGAMV: MPO-WT-peptide, SEQ ID NO:20) showed high affinity binding to HSA (FIG. 1D and Table 1). The EARKIV motif showed no binding to HSA (FIG. 1D and Table 1).

Figure 1E:
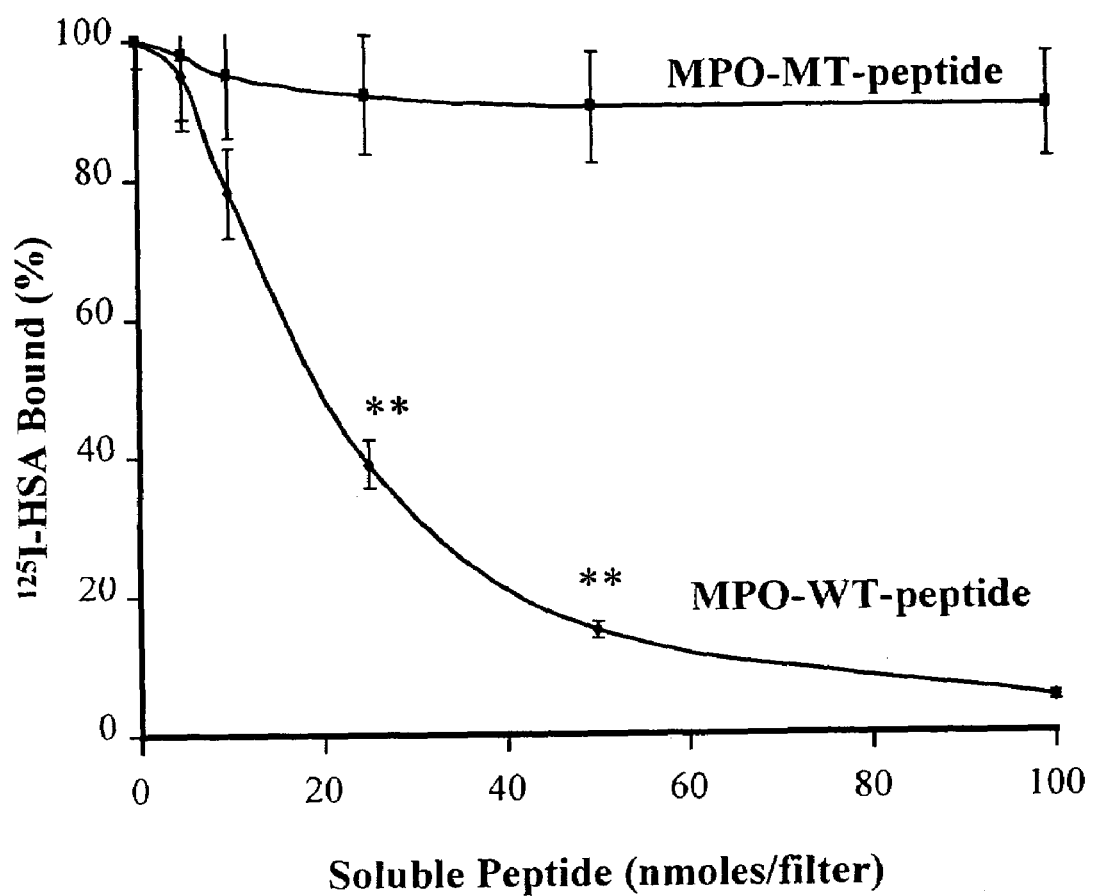

To address the role of the positive charges, the K and R were replaced with G to generate GLATELGSLNPG-WDGEGLYQEAGGIVGAMV (MPO-MT-peptide; SEQ ID NO:37), and measured HSA binding. MPO-MT-peptide failed to bind to $^{125}$I-HSA (FIG. 1D and Table 1). Thus, it appears that the length and charge on this MPO sequence are important for binding to albumin. The binding characteristics of BSA or rat serum albumin (RSA) to the MPO-WT peptide were similar to those of HSA. To address the specificity of binding of MPO peptides to albumin, WT-peptide was immobilized on nitrocellulose membrane and the binding of $^{125}$I-HSA was determined in the presence of varying concentrations of WT or MT peptide. Increasing concentrations of WT-peptide prevented the binding of $^{125}$I-HSA to the immobilized WT-peptide (FIG. 1E). However, MT-peptide had no effect on $^{125}$I-HSA binding to WT-peptide (FIG. 1E).

The binding affinity (Kd) of MPO-WT-peptide to HSA (determined using non-linear regression analysis) was determined to be 20±1.5 PM.

Table 1: Binding of Synthetic MPO Peptides to $^{125}$I-MPO

Peptides were immobilized on nitrocellulose membranes and then incubated with 1 ml of 0.3 μM $^{125}$I-HSA in PBS for 2 h. Other details were described in Example 1. Non-specific binding was determined by incubating membranes with $^{125}$I-HSA in the absence of any peptides. Results are shown mean±S.E. for three separate experiments made in triplicate.

| MPO Peptide (nmoles/filter) | $^{125}$I-HSA bound (pmoles/filter) |
|---|---|
| RLATELKSLNPRWDGERLYQEARKIVGAMV (SEQ ID NO: 20) | |
| 1.0 | 0.31 ± 0.003 |
| 2.5 | 1.45 ± 0.04 |
| 5.0 | 2.93 ± 0.07 |
| 10.0 | 6.55 ± 0.23 |
| GLATELGSLNPGWDGEGLYQEAGGIVGAMV (SEQ ID NO: 37) | |
| 1.0 | 0.01 ± 0.003 |
| 2.5 | 0.11 ± 0.035 |
| 5.0 | 0.14 ± 0.07 |
| 10.0 | 0.19 ± 0.045 |
| EARKIV (SEQ ID NO: 4) | |
| 1.0 | 0.05 ± 0.02 |
| 2.5 | 0.06 ± 0.025 |
| 5.0 | 0.08 ± 0.04 |
| 10.0 | 0.11 ± 0.06 |

Example 3

Albumin Mediates Transcytosis of MPO in vivo

The present Example shows that MPO is present in cultured endothelial cells grown in serum and that albumin binding of MPO to endothelial cell surface. This example further shows that albumin promotes the transport of MPO and that the albumin-induced transcellular MPO transport occurs via caveolae.

As endothelial cells are typically grown in serum-containing medium to mimic physiological conditions, cultured endothelial cells were assessed to determine whether such cells are coated with MPO. Cell surface staining of anti-MPO Ab as well as MPO-HC was evident in both RLMVEC and BLMVEC demonstrating that MPO is present in these cells under such conditions.

Figure 2A:
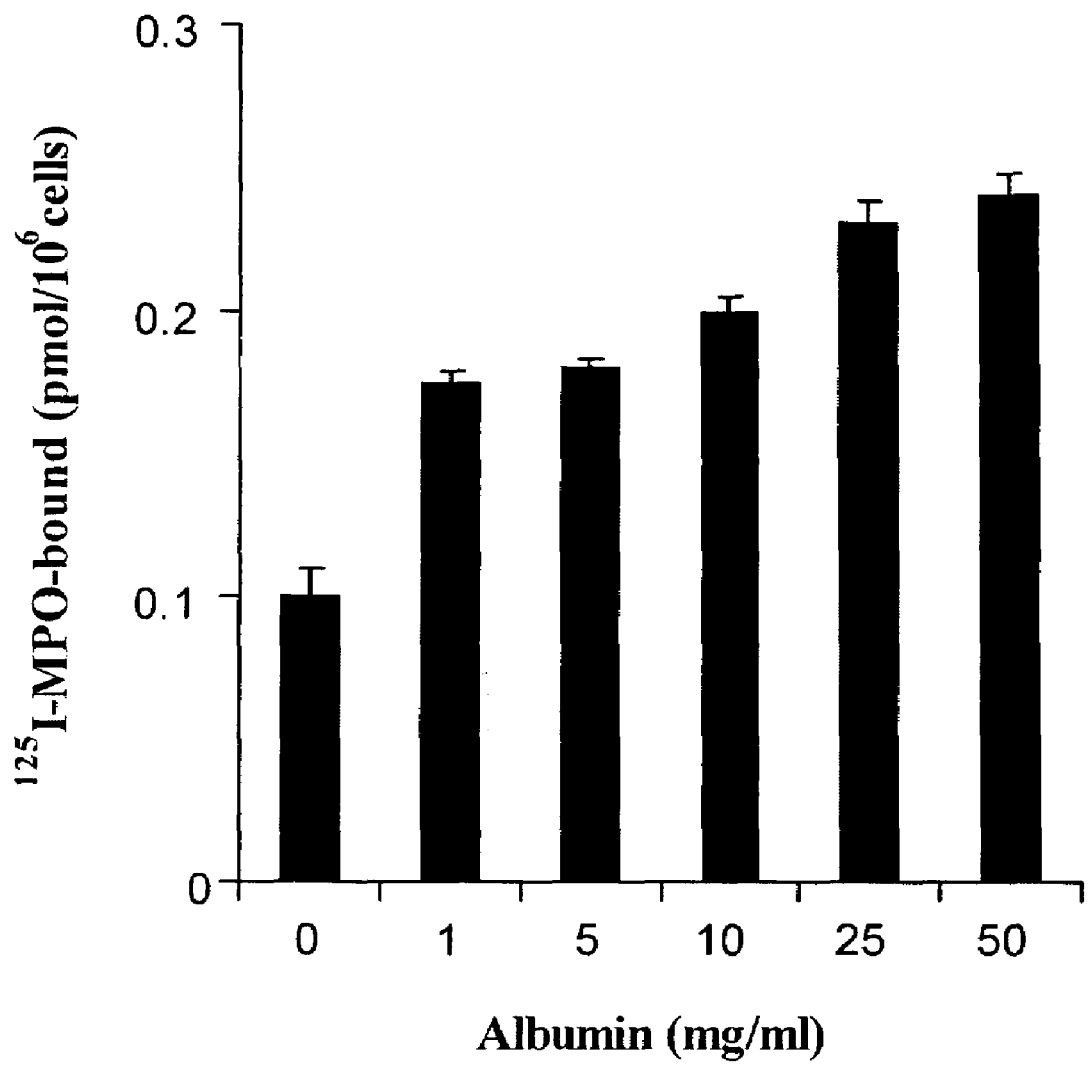
FIG. 2A-FIG. 2C: Albumin increases the binding of $^{125}$I-MPO to endothelial cell surface. The binding of $^{125}$I-MPO to BLMVEC was measured as described in Example 1. Results are shown as mean SEM of three separate experiments made in a triplicate binding assay. *, indicates difference from control ($p<0.05$); **, ($p<0.001$) different from control (i.e., binding was determined in the presence of 5 mg/ml γ-globulin). The presence or absence of 5 mg/ml γ-globulin in the binding buffer did not affect the binding of $^{125}$I-MPO to endothelial cells.

To address the role of albumin in inducing the binding of MPO, the binding of $^{125}$I-MPO to BLMVEC was determined in the presence of albumin. Increasing the concentration (1-50 mg/ml) of BSA in the binding buffer increased the binding of $^{125}$I-MPO to the endothelial cell surface (FIG. 2A). In contrast, the presence of bovine γ-globulin (5 mg/ml) had no effect on $^{125}$I-MPO binding.

Figure 2B:
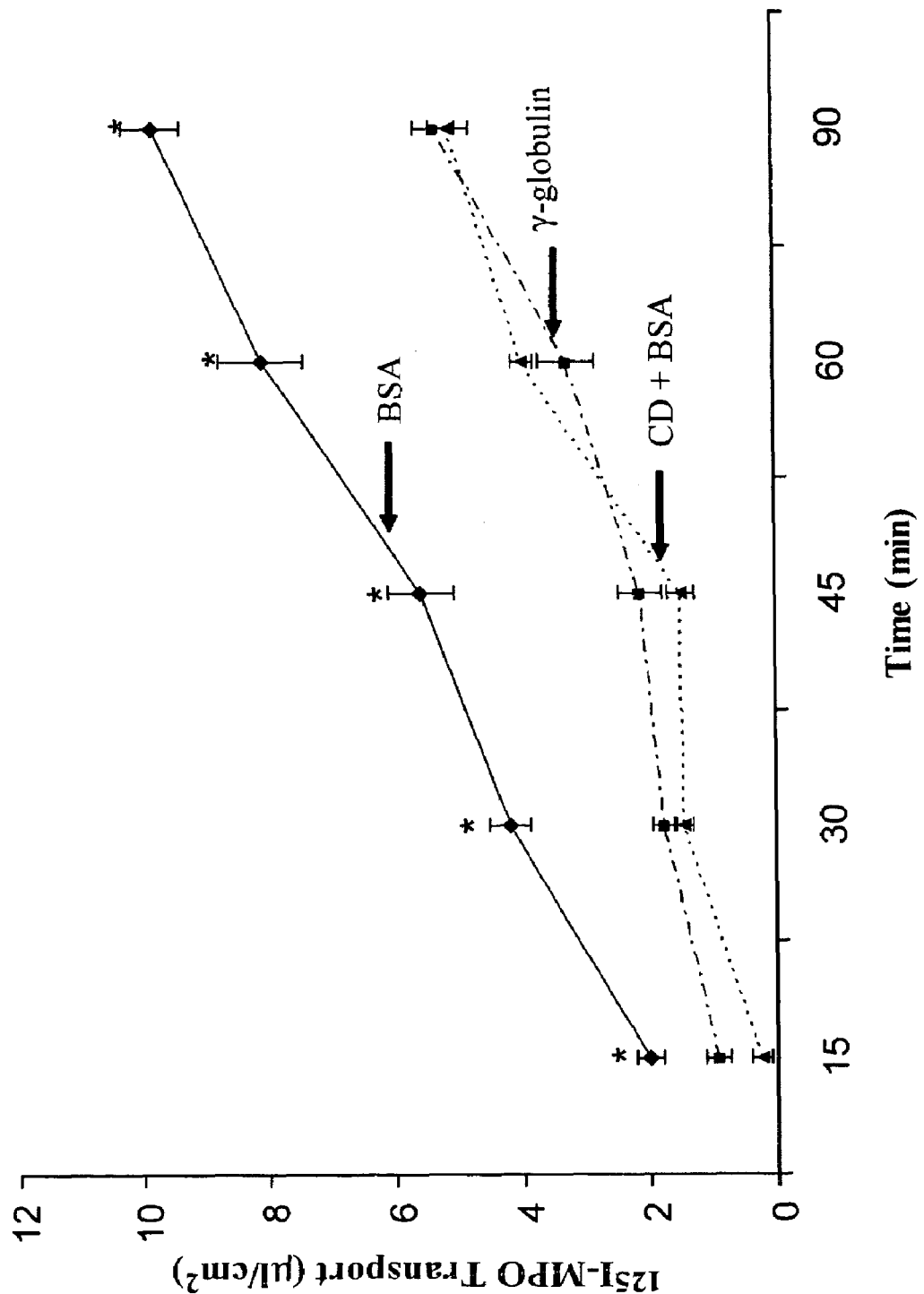
Figure 2C:
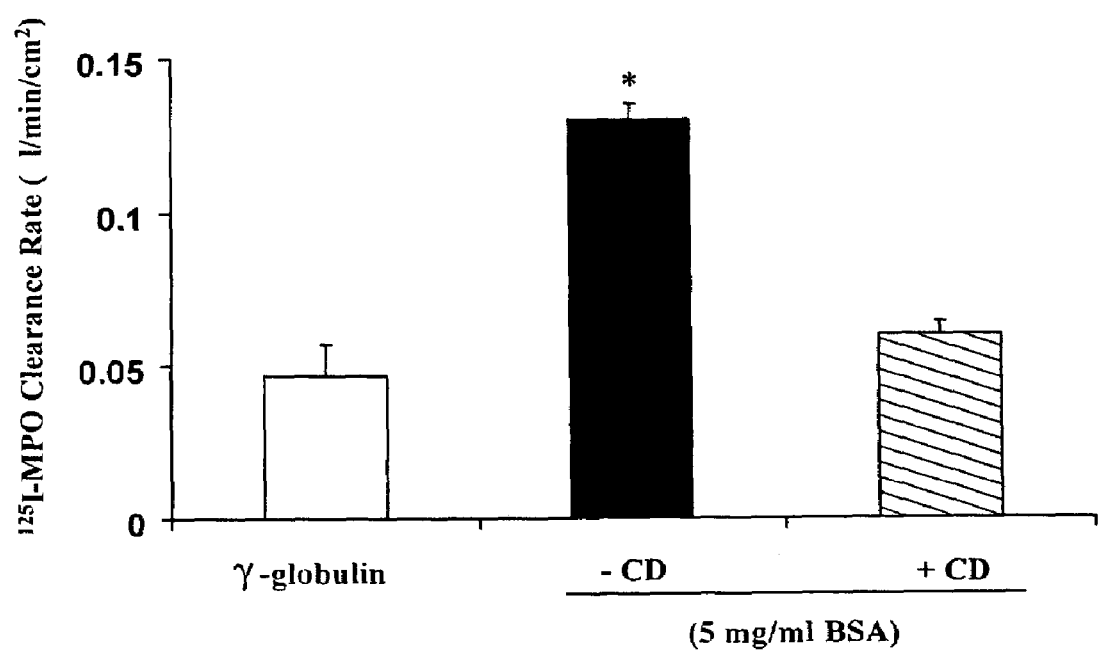

In addition, it was shown that albumin induces transendothelial transport of $^{125}$I-MPO. This was demonstrated by measuring the effects of albumin on the transendothelial transport of $^{125}$I-MPO. The appearance of $^{125}$I-MPO in the abluminal chamber was measured after adding the tracer in the luminal chamber. Transendothelial $^{1251}$I-MPO permeability increased more than 2-fold in the presence of albumin, as compared to γ-globulin (FIG. 2B). Addition of the cholesterol binding agent methyl-p-cyclodextrin (CD; 5.0 mM for 20 min) prevented the transport of $^{125}$I-MPO in the presence of albumin (FIG. 2C).

Figure 2D:
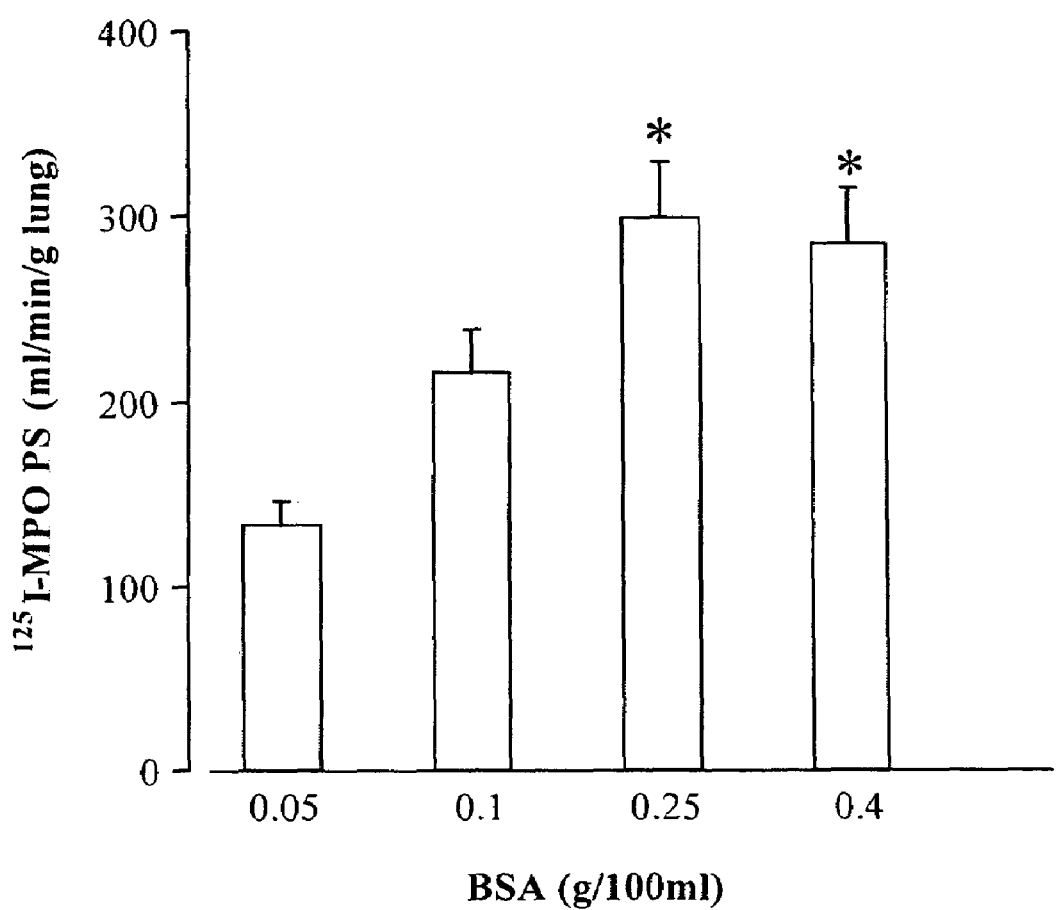
FIG. 2D: Pulmonary vascular permeability of $^{125}$I-MPO is dependent on the albumin concentration. Lung preparations were perfused at 37° C. with Krebs-albumin solutions at the indicated concentrations; MPO PS (μl/min/g wet lung) was determined by perfusing $^{125}$I-MPO for 10 min, and removing vascular tracer with Krebs for 6 min and bound tracer with cold (12° C.) acetate buffer (pH 4.5) for 3 min. $^{125}$I-MPO PS increased 2-fold upon increasing [BSA] from 0.05 to 0.4 g/100 ml. The results are shown as mean±S.E. of four separate experiments made in triplicate.

In addition, it is shown herein that albumin induces pulmonary vascular permeability of MPO. To assess vessel wall MPO permeability, the role of albumin in inducing MPO transport in lung microvessels was assessed using the isolated-perfused rat lung model (see Example 1). Pulmonary vascular $^{125}$I-MPO permeability as determined by $^{125}$I-MPO PS was dependent on the albumin concentration (FIG. 2D). Albumin concentrations of 0.05 and 0.1 g/100 ml produced 2- to 3-fold increases in the $^{125}$I-MPO PS. However, MPO PS did not increase further at higher BSA concentrations (0.25 and 0.4 g/100 ml), indicating a saturable effect of albumin on MPO transport.

Figure 3A:
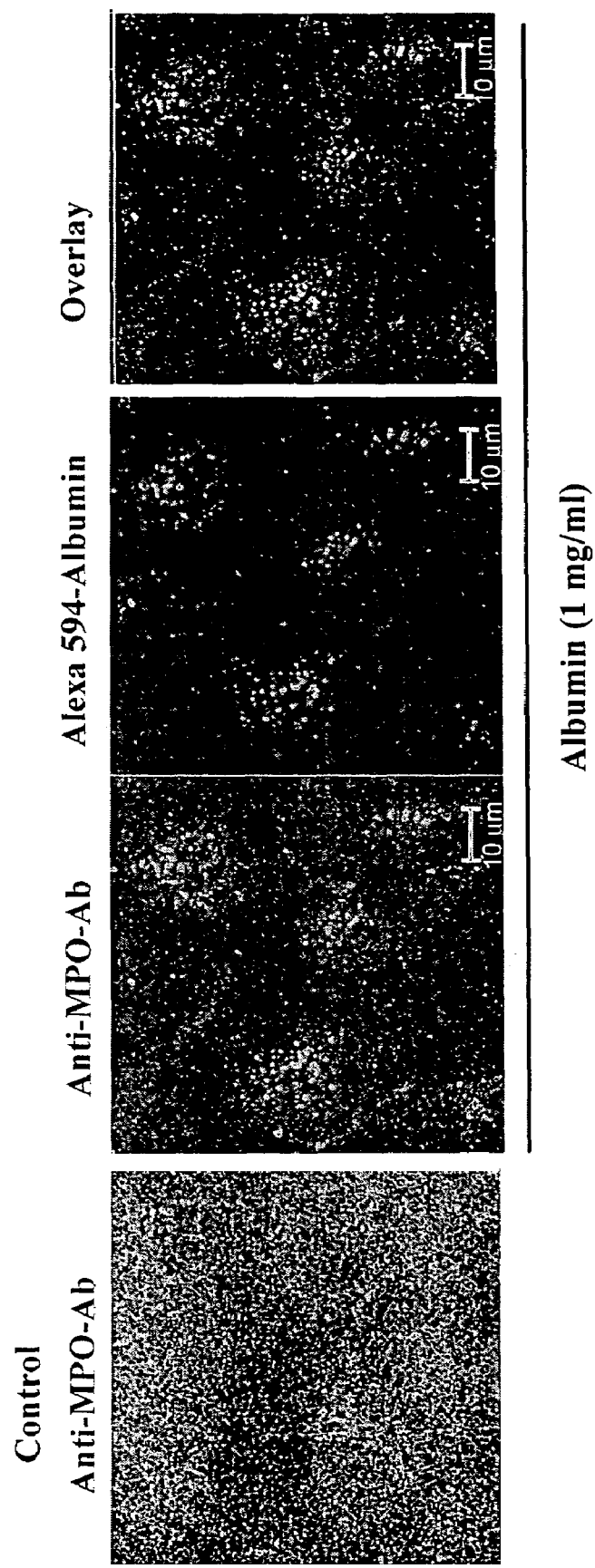
FIG. 3A-FIG. 3E: Albumin induces the endocytosis of MPO in endothelial cells. BLMVEC grown on glass coverslips were incubated with buffer C for 12 h. Cells were then incubated with buffer C containing 25 nM MPO alone or in combination with Alexa-594 BSA (50 μg/ml) and unlabeled BSA (1 mg/ml) for 30 min at 37° C. Cells were washed 3×, fixed with 4% PFA in HBSS for 30 min at 22° C., and blocked with 5% goat serum in HBBS containing 0.1% Triton X-100 (blocking buffer) for 30 min at 22° C. After washing, the cells were incubated with anti-MPO Ab diluted (1:1000) in blocking buffer at 4° C. overnight. After washing 2×, cells were incubated with Alexa-488 labeled (green) secondary Ab in blocking buffer for 60 min at 4° C. Confocal images were obtained as described in Methods. In the absence of BSA, anti-MPO Ab staining (green) was observed at the cell surface (left). In the presence of BSA, anti-MPO Ab staining (green) was seen in vesicles containing the Alexa 594 BSA (red). There was a marked co-localization of WO (green) and Alexa-594 BSA (red) in merged image (yellow; right).
Figure 3B:
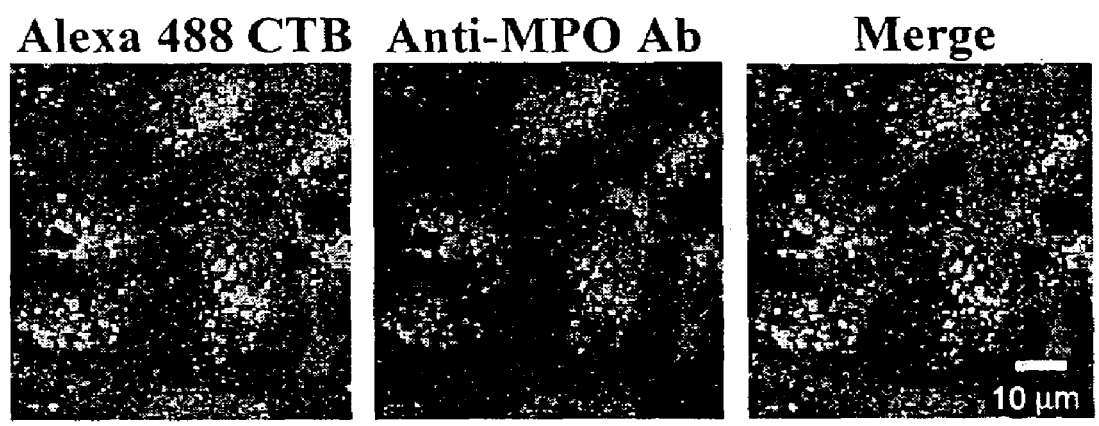
Figure 3C:
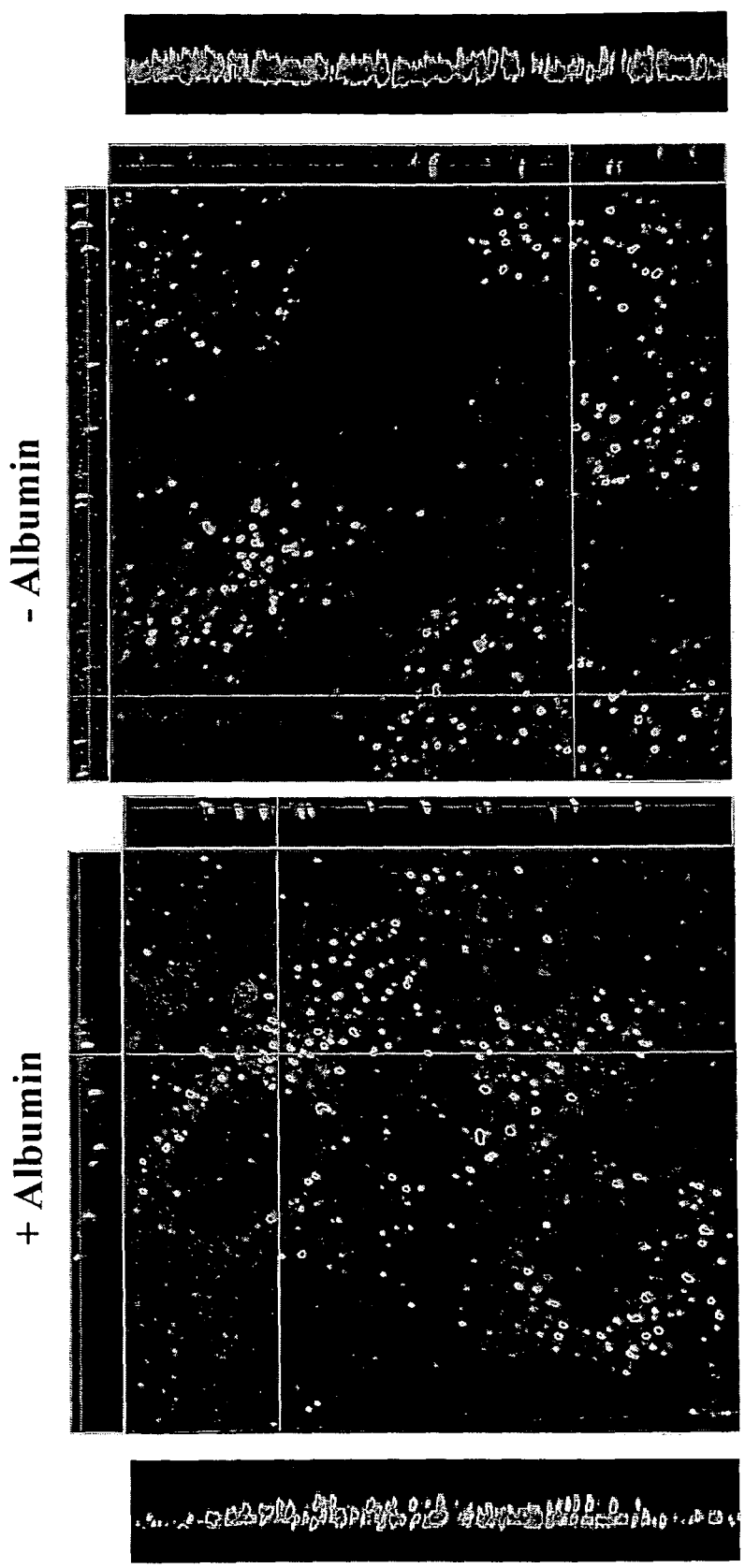
Figure 3D:
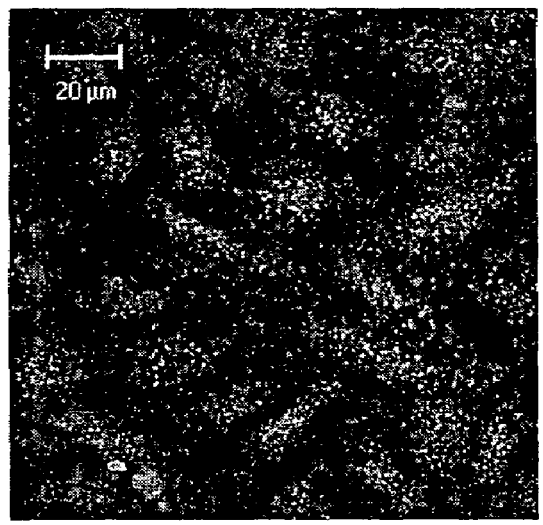
Figure 3D:
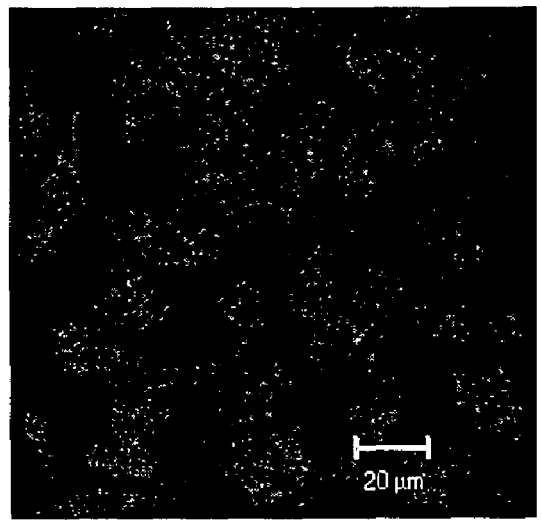

As albumin is transported across endothelial barrier via a caveolae-dependent pathway (Tiruppathi et al., J. Biol. Chem., 272:25968-25975 (1997); Minshall et al., J. Cell Biol., 150:1057-1069 (2000); Vogel et al., Am. J. Physiol. Lung Cell Mol. Physiol., 281:L1512-L1522 (2001); John et al., Am. J. Physiol. Lung Cell Mol. Physiol., 284:L187-L196 (2003)), the role of caveolae as the carriers responsible for MPO transport was assessed. BLMVEC were incubated with medium containing either 25 nM purified MPO or 25 nM purified MPO plus 1 mg/ml BSA and Alexa 594-BSA tracer for 30 min at 37° C. (see Methods). High-resolution confocal images (<1.0 pm optical thickness; pinhole set to achieve 1 Airy unit) were obtained. In the absence of albumin, MPO staining was observed only on the cell surface (FIG. 3A, left); whereas in the presence of albumin, MPO staining was markedly co-localized with albumin-containing vesicles (FIG. 3A, right). To identify the MPO-labeled caveolae, MPO uptake study was carried out in BLMVEC in the presence of the caveolae marker, Alexa 488-CTB (green), and BSA (1 mg/ml). After 30 min of incubation at 37° C., cells were washed, fixed, permeabilized, and stained with anti-MPO-Ab and secondary Ab (red). FIG. 3B shows that the internalized MPO co-localized with CTB-labeled vesicles, indicating that caveolae are the primary carriers of MPO transport. To address whether MPO and CTB were internalized together in caveolae in the presence of albumin, z-section images (0.4 μm) of immunostained MPO and CTB-Alexa 488 uptake were acquired. As shown in the x-y orthogonal view of the z-stack of images in FIG. 3C, MPO was co-localized with CTB on incubation with albumin (left panel), but MPO staining did not colocalize with CTB-positive vesicles in the absence of albumin (right panel). The y-z single line and projection images show distinctly that MPO is internalized in caveolae. In another experiment to address whether caveolae are required for MPO transport, we pretreated BLMVEC with 5.0 mM CD for 20 min at 37° C. and measured albumin-induced MPO uptake. CD treatment prevented the albumin-induced MPO uptake (FIG. 3D).

Figure 3E:
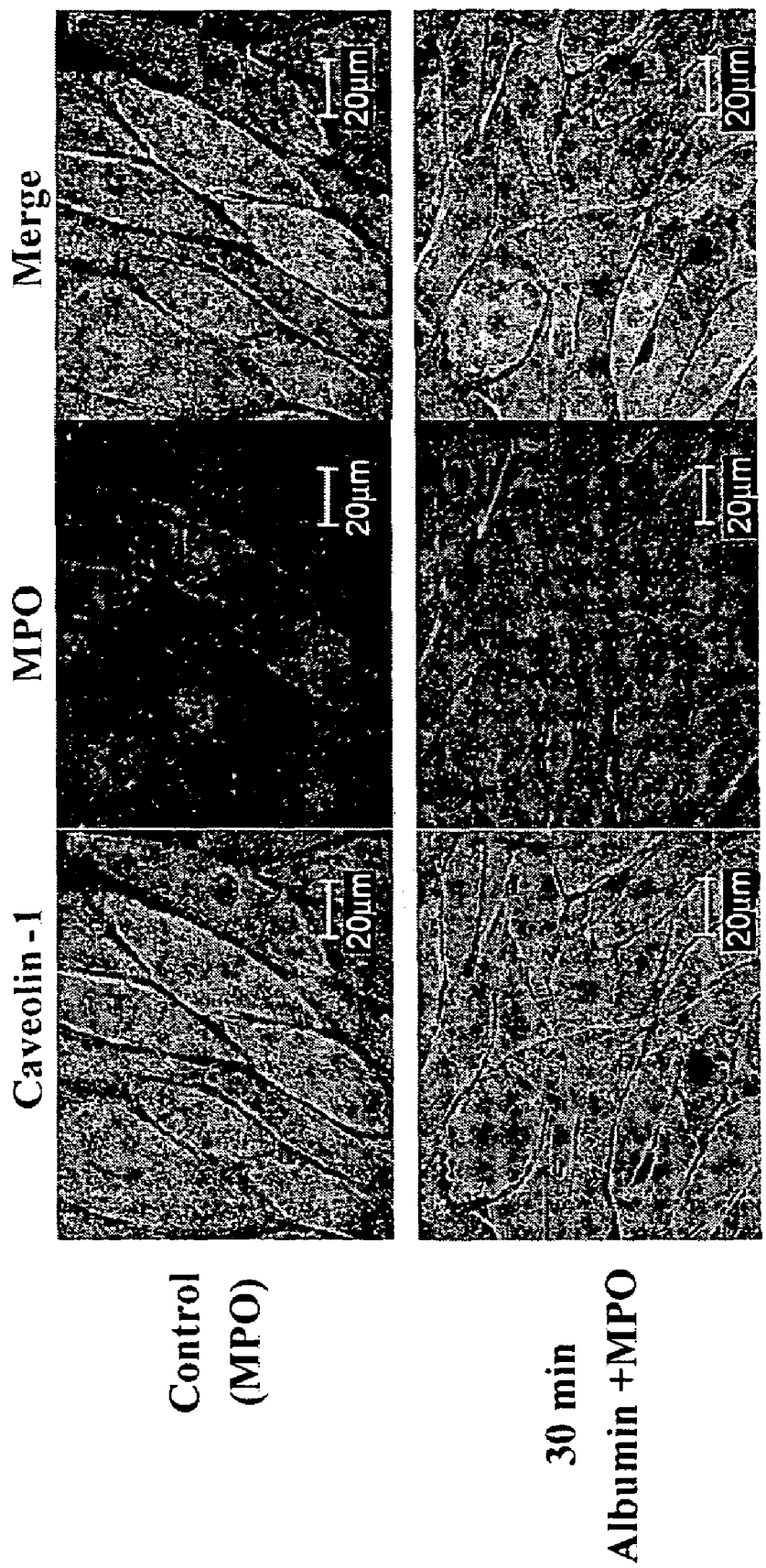

The inventors also determined whether the internalized MPO co-localized with caveolin-1, a specific protein marker of caveolae. BLMVEC were incubated at 37° C. for 30 min in medium containing 25 nM MPO in the presence BSA (5 mg/ml) and the cells were stained with antiMPO Ab and anti-caveolin-1 monoclonal antibody (mAb). MPO staining was only seen to colocalize with caveolin-1 in the presence of albumin (FIG. 3E).

The above studies demonstrate that there are specific interactions of MPO with HSA and a positive charge on MPO-HC residues 425-454 is important for this MPO binding to HSA. Further, these results show that MPO interaction with albumin induced the transcytosis of MPO via caveolae in endothelial cells. The results demonstrate that HSA binds with high affinity to the MPO-HC peptide sequence 425-454 (MPO-WT-peptide; SEQ ID NO:3) and this binding is abolished by altering the charge on this sequence by substituting G for R and K.

$^{125}$I-MPO binding to the endothelial cell surface increased in the presence of albumin and albumin induced the transendothelial transport of MPO. MPO transport resulting from its interaction with albumin was dependent on the albumin concentration and was saturable. The above results indicate that the albumin-MPO interaction induces MPO transport via a transcellular pathway dependent on albumin binding to endothelia cells. Since plasma albumin concentration is 2000- to 5000-fold molar greater MPO, the generation of MPO and its interaction with plasma albumin is likely to be the dominant means of MPO transport across the endothelial barrier.

Caveolae are the non-clathrin coated pits in endothelial cells responsible for transcytosis (Carver et al., Nature Reviews Cancer, 3:571-581 (2003)). To address the role of caveolae in the albumin-induced MPO transport, the organization of caveolae was disturbed by treating endothelial cells with methyl-B-cyclodextrin (CD), and $^{125}$I-MPO permeability was measured. CD prevented the albumin-induced increase in transendothelial $^{125}$I-MPO permeability. Further, it was seen that in the absence of albumin, MPO localized at the cell surface; however, in the presence of albumin, MPO was rapidly internalized and co-localized with the albumin-containing vesicles. It was also demonstrated that in the presence of albumin, the internalized MPO co-localized with CTB, indicating that caveolae mediated endocytosis of albumin induces the uptake and transport of MPO. MPO and caveolin-1 [the structural protein of caveolae (Carver et al., Nature Reviews Cancer, 3:571-581 (2003))] co-localized in endothelial cells after incubation with albumin; however, there was little MPO co-localized with caveolin-1 in the absence of albumin. Thus, the results show a novel model of MPO transport across the endothelial barrier (FIG. 4). Albumin interaction with the ABPs such as gp60 localized in caveolae induces vesicle trafficking across the endothelium (Tiruppathi et al., J. Biol. Chem., 272:25968-25975 (1997); Minshall et al., J. Cell Biol., 150:1057-1069 (2000); Vogel et al., Am. J. Physiol. Lung Cell Mol. Physiol., 281:L1512-L1522 (2001); John et al., Am. J. Physiol. Lung Cell Mol. Physiol., 284:L187-L196 (2003)). Since MPO interacts with albumin by a specific binding domain, albumin enables the transcytosis of MPO via caveolae. The accumulation of MPO in the sub-endothelial space as regulated by specific MPO interaction with albumin may promote extracellular matrix remodeling by generating NO-derived reactive species and nitrotyrosine formation, and thereby interfere with endothelial integrity.

The above findings may now be exploited in the production of new modes of therapeutic delivery of agents by binding the agents to MPO fragments that contain the albumin binding sequence of MPO. As long as the sequence retains an overall cationic feature it is expected to bind to albumin and the albumin mediated uptake of the MPO bound thereto will facilitate the uptake and internalization of any agent that is bound to the MPO fragment. Further as increased amounts of MPO exert their deleterious effects in the subendothelial space and interfere with endothelial integrity, it is expected that any agent that interferes with the binding and uptake of MPO with albumin in diseases in which there is an excessive production of MPO, will be a therapeutic agent for the treatment of such diseases. The MPO fragments of the present invention are expressly designed as fragments that bind to albumin. Therefore, these fragments will compete with the native MPO from the disease conditions for binding to circulating albumin and therefore these fragments will be effective as therapeutic agents for treating diseases such as acute coronary syndromes (Daugherty et al., J. Clin. Invest., 94:437-444 (1994); Brennan et al., N. Eng. J. Med., 349:1595-1604 (2003)) various inflammatory pathologies (Brennan et al., N. Eng. J. Med., 349:1595-1604 (2003); Baldus et al., on behalf of the CAPTURE Investigators, Circulation, 108:1440-1445 (2003); Zhang et al., JAMA, 286:2136-2142 (2001)). Methods and compositions for effecting such treatments have been discussed above and will be readily modifiable by those of skill in the art for the specific disease states to be treated in specific individuals.

Example 4

Use of Albumin Docking Protein for Drug Delivery to the Vascular System

As described in the above example, serum albumin binds to myeoloperoxidase (MPO). The above studies show the sequence of on MPO that specifically interacts with serum albumin. An exemplary albumin-binding protein sequence of the present invention is shown in SEQ ID NO: 20 (RLA TEL KSL NPR WDG ERL YQE ARK IVG AMV). In the present example, the inventors show that the albumin docking sequence (also referred to herein as the "albumin docking protein") can serve as a carrier molecule for drug delivery in the vascular system. The ADS peptide was synthesized and the peptide was covalently linked to recombinant insulin at the N-terminus of the peptide as described below. The insulin-ADS complex was radiolabeled with iodine-125 ($^{125}$I-insulin-ADS). The $^{125}$I-insulin-ADS transvascular flux was measured in the intact mouse lung was, utilizing the mouse lung preparation as described (Vogel, S. M., Minshall, R. D., Pilipovic, M., Tiruppathi, C., and Malik, A. B. (2001) *Am. J Physiol. Lung Cell. Mol. Physiol*. 281:L1512-L1522; John, T. A., Vogel, S. M., Tiruppathi, C., Malik, A. B., and Minshall, R. D. (2003) *Am. J. Physiol. Lung Cell. Mol. Physiol*. 284: L187-L196). These studies showed that the transport of $^{125}$I-insulin-ADS in intact lung microvessels was increased 5-fold in the presence of albumin in the perfusate compared to the same concentration of γ-globulin. This observation corroborates the use of ADS as a carrier molecule for drug delivery in circulation as contemplated herein throughout.

Peptide Syntlieis The ADS-sequence (RLA TEL KSL NPR WDG ERL YQE ARK IVG AMV; SEQ ID NO:20) was synthesized as the C-terminal amide as described in the above examples (see also Tiruppathi C, Naqvi T, Wu Y, Vogel S M, Minshall R D, and Malik A B. (2004) *Proc. Natl. Acad. Sci* USA. 101:7699-7704.). The peptide purity and amino acid sequence were verified by HPLC and mass spectrophotometry. The peptide used in this study was 98% pure.

Conjugation of ADS with recombinant insulin: Human recombinant insulin (Molecular Weight 5.8 kDa) was covalently linked to the N-terminus of ADS using EDC [1-ethyl-3-(3-dimethylaminopropyl)carbodiimide hydrochloride]. The C-terminus of insulin was linked to the N-terminus of ADS at an equimolar ratio (1:1). The cross-linking was carried out using MES (2-[N-morpholino] ethane sulfonic acid) at pH 4.5 to 5:00. After conjugation, the insulin- ADS complex was purified using a Sephadex G-15 column. The purified insulin-ADS complex was used for radio-labeling with $^{125}$I-iodine.

Figure 5:
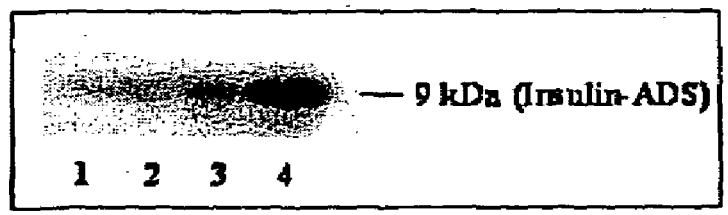
FIG. 5: $^{125}$I-labeling of insulin-ADS peptide. Radio-labeled insulin-ADS peptide was separated on 4-15% SDS-PAGE non-denaturing condition. Lane 1 to 4; increasing concentrations of $^{125}$I-labeled peptide was separated and then radioactivity associated with the peptide was determined by autoradiograph. Note: $^{125}$I-associated with the ~9 kDa size polypeptide indicating the correct size of the insulin-ADS complex.

$^2$I-Labeling of insulin-ADS: The insulin-ADS complex was radiolabeled with $^{125}$I using the IOD-GEN reagent from Pierce (Rockford, Ill.). Labeling was performed according to the manufacturer's instructions. After labeling, the $^{125}$I bound insulin-ADS complex was separated from free $^{125}$I using a Sephadex G-15 column. The $^{125}$I-labeled insulin-ADS complex was added to phosphate buffered saline supplemented with γ-globulin (2 mg/ml) at pH 7.4. The specific activity of $^{125}$I-insulin-ADS was 26.4 pmol/1×10$^6$ cpm. To determine the whether appropriate radio-labeled Insulin-ADS complex was obtained, SDS-PAGE was performed under non-denaturing conditions. The presence of $^{125}$I-labeled single polypeptide of ~9 kDa was observed (FIG. 5).

Figure 6:
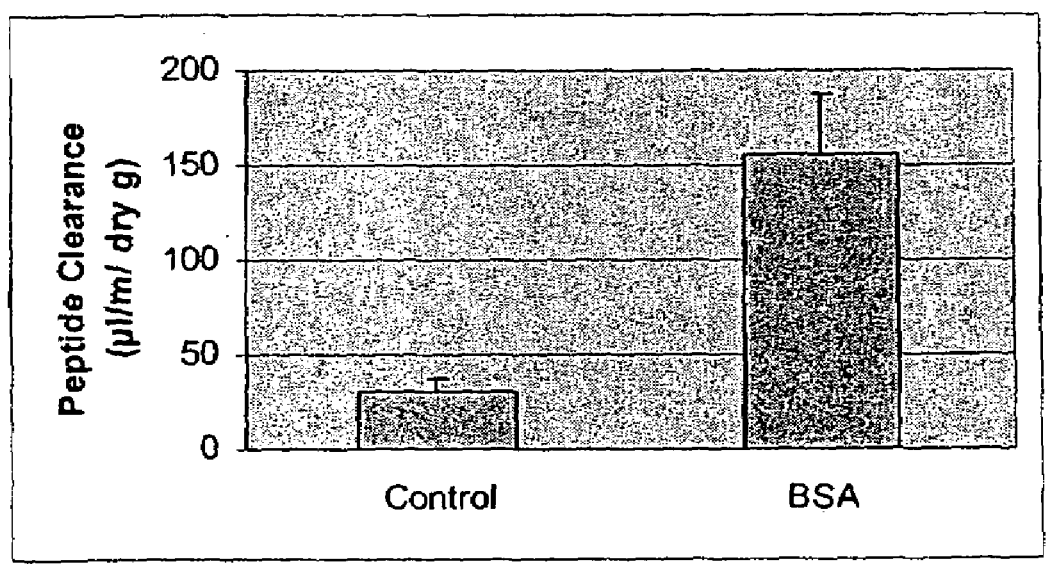
FIG. 6: Lungs from adult mice (C57bl/6) were isolated and perfused (2 ml/min, 37° C.) with RPMI medium containing 1% albumin (BSA) or 1% γ-globulin (control). Tracer molecule ($^{125}$I-labeled insulin-fuision peptide) was infused at a constant rate (0.2 min) for a 30 min period. Tracer clearance during this period was calculated and normalized by the dry weight of lung tissue. Note that the presence of albumin caused a 5-fold stimulation of peptide transport. Mean values (n=3) are given with standard deviations.

Albumin increases the permeability (transport) of $^{125}$I-labeled insulin-ADS in lung microvessels: These experiments were designed to demonstrated specific activation of $^{125}$I-labeled insulin-ADS transport by albumin. The isolated mouse lung preparation was perfused (2 ml/min) with RPMI solution (37° C., pH 7.4), containing 1% albumin or 1% γ-globulin as control (Tiruppathi et al., 2004; Vogel et al., 2001; John et al., 2003). A standard infusion of the tracer molecule (0.2 ml/min;~100,000 cpm/ml) was then provided for 30 min. At the end of the labeling period, vascular tracer was washed out for 6 min and the vessels were acid washed for an additional 4 min to remove tracer bound to the vascular endothelial surface. The lung was then removed from the perfusion apparatus and quantified tissue radioactivity using a γ-counter. A very pronounced activating effect of albumin on tissue clearance of $^{125}$I-labeled insulin-ADS was observed, as the clearance value was 5-fold greater in the presence of albumin than in the presence of an inactive control molecule (γ-globulin) (FIG. 6). These results show that the ADS sequence can be used to delivery a cargo molecule (i.e., insulin) in an albumin dependent manner. These data are not limited to insulin and any other agent to be delivered could be delivered in like manner.

The following paragraphs provide exemplary embodiments of the present invention:

Paragraph 1. An albumin docking protein (ADP) comprising the sequence of ELKSLNPRWDGE (SEQ ID NO:3) wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3.

Paragraph 2. The ADP of paragraph 1, wherein the ADP does not have an amino acid sequence of SEQ ID NO:2.

Paragraph 3. A compound comprising an ADP comprising an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3, linked through a linker to an agent of interest.

Paragraph 4. The compound of paragraph 3, wherein the agent is selected from the group consisting of a therapeutic agent, a diagnostic agent, a marker of a disease, a labeled monoclonal antibody which binds a marker of a disease.

Paragraph 5. The compound of paragraph 4, wherein the therapeutic agent is selected from the group consisting of a protein, a chemotherapeutic agent, a protein nucleic acid, an siRNA molecule, an antisense molecule, and an expression construct comprising a nucleic acid that encodes a therapeutic protein of interest.

Paragraph 6. The compound of paragraph 3, wherein the ADP and the agent of interest are directly linked to each other.

Paragraph 7. The compound of paragraph 5, wherein the ADP is linked to insulin as the agent of interest.

Paragraph 8. The compound of paragraph 3, wherein the linker is a peptide linker.

Paragraph 9. The compound of paragraph 3, wherein the ADP binds to albumin and mediates the uptake of the agent of interest via albumin-mediated transcytosis through caveolae.

Paragraph 10. The compound of any of paragraphs 3-8, or a peptide of paragraphs 1 or 2, wherein the ADP comprises a positive charge.

Paragraph 11. The compound of any of paragraphs 3-8, or a peptide of paragraphs 1 or 2, wherein the ADP comprises residues RK of SEQ ID NO:2.

Paragraph 12. The compound of any of paragraphs 3-8, or a peptide of paragraphs 1. or 2, wherein the ADP further comprises a sequence of EARKIV (SEQ ID NO:4).

Paragraph 13. The compound of any of paragraphs 3-8 or a peptide of paragraphs 1 or 2, wherein the ADP comprises a sequence of any of the amino acid sequences of SEQ ID NO:5 to SEQ ID NO:36.

Paragraph 14. A method of delivering an agent into a cell comprising contacting the cell with:

(i) an agent conjugated to an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3, or (ii) an agent linked through a linker to an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3, wherein the transport of the agent conjugated to the ADP across the cell membrane of the cell is greater than the transport of the agent in the absence of conjugation to the ADP.

Paragraph 15. A method of increasing transcytosis of an agent, comprising:

(i) conjugating the agent to an ADP protein that comprises the sequence of ELKSLNPRWDGE (SEQ ID NO:3), wherein said ADP is not a fill-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3, or (ii) linking an agent through a linker to an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3, wherein transcytosis of the agent when conjugated or linked through a linker to the ADP is greater than the transcytosis of the agent in the absence of the conjugation or linkage through a linker.

Paragraph 16. A method of treating a disorder in a mammal comprising administering to the mammal:

(i) a therapeutic agent conjugated to an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3, or (ii) a therapeutic agent linked through a linker with an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3.

Paragraph 17. The method of paragraph 16, wherein the disorder is selected from the group consisting of a cardiovascular disease, a cancer, an inflammatory disease, and an autoimmune disease.

Paragraph 18. The method of paragraph 17, wherein the disorder is a cancer and the agent is a chemotherapeutic agent.

Paragraph 19. A method of delivering a therapeutic agent to the subendothelial space in an organ in a mammal, comprising administering to the mammal (i) a therapeutic composition comprising the therapeutic agent conjugated to an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3, or (ii) a therapeutic composition comprising the therapeutic agent linked through a linker with an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3 wherein the uptake of the therapeutic enzyme into the subendothelial space is mediated through caveolae on the surface of the cell.

Paragraph 20. A method of treating a disease comprising delivering a therapeutic agent to the sub-endothelial space, wherein the delivering comprises administering in an amount effective to ameliorate the symptoms of the disease:

(i) a therapeutic composition comprising an ADP that consists of the sequence of SEQ ID NO:2 or a fragment or conservative variant thereof, that retains the albumin docking activity of a peptide of SEQ ID NO:2, conjugated to a therapeutic agent used in the treatment of the cardiovascular disease, or (ii) a therapeutic composition comprising an ADP comprising the sequence of SEQ ID NO:2 or a fragment or conservative variant thereof, that retains the albumin docking activity of a peptide of SEQ ID NO:2, linked through a linker to a therapeutic agent used in the treatment of the cardiovascular disease.

Paragraph 21. The method of paragraph 20, wherein disease is a cardiovascular disease.

Paragraph 22. The method of paragraph 20, wherein the mammal is a human.

Paragraph 23. The method of paragraph 20, wherein the disease is a disease of the CNS and the transcytosis facilitates the transport of the therapeutic agent across the blood brain barrier.

Paragraph 24. The method of paragraph 23, wherein the CNS disorder is selected from the group consisting of Alzheimer's Disease, Parkinson's Disease, multiple sclerosis, and amylotrophic lateral sclerosis, and a CNS neoplasia.

Paragraph 25. A pharmaceutical composition comprising an ADP of paragraph 1 in combination with a pharmaceutically acceptable carrier, diluent or excipient.

Paragraph 26. A pharmaceutical composition comprising a compound of paragraph 3 in combination with a pharmaceutically acceptable carrier, diluent or excipient.

Paragraph 27. A composition comprising an ADP of paragraph 1 for use in the treatment of a disorder in need of the ADP.

Paragraph 28. The composition of paragraph 27, wherein the disorder is a cardiovascular disorder.

Paragraph 29. The composition of paragraph 27, wherein the disorder is an inflammatory disorder.

Paragraph 30. A composition comprising a compound of paragraph 3 for use in the treatment of a disorder in need of the therapeutic agent of the compound.

Paragraph 31. A method of treating an inflammatory disorder in an animal comprising administering to the animal a composition comprising an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3 in amount effective to treat the inflammatory disorder.

Paragraph 32. The method of paragraph 31, wherein the inflammatory disorder is an inflammatory disorder caused by an excessive production of myeloperoxidase.

Paragraph 33. The method of paragraph 31, wherein the inflammatory disorder is a chronic inflammatory disorder.

Paragraph 34. The method of paragraph 31, wherein the inflammatory disorder is an acute inflammatory disorder.

Paragraph 35. A method of inhibiting tyrosine nitration in a biological sample comprising contacting the biological sample with an ADP protein that comprises the sequence of ELKSLNPRWDGE (SEQ ID NO:3), wherein said ADP is not a full-length myeloperoxidase protein and wherein the ADP consists of a sequence of any one of the sequences set forth in SEQ ID NO:3 and SEQ ID NO:5 through 36 or a fragment or conservative variant of any of the sequence of SEQ ID NO:3 or SEQ ID NO:5 through 36 that retains the albumin docking activity of a peptide of SEQ ID NO:3, wherein the ADP inhibits MPO activation of the tyrosine nitration.

Paragraph 36. The method of paragraph 35, wherein the biological sample is contacted with the ADP in vitro.

Paragraph 37. The method of paragraph 35, wherein the biological sample is contacted with the ADP in vivo.

Paragraph 38. The method of paragraph 35, wherein the biological sample is comprises endothelial cells.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

What is claimed is:

1. An isolated albumin docking protein (ADP) consisting of a sequence of any one of the sequences set forth in SEQ ID NO:3 and SEQ ID NO:5 through 36 or consisting of a fragment or conservative amino acid substituted variant of any of the sequence of SEQ ID NO: 3 or SEQ ID NO:5 through 36 that retains the albumin docking activity of a peptide of SEQ ID NO:3.

2. A compound comprising an albumin docking protein (ADP) consisting of a sequence of any one of the sequences set forth in SEQ ID NO:3 and SEQ ID NO:5 through 36 or consisting of a fragment or conservative amino acid substituted variant of any of the sequence of SEQ ID NO:3 or SEQ ID NO: 5 through 36 that retains the albumin docking activity of a peptide of SEQ ID NO:3, said ADP linked through a linker to an agent of interest that is heterologous to the ADP.

3. The compound of claim 2, wherein the agent is selected from the group consisting of a therapeutic agent, a diagnostic agent, a marker of a disease, a labeled monoclonal antibody which binds a marker of a disease.

4. The compound of claim 3, wherein the therapeutic agent is selected from the group consisting of a protein, a chemotherapeutic agent, a protein nucleic acid, an siRNA molecule, an antisense molecule, and an expression construct comprising a nucleic acid that encodes a therapeutic protein of interest.

5. The compound of claim 2, wherein the ADP and the agent of interest are directly linked to each other.

6. The compound of claim 4, wherein the ADP is linked to insulin as the agent of interest.

7. The compound of claim 2, wherein the linker is a peptide linker.

8. The compound of claim 2, wherein the ADP binds to albumin and mediates the uptake of the agent of interest via albumin-mediated transcytosis through caveolae.

9. The compound of any of claims 2-7, or an ADP of claims 1, wherein the ADP comprises a positive charge.

10. The compound of any of claims 2-7, or an ADP of claim 1, wherein the ADP comprises residues RK (amino acids 447-448) of SEQ ID NO: 2.

11. The compound of any of claims 2-7, or an ADP of claims 1, wherein the ADP further comprises a sequence of EARKIV (SEQ ID NO: 4).

12. The compound of any of claims 2-7 or an ADP of claim 1, wherein the ADP consists of a sequence of any of the amino acid sequences of SEQ ID NO: 5 to SEQ ID NO: 36.

13. A pharmaceutical composition comprising a compound of claim 2 in combination with a pharmaceutically acceptable carrier, diluent or excipient.

14. A pharmaceutical composition comprising an albumin docking protein (ADP) of claim 1 in combination with a pharmaceutically acceptable carrier, diluent or excipient.

* * * * *

UNITED STATES PATENT AND TRADEMARK OFFICE
CERTIFICATE OF CORRECTION

PATENT NO. : 7,429,563 B2  Page 1 of 1
APPLICATION NO. : 11/514578
DATED : September 30, 2008
INVENTOR(S) : Chinnaswamy Tiruppathi et al.

It is certified that error appears in the above-identified patent and that said Letters Patent is hereby corrected as shown below:

On the Title Page:

In the (*) Notice field, the text "This patent is subject to a terminal disclaimer." should be deleted.

Signed and Sealed this

Second Day of December, 2008

JON W. DUDAS
*Director of the United States Patent and Trademark Office*